(12) United States Patent
Herring et al.

(10) Patent No.: US 8,779,103 B2
(45) Date of Patent: Jul. 15, 2014

(54) DRUG FUSIONS AND CONJUGATES

(75) Inventors: Christopher Herring, Cambridgeshire (GB); Lucy J. Holt, Cambridgeshire (GB); Laurent S. Jespers, Cambridgeshire (GB); Sebastian Mayer, Cambridgeshire (GB); Malgorzata Pupecka-Swider, Cambridgeshire (GB)

(73) Assignee: Glaxo Group Limited, Brentford, Middlesex (GB)

( * ) Notice: Subject to any disclaimer, the term of this patent is extended or adjusted under 35 U.S.C. 154(b) by 155 days.

(21) Appl. No.: 13/256,957

(22) PCT Filed: Mar. 24, 2010

(86) PCT No.: PCT/EP2010/053806
§ 371 (c)(1),
(2), (4) Date: Sep. 16, 2011

(87) PCT Pub. No.: WO2010/108937
PCT Pub. Date: Sep. 30, 2010

(65) Prior Publication Data
US 2012/0100141 A1    Apr. 26, 2012

Related U.S. Application Data

(60) Provisional application No. 61/163,917, filed on Mar. 27, 2009.

(51) Int. Cl.
| C12P 21/08 | (2006.01) |
| A61K 39/395 | (2006.01) |
| C07K 16/46 | (2006.01) |
| C07K 14/575 | (2006.01) |
| C12N 15/62 | (2006.01) |
| A61P 3/00 | (2006.01) |
| A61P 3/04 | (2006.01) |
| A61P 3/08 | (2006.01) |

(52) U.S. Cl.
USPC ............ 530/387.3; 530/388.25; 424/178.1; 424/134.1; 424/145.1; 424/195.11; 424/192.1; 514/4.9; 514/5.2; 514/5.3; 514/7.9

(58) Field of Classification Search
None
See application file for complete search history.

(56) References Cited

U.S. PATENT DOCUMENTS

| 2006/0052301 A1 | 3/2006 | Shemesh et al. | |
| 2008/0260757 A1* | 10/2008 | Holt et al. | 424/179.1 |
| 2009/0259026 A1* | 10/2009 | Tomlinson et al. | 530/387.3 |
| 2011/0020345 A1* | 1/2011 | Herring et al. | 424/134.1 |
| 2011/0300158 A1* | 12/2011 | De Angelis et al. | 424/158.1 |
| 2011/0305696 A1* | 12/2011 | De Angelis et al. | 424/134.1 |
| 2012/0276098 A1* | 11/2012 | Hamilton et al. | 424/134.1 |

FOREIGN PATENT DOCUMENTS

| WO | WO 90/11296 | | 10/1990 |
| WO | WO 91/11457 A1 | | 8/1991 |
| WO | WO 98/05351 A1 | | 2/1998 |
| WO | WO 99/07404 A1 | | 2/1999 |
| WO | WO 99/25727 A2 | | 5/1999 |
| WO | WO 99/25728 A1 | | 5/1999 |
| WO | WO 99/40788 A1 | | 8/1999 |
| WO | WO 99/43708 A1 | | 9/1999 |
| WO | WO 02/46227 A2 | | 6/2002 |
| WO | WO 2005/027978 A2 | | 3/2005 |
| WO | WO 2006/059106 A2 | | 6/2006 |
| WO | WO 2008096158 | * | 8/2008 |
| WO | WO 2008/149143 A2 | | 12/2008 |
| WO | WO 2009/121804 A1 | | 10/2009 |

OTHER PUBLICATIONS

Kobrin et al., J Immunology 146: 2017-2020, 1991.*
Wu et al., J. Mol. Biol. 294: 151-162, 1999.*
W-F. Dou, et al., Protein Expression and Purification, vol. 61, No. 1, pp. 45-49, May 10, 2008.
L. Holt, et al., Protein Engineering, Design & Selection, vol. 21, No. 5, pp. 283-288, May 2008.
Hung, et al., Diabetes, 53:2461-2466, 2004.

* cited by examiner

*Primary Examiner* — Phuong Huynh
(74) *Attorney, Agent, or Firm* — Kathryn L. Coulter; Jonathan Dermott

(57) ABSTRACT

The present invention relates to drug fusions that have improved serum half lives. These fusions and conjugates comprise polypeptides, immunoglobulin (antibody) single variable domains and GLP and/or exendin molecules. The invention further relates to uses, formulations, compositions and devices comprising such drug fusions and conjugates.

11 Claims, 30 Drawing Sheets

FIG. 1A: Amino acid sequences of:

(a) 2xGLP-1 A8G DOM7h-14 fusion (DAT0114)

HGEGTFTSDVSSYLEGQAAKEFIAWLVKGRHGEGTFTSDVSSYLEGQAAKEFIAWLVKG
RDIQMTQSPSSLSASVGDRVTITCRASQWIGSQLSWYQQKPGKAPKLLIMWRSSLQSGV
PSRFSGSGSGTDFTLTISSLQPEDFATYYCAQGAALPRTFGQGTKVEIKR

(SEQ ID NO 1)

(b) Exendin 4, (G4S)3 linker, DOM7h-14 fusion (DAT0115)

HGEGTFTSDLSKQMEEEAVRLFIEWLKNGGPSSGAPPPSGGGGGSGGGGSGGGGSDIQM
TQSPSSLSASVGDRVTITCRASQWIGSQLSWYQQKPGKAPKLLIMWRSSLQSGVPSRFSG
SGSGTDFTLTISSLQPEDFATYYCAQGAALPRTFGQGTKVEIKR

(SEQ ID NO 2)

(c) Exendin 4 DOM7h-14 fusion (DAT0116)

HGEGTFTSDLSKQMEEEAVRLFIEWLKNGGPSSGAPPPSGDIQMTQSPSSLSASVGDRVT
ITCRASQWIGSQLSWYQQKPGKAPKLLIMWRSSLQSGVPSRFSGSGSGTDFTLTISSLQPE
DFATYYCAQGAALPRTFGQGTKVEIKR

(SEQ ID NO 3)

(d) Exendin 4, helical linker, DOM7h-14 fusion (DAT0117)

HGEGTFTSDLSKQMEEEAVRLFIEWLKNGGPSSGAPPPSGKEAAAKEAAAKEAAAKEL
AAKEAAAKEAAAKEAAAKELAADIQMTQSPSSLSASVGDRVTITCRASQWIGSQLSWY
QQKPGKAPKLLIMWRSSLQSGVPSRFSGSGSGTDFTLTISSLQPEDFATYYCAQGAALPR
TFGQGTKVEIKR

(SEQ ID NO 4)

FIG. 1B (e) GLP-1 A8G, (G4S)3, linker DOM7h-14 fusion (DAT0118)
HGEGTFTSDVSSYLEGQAAKEFIAWLVKGRGGGGSGGGGSGGGGSDIQMTQSPSSLSAS
VGDRVTITCRASQWIGSQLSWYQQKPGKAPKLLIMWRSSLQSGVPSRFSGSGSGTDFTL
TISSLQPEDFATYYCAQGAALPRTFGQGTKVEIKR
(SEQ ID NO 5)

(f) GLP-1 A8G, PSS linker, DOM7h-14 fusion (DAT0119)
HGEGTFTSDVSSYLEGQAAKEFIAWLVKGRGPSSDIQMTQSPSSLSASVGDRVTITCRAS
QWIGSQLSWYQQKPGKAPKLLIMWRSSLQSGVPSRFSGSGSGTDFTLTISSLQPEDFATY
YCAQGAALPRTFGQGTKVEIKR
(SEQ ID NO 6)

(g) GLP-1 A8G, helical linker, DOM7h-14 fusion (DAT0120)
HGEGTFTSDVSSYLEGQAAKEFIAWLVKGRGKEAAAKEAAAKEAAAKELAAKEAAAK
EAAAKEAAAKELAADIQMTQSPSSLSASVGDRVTITCRASQWIGSQLSWYQQKPGKAP
KLLIMWRSSLQSGVPSRFSGSGSGTDFTLTISSLQPEDFATYYCAQGAALPRTFGQGTKV
EIKR
(SEQ ID NO 7)

(h) DOM7h-14:
DIQMTQSPSSLSASVGDRVTITC<u>RASQWIGSQLS</u>WYQQKPGKAPKLLIM<u>WRSSLQ</u>SGVP
SRFSGSGSGTDFTLTISSLQPEDFATYYC<u>AQGAALPRT</u>FGQGTKVEIKR
(SEQ ID NO 8)

(i) GLP-1 (7-37) A8G:
HGEGTFTSDVSSYLEGQAAKEFIAWLVKGRG
(SEQ ID NO 9)

FIG. 1C (j) exendin-4:

HGEGTFTSDLSKQMEEEAVRLFIEWLKNGGPSSGAPPPS

(SEQ ID NO 10)

(k) helical linker:

KEAAAKEAAAKEAAAKELAAKEAAAKEAAAKEAAAKELAA

(SEQ ID NO 11)

(l) Gly-ser linker:

GGGGGSGGGGSGGGGS

(SEQ ID NO 12)

(m) Exendin 4, (G4S)3, linker DOM7h-14-10 fusion (DMS7139)

HGEGTFTSDLSKQMEEEAVRLFIEWLKNGGPSSGAPPPSGGGGGSGGGGSGGGGSDIQM
TQSPSSLSASVGDRVTITCRASQWIGSQLSWYQQKPGKAPKLLIMWRSSLQSGVPSRFSG
SGSGTDFTLTISSLQPEDFATYYCAQGLRHPKTFGQGTKVEIKR

(SEQ ID NO 24)

(n) Exendin 4, (G4S)3, linker DOM7h-11-15 fusion (DMS7143)

HGEGTFTSDLSKQMEEEAVRLFIEWLKNGGPSSGAPPPSGGGGGSGGGGSGGGGSDIQM
TQSPSSLSASVGDRVTITCRASRPIGTMLSWYQQKPGKAPKLLILAFSRLQSGVPSRFSGS
GSGTDFTLTISSLQPEDFATYYCAQAGTHPTTFGQGTKVEIKR

(SEQ ID NO 25)

FIG. 1D

(o) DOM7h-14-10

DIQMTQSPSSLSASVGDRVTITC<u>RASQWIGSQLS</u>WYQQKPGKAPKLLIM<u>WRSSLQS</u>GVP
SRFSGSGSGTDFTLTISSLQPEDFATYYC<u>AQGLRHPKT</u>FGQGTKVEIKR

(SEQ ID NO 26)

(p) DOM7h-11-15

DIQMTQSPSSLSASVGDRVTITC<u>RASRPIGTMLS</u>WYQQKPGKAPKLLIL<u>AFSRLQS</u>GVPSR
FSGSGSGTDFTLTISSLQPEDFATYYC<u>AQAGTHPTT</u>FGQGTKVEIKR

(SEQ ID NO 27)

(q) OmpT AWA signal peptide (leader)

MRAKLLGIVLTTPIAISAWA

(SEQ ID NO 28)

(r) DOM7h-14-10R108C diqmtqspsslsasvgdrvtitcrasqwigsqlswyqqkpgkapkllimwrsslqsgvps
rfsgsgsgtdftltisslqpedfatyycaqglrhpktfgqgtkveikc

(SEQ ID NO 42)

(s) PYY 3-36 (with a lysine at position 10)

IKPEAPGKDASPEELNRYYASLRHYLNLVTRQRY

(SEQ ID NO 43)

FIG. 2A (a) DAT0114 – nucleic acid sequence (from mammalian construct):
CATGGTGAAGGGACCTTTACCAGTGATGTAAGTTCTTATTTGGAAGGCCAAGCTGCC
AAGGAATTCATTGCTTGGCTGGTGAAAGGCCGACATGGTGAAGGGACCTTTACCAG
TGATGTAAGTTCTTATTTGGAAGGCCAAGCTGCCAAGGAATTCATTGCTTGGCTGGT
GAAAGGCCGAGACATCCAGATGACCCAGTCTCCATCCTCCCTGTCTGCATCTGTAGG
AGACCGTGTCACCATCACTTGCCGGGCAAGTCAGTGGATTGGGTCTCAGTTATCTTG
GTACCAGCAGAAACCAGGGAAAGCCCCTAAGCTCCTGATCATGTGGCGTTCCTCGTT
GCAAAGTGGGGTCCCATCACGTTTCAGTGGCAGTGGATCTGGGACAGATTTCACTCT
CACCATCAGCAGTCTGCAACCTGAAGATTTTGCTACGTACTACTGTGCTCAGGGTGC
GGCGTTGCCTAGGACGTTCGGCCAAGGGACCAAGGTGGAAATCAAACGG
(SEQ ID NO 13)

(b) DAT0115 – nucleic acid sequence (from mammalian construct):
CATGGTGAAGGAACATTTACCAGTGACTTGTCAAAACAGATGGAAGAGGAGGCAGT
GCGGTTATTTATTGAGTGGCTTAAGAACGGAGGACCAAGTAGCGGGGCACCTCCGC
CATCGGGTGGTGGAGGCGGTTCAGGCGGAGGTGGCAGCGGCGGTGGCGGGTCGGAC
ATCCAGATGACCCAGTCTCCATCCTCCCTGTCTGCATCTGTAGGAGACCGTGTCACC
ATCACTTGCCGGGCAAGTCAGTGGATTGGGTCTCAGTTATCTTGGTACCAGCAGAAA
CCAGGGAAAGCCCCTAAGCTCCTGATCATGTGGCGTTCCTCGTTGCAAAGTGGGGTC
CCATCACGTTTCAGTGGCAGTGGATCTGGGACAGATTTCACTCTCACCATCAGCAGT
CTGCAACCTGAAGATTTTGCTACGTACTACTGTGCTCAGGGTGCGGCGTTGCCTAGG
ACGTTCGGCCAAGGGACCAAGGTGGAAATCAAACGG
(SEQ ID NO 14)

FIG. 2B (c) DAT0115 – nucleic acid sequence (from E. coli construct):
CACGGTGAAGGTACCTTCACCTCTGACCTGAGCAAACAGATGGAGGAAGAAGCGGT
TCGTCTGTTCATCGAGTGGCTGAAAAACGGTGGTCCGTCTTCTGGTGCTCCGCCACC
GTCTGGTGGTGGTGGTGGTTCTGGTGGTGGTGGTTCTGGTGGTGGCGGTAGCGACAT
CCAGATGACTCAGTCCCCAAGCTCTCTGTCTGCCTCCGTTGGCGATCGTGTTACGAT
CACGTGCCGTGCTTCTCAGTGGATCGGTTCCCAGCTGTCCTGGTATCAGCAGAAACC
GGGCAAAGCCCCGAAACTCCTGATCATGTGGCGTAGCTCTCTGCAGTCTGGTGTACC
GAGCCGCTTCTCTGGTTCTGGTTCTGGTACCGACTTCACCCTGACCATTTCCTCTCTG
CAGCCGGAAGATTTCGCGACCTACTACTGTGCTCAGGGTGCGGCACTGCCACGTACT
TTTGGCCAGGGTACGAAAGTCGAGATTAAACGTTAATGA
(SEQ ID NO 15)

(d) DAT0116 – nucleic acid sequence (from mammalian construct):
CATGGTGAAGGAACATTTACCAGTGACTTGTCAAAACAGATGGAAGAGGAGGCAGT
GCGGTTATTTATTGAGTGGCTTAAGAACGGAGGACCAAGTAGCGGGGCACCTCCGC
CATCGGGTGACATCCAGATGACCCAGTCTCCATCCTCCCTGTCTGCATCTGTAGGAG
ACCGTGTCACCATCACTTGCCGGGCAAGTCAGTGGATTGGGTCTCAGTTATCTTGGT
ACCAGCAGAAACCAGGGAAAGCCCCTAAGCTCCTGATCATGTGGCGTTCCTCGTTGC
AAAGTGGGGTCCCATCACGTTTCAGTGGCAGTGGATCTGGGACAGATTTCACTCTCA
CCATCAGCAGTCTGCAACCTGAAGATTTTGCTACGTACTACTGTGCTCAGGGTGCGG
CGTTGCCTAGGACGTTCGGCCAAGGGACCAAGGTGGAAATCAAACGG
(SEQ ID NO 16)

FIG. 2C (e) DAT0116 – nucleic acid sequence (from E. coli construct):
CACGGTGAAGGTACCTTCACCTCTGACCTGAGCAAACAGATGGAGGAAGAAGCGGT
TCGTCTGTTCATCGAGTGGCTGAAAAACGGTGGTCCGTCTTCTGGTGCTCCGCCACC
GTCTGACATCCAGATGACTCAGTCCCCAAGCTCTCTGTCTGCCTCCGTTGGCGATCG
TGTTACGATCACGTGCCGTGCTTCTCAGTGGATCGGTTCCCAGCTGTCCTGGTATCAG
CAGAAACCGGGCAAAGCCCCGAAACTCCTGATCATGTGGCGTAGCTCTCTGCAGTCT
GGTGTACCGAGCCGCTTCTCTGGTTCTGGTTCTGGTACCGACTTCACCCTGACCATTT
CCTCTCTGCAGCCGGAAGA
TTTCGCGACCTACTACTGTGCTCAGGGTGCGGCACTGCCACGTACTTTTGGCCAGGG
TACGAAAGTCGAGATTAAACGTTAATGA
(SEQ ID NO 17)

(f) DAT0117 – nucleic acid sequence (from mammalian construct):
CATGGTGAAGGAACATTTACCAGTGACTTGTCAAAACAGATGGAAGAGGAGGCAGT
GCGGTTATTTATTGAGTGGCTTAAGAACGGAGGACCAAGTAGCGGGGCACCTCCGC
CATCGGGTAAAGAAGCGGCGGCGAAAGAAGCGGCGGCGAAAGAAGCGGCGGCGAA
AGAATTGGCCGCAAAAGAAGCGGCGGCGAAAGAAGCGGCGGCGAAAGAAGCGGCG
GCGAAAGAATTGGCCGCAGACATCCAGATGACCCAGTCTCCATCCTCCCTGTCTGCA
TCTGTAGGAGACCGTGTCACCATCACTTGCCGGGCAAGTCAGTGGATTGGGTCTCAG
TTATCTTGGTACCAGCAGAAACCAGGGAAAGCCCCTAAGCTCCTGATCATGTGGCGT
TCCTCGTTGCAAAGTGGGGTCCCATCACGTTTCAGTGGCAGTGGATCTGGGACAGAT
TTCACTCTCACCATCAGCAGTCTGCAACCTGAAGATTTTGCTACGTACTACTGTGCTC
AGGGTGCGGCGTTGCCTAGGACGTTCGGCCAAGGGACCAAGGTGGAAATCAAACGG
(SEQ ID NO 18)

FIG. 2D (g) DAT0117 – nucleic acid sequence (from E. coli construct):
CACGGTGAAGGTACCTTCACCTCTGACCTGAGCAAACAGATGGAGGAAGAAGCGGT
TCGTCTGTTCATCGAGTGGCTGAAAAACGGTGGTCCGTCTTCTGGTGCTCCGCCACC
GTCTAAAGAAGCGGCGGCGAAAGAAGCGGCGGCGAAAGAAGCGGCGGCGAAAGAA
TTGGCCGCAAAAGAAGCGGCGGCGAAAGAAGCGGCGGCGAAAGAAGCGGCGGCGA
AAGAATTGGCCGCAGACATCCAGATGACTCAGTCCCCAAGCTCTCTGTCTGCCTCCG
TTGGCGATCGTGTTACGATCACGTGCCGTGCTTCTCAGTGGATCGGTTCCCAGCTGTC
CTGGTATCAGCAGAAACCGGGCAAAGCCCCGAAACTCCTGATCATGTGGCGTAGCT
CTCTGCAGTCTGGTGTACCGAGCCGCTTCTCTGGTTCTGGTTCTGGTACCGACTTCAC
CCTGACCATTTCCTCTCTGCAGCCGGAAGATTTCGCGACCTACTACTGTGCTCAGGG
TGCGGCACTGCCACGTACTTTTGGCCAGGGTACGAAAGTCGAGATTAAACGTTAATG
A
(SEQ ID NO 19)

(h) DAT0118 – nucleic acid sequence (from mammalian construct):
CATGGTGAAGGGACCTTTACCAGTGATGTAAGTTCTTATTTGGAAGGCCAAGCTGCC
AAGGAATTCATTGCTTGGCTGGTGAAAGGCCGAGGTGGAGGCGGTTCAGGCGGAGG
TGGCAGCGGCGGTGGCGGGTCGGACATCCAGATGACCCAGTCTCCATCCTCCCTGTC
TGCATCTGTAGGAGACCGTGTCACCATCACTTGCCGGGCAAGTCAGTGGATTGGGTC
TCAGTTATCTTGGTACCAGCAGAAACCAGGGAAAGCCCCTAAGCTCCTGATCATGTG
GCGTTCCTCGTTGCAAAGTGGGGTCCCATCACGTTTCAGTGGCAGTGGATCTGGGAC
AGATTTCACTCTCACCATCAGCAGTCTGCAACCTGAAGATTTTGCTACGTACTACTGT
GCTCAGGGTGCGGCGTTGCCTAGGACGTTCGGCCAAGGGACCAAGGTGGAAATCAA
ACGG
(SEQ ID NO 20)

FIG. 2E (i) DAT0119 – nucleic acid sequence (from mammalian construct):
CATGGTGAAGGGACCTTTACCAGTGATGTAAGTTCTTATTTGGAAGGCCAAGCTGCC
AAGGAATTCATTGCTTGGCTGGTGAAAGGCCGAGGACCAAGCTCGGACATCCAGAT
GACCCAGTCTCCATCCTCCCTGTCTGCATCTGTAGGAGACCGTGTCACCATCACTTG
CCGGGCAAGTCAGTGGATTGGGTCTCAGTTATCTTGGTACCAGCAGAAACCAGGGA
AAGCCCCTAAGCTCCTGATCATGTGGCGTTCCTCGTTGCAAAGTGGGGTCCCATCAC
GTTTCAGTGGCAGTGGATCTGGGACAGATTTCACTCTCACCATCAGCAGTCTGCAAC
CTGAAGATTTTGCTACGTACTACTGTGCTCAGGGTGCGGCGTTGCCTAGGACGTTCG
GCCAAGGGACCAAGGTGGAAATCAAACGG
(SEQ ID NO 21)

(j) DAT0120 – nucleic acid sequence (from mammalian construct):
CATGGTGAAGGGACCTTTACCAGTGATGTAAGTTCTTATTTGGAAGGCCAAGCTGCC
AAGGAATTCATTGCTTGGCTGGTGAAAGGCCGAGGAAAAGAAGCGGCGGCGAAAG
AAGCGGCGGCGAAAGAAGCGGCGGCGAAAGAATTGGCCGCAAAAGAAGCGGCGGC
GAAAGAAGCGGCGGCGAAAGAAGCGGCGGCGAAAGAATTGGCCGCAGACATCCAG
ATGACCCAGTCTCCATCCTCCCTGTCTGCATCTGTAGGAGACCGTGTCACCATCACTT
GCCGGGCAAGTCAGTGGATTGGGTCTCAGTTATCTTGGTACCAGCAGAAACCAGGG
AAAGCCCCTAAGCTCCTGATCATGTGGCGTTCCTCGTTGCAAAGTGGGGTCCCATCA
CGTTTCAGTGGCAGTGGATCTGGGACAGATTTCACTCTCACCATCAGCAGTCTGCAA
CCTGAAGATTTTGCTACGTACTACTGTGCTCAGGGTGCGGCGTTGCCTAGGACGTTC
GGCCAAGGGACCAAGGTGGAAATCAAACGG
(SEQ ID NO 22)

FIG. 2F (k) Dom7h-14 – nucleic acid sequence
GACATCCAGATGACCCAGTCTCCATCCTCCCTGTCTGCATCTGTAGGAGACCGTGTC
ACCATCACTTGCCGGGCAAGTCAGTGGATTGGGTCTCAGTTATCTTGGTACCAGCAG
AAACCAGGGAAAGCCCCTAAGCTCCTGATCATGTGGCGTTCCTCGTTGCAAAGTGGG
GTCCCATCACGTTTCAGTGGCAGTGGATCTGGGACAGATTTCACTCTCACCATCAGC
AGTCTGCAACCTGAAGATTTTGCTACGTACTACTGTGCTCAGGGTGCGGCGTTGCCT
AGGACGTTCGGCCAAGGGACCAAGGTGGAAATCAAACGG
(SEQ ID NO 23)

(l) Exendin 4, (G4S)3, linker DOM7h-14-10 fusion (DMS7139)
CATGGTGAAGGAACATTTACCAGTGACTTGTCAAAACAGATGGAAGAGGAGGCAGT
GCGGTTATTTATTGAGTGGCTTAAGAACGGAGGACCAAGTAGCGGGGCACCTCCGC
CATCGGGTGGTGGAGGCGGTTCAGGCGGAGGTGGCAGCGGCGGTGGCGGGTCGGAC
ATCCAGATGACCCAGTCTCCATCCTCCCTGTCTGCATCTGTAGGAGACCGTGTCACC
ATCACTTGCCGGGCAAGTCAGTGGATTGGGTCTCAGTTATCTTGGTACCAGCAGAAA
CCAGGGAAAGCCCCTAAGCTCCTGATCATGTGGCGTTCCTCGTTGCAAAGTGGGGTC
CCATCACGTTTCAGTGGCAGTGGATCTGGGACAGATTTCACTCTCACCATCAGCAGT
CTGCAACCTGAAGATTTTGCTACGTACTACTGTGCTCAGGGTTTGAGGCATCCTAAG
ACGTTCGGCCAAGGGACCAAGGTGGAAATCAAACGG
(SEQ ID NO 29)

FIG. 2G (m) Exendin 4, (G4S)3, linker DOM7h-11-115 fusion (DMS7143)
CATGGTGAAGGAACATTTACCAGTGACTTGTCAAAACAGATGGAAGAGGAGGCAGT
GCGGTTATTTATTGAGTGGCTTAAGAACGGAGGACCAAGTAGCGGGGCACCTCCGC
CATCGGGTGGTGGAGGCGGTTCAGGCGGAGGTGGCAGCGGCGGTGGCGGGTCGGAC
ATCCAGATGACCCAGTCTCCATCCTCCCTGTCTGCATCTGTAGGAGACCGTGTCACC
ATCACTTGCCGGGCAAGTCGTCCGATTGGGACGATGTTAAGTTGGTACCAGCAGAA
ACCAGGGAAAGCCCCTAAGCTCCTGATCCTTGCTTTTTCCCGTTTGCAAAGTGGGGT
CCCATCACGTTTCAGTGGCAGTGGATCTGGGACAGATTTCACTCTCACCATCAGCAG
TCTGCAACCTGAAGATTTTGCTACGTACTACTGCGCGCAGGCTGGGACGCATCCTAC
GACGTTCGGCCAAGGGACCAAGGTGGAAATCAAACGG
(SEQ ID NO 30)

(n) Dom7h-14-10 – nucleic acid
GACATCCAGATGACCCAGTCTCCATCCTCCCTGTCTGCATCTGTAGGAGACCGTGTC
ACCATCACTTGCCGGGCAAGTCAGTGGATTGGGTCTCAGTTATCTTGGTACCAGCAG
AAACCAGGGAAAGCCCCTAAGCTCCTGATCATGTGGCGTTCCTCGTTGCAAAGTGGG
GTCCCATCACGTTTCAGTGGCAGTGGATCTGGGACAGATTTCACTCTCACCATCAGC
AGTCTGCAACCTGAAGATTTTGCTACGTACTACTGTGCTCAGGGTTTGAGGCATCCT
AAGACGTTCGGCCAA GGGACCAAGGTGGAAATCAAACGG
(SEQ ID NO 31)

FIG. 2H (o) Dom7h-11-15 – nucleic acid

GACATCCAGATGACCCAGTCTCCATCCTCCCTGTCTGCATCTGTAGGAGACCGTGTC
ACCATCACTTGCCGGGCAAGTCGTCCGATTGGGACGATGTTAAGTTGGTACCAGCAG
AAACCAGGGAAAGCCCCTAAGCTCCTGATCCTTGCTTTTTCCCGTTTGCAAAGTGGG
GTCCCATCACGTTTCAGTGGCAGTGGATCTGGGACAGATTTCACTCTCACCATCAGC
AGTCTGCAACCTGAAGATTTTGCTACGTACTACTGCGCGCAGGCTGGGACGCATCCT
ACGACGTTCGGCCAA GGGACCAAGGTGGAAATCAAACGG (SEQ ID NO 32)

(p) OmpAWA signal peptide – nucleic acid sequence atgcgggcgaaactcctaggaatagtcctgacaaccccctatcgcgatcagcgcttgggcc (SEQ ID NO 33)

(q) DOM 7h-14-10 R108C – nucleic acid sequence gacatccagatgacccagtctccatcctccctgtctgcatctgtaggagaccgtgtcaccatcacttgccgggcaagtcagtggattgggtct
cagttatcttggtaccagcagaaaccagggaaagcccctaagctcctgatcatgtggcgttcctcgttgcaaagtggggtcccatcacgtttc
agtggcagtggatctgggacagatttcactctcaccatcagcagtctgcaacctgaagattttgctacgtactactgtgctcagggtttgaggc
atcctaagacgttcggccaagggaccaaggtggaaatcaaatgt (SEQ ID NO 44)

FIG. 2I (r) Cynomolgus GLP-1 receptor cDNA sequence
ATGGCCGGCACCCCCGGCCCGCTGCGCCTCGCGCTCCTGCTGCTCGGGGTGGTGGGC
AGGGCCGGCCCCCGCCCCCAGGGTGCCACTGTGTCCCTCTGGGAGACGGTGCAGAA
ATGGCGAGAATACCGACGCCAGTGCCAGCGCTCCCTGACTGAGGACCCACCTCCCG
CCACAGACTTGTTCTGCAACCGGACCTTCGATGAATATGCCTGCTGGCCAGATGGGG
AGCCAGGCTCCTTCGTGAATGTCAGCTGCCCCTGGTACCTGCCCTGGGCCAGCAGTG
TGCCGCAGGGCCACGTGTACCGGTTCTGCACAGCTGAAGGCCTCTGGCTGCAGAAG
GACAACTCCAGCCTGCCCTGGAGGGACTTGTCGGAGTGTGAGGAGTCCAAGCGAGG
GGAGAGAAATTCCCCGGAGGAGCAGCTCCTGTCCCTCTACATCATCTACACGGTGG
GCTACGCACTCTCCTTCTCTGCTCTGGTTATCGCCTCTGCGATCCTCCTTGGCTTCAG
ACACCTGCACTGCACCCGGAACTACATCCACCTGAACCTGTTTGCATCCTTCATCCT
GCGAGCATTGTCCGTCTTCATCAAGGACGCAGCCCTCAAGTGGATGTACAGCACGG
CCGCCCAGCAGCACCAGTGGGATGGGCTCCTCTCCTACCAGGACTCTCTGGGCTGCC
GCGTGGTGTTTCTGCTCATGCAATACTGTGTGGCGGCCAATTACTACTGGCTCTTGGT
GGAGGGCGTGTACCTGTACACACTGCTGGCCTTCTCGGTCTTCTCTGAGCAACGAAT
CTTCAGGCTGTATGTGAGCGTAGGCTGGGGTGTTCCCCTGCTGTTTGTTGTCCCCTGG
GGCATTGTCAAGTACCTCTATGAGGACGAGGGCTGCTGGACCAGGAACTCCAACAT
GAACTACTGGCTCATTATCCGGCTGCCCATTCTCTTTGCCATTGGGGTGAACTTCCTC
ATCTTTGTTCGGGTCATCTGCATCGTGGTATCCA AACTGAAGGCCAATCTCATG
TGCAAGACAGACATCAAATGCAGACTTGCCAAGTCCACGCTGACACTCATCCCCCTG
CTGGGGACTCATGAGGTCATCTTTGCCTTTGTGATGGACGAGCATGCCCGGGGCACC
CTGCGCTTCATCAAGCTGTTCACGGAGCTCTCCTTTACCTCCTTCCAGGGGCTGATGG
TGGCCATCTTGTACTGCTTTGTCAACAATGAGGTCCAGTTGGAATTTCGGAAGAGCT
GGGAGCGCTGGCGGCTTGAGCACTTGCACATCCAGAGGGACAGCAGCATGAAGCCC
CTCAAGTGTCCCACCAGCAGCCTGAGCAGTGGGGCCACGGCGGGCAGCAGCATGTA
CACAGCCACTTGCCAGGCCTCCTGCAGC
(SEQ ID NO 45)

FIG. 2J

(s) Oligonucleotide 1

GGAATTCCATATGAAAATCAAAACCGGTGCTCGCATCCTGGCTCTGTCCGCTCTGAC
CACTATGATGTTCTCCGCTTCCGCGCTGGCTCATGGTGAAGGAACATTTACCAGTGA
C (SEQ ID NO 47)

(t) Oligonucleotide 2

GTTCAGAATTCTTATTACCGTTTGATTTCCACCTTGGTCCCTTG (SEQ ID NO 48)

(u) DMS 7139 nucleic acid sequence for E. coli expression cacggtgaaggtacgttcacctctgacctgagcaaacagatggaggaagaagcggttcgtctgttcatcgagtggctgaaaaacggtggtc
cgtcttctggtgctccgccgccgtctggtggtggtggtggttctggtggtggtggttctggtggtggtggcagcgatatccagatgactcagt
ccccgtcttctctctccgcctctgttggcgaccgtgttaccatcacttgtcgtgcgagccagtggatcggttcccagctgagctggtatcagca
gaaaccgggcaaagcgccgaaactgctgatcatgtggcgctctagcctgcagtctggtgtaccgtctcgtttctccggctctggttctggtac
ggacttcaccctcacgatctcttccctgcagccggaagactttgccacctactactgcgcacagggtctgcgtcacccgaaaaccttcggtc
agggtaccaaagtcgagatcaaacgt (SEQ ID NO 50)

FIG. 3A: shows dose dependent reduction in body weight in mouse model of obesity by administering DAT0115.
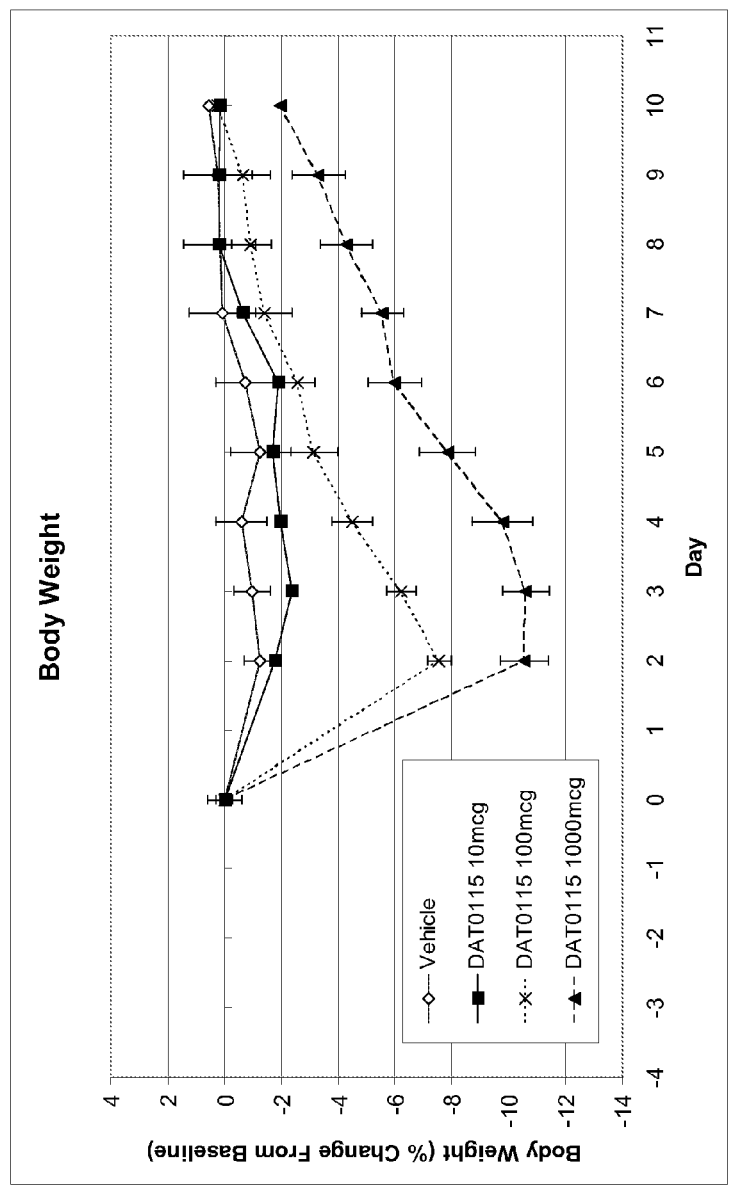

FIG. 3B: shows daily food consumption in mouse model of obesity by administering DAT0115.
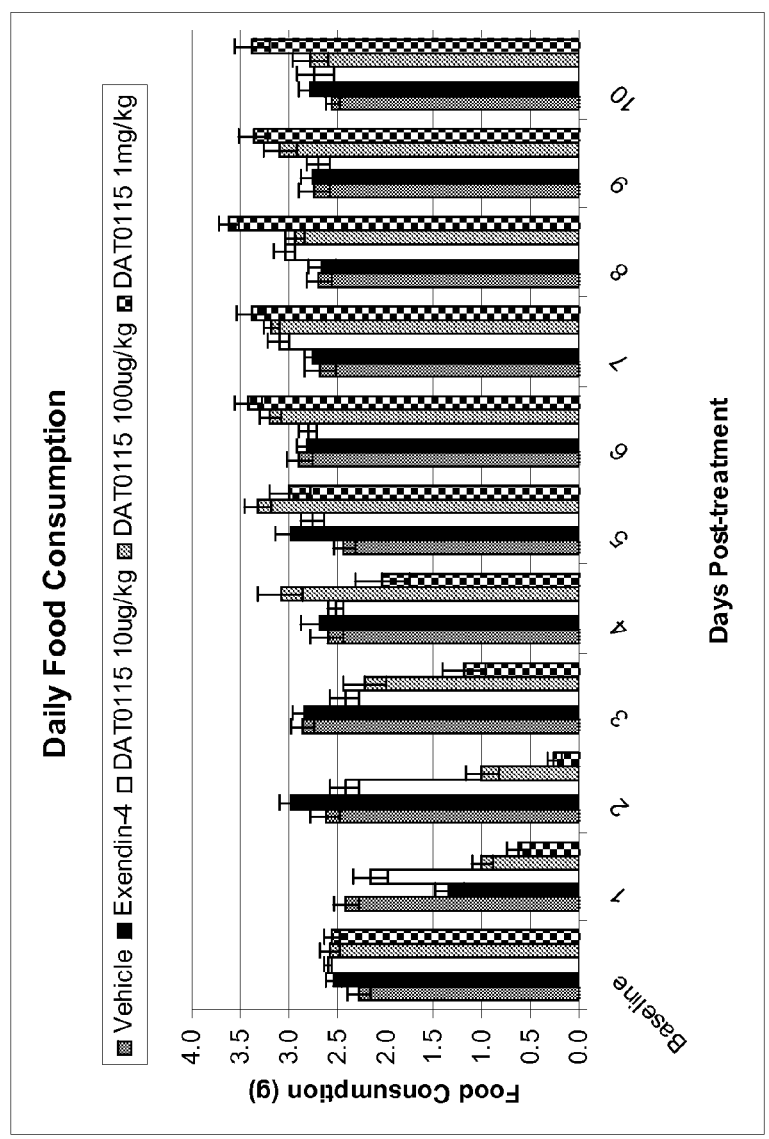

FIG. 4: DSC of DAT0115: Solid line – DAT0115 trace, dotted line – fit to a non-2-state model.
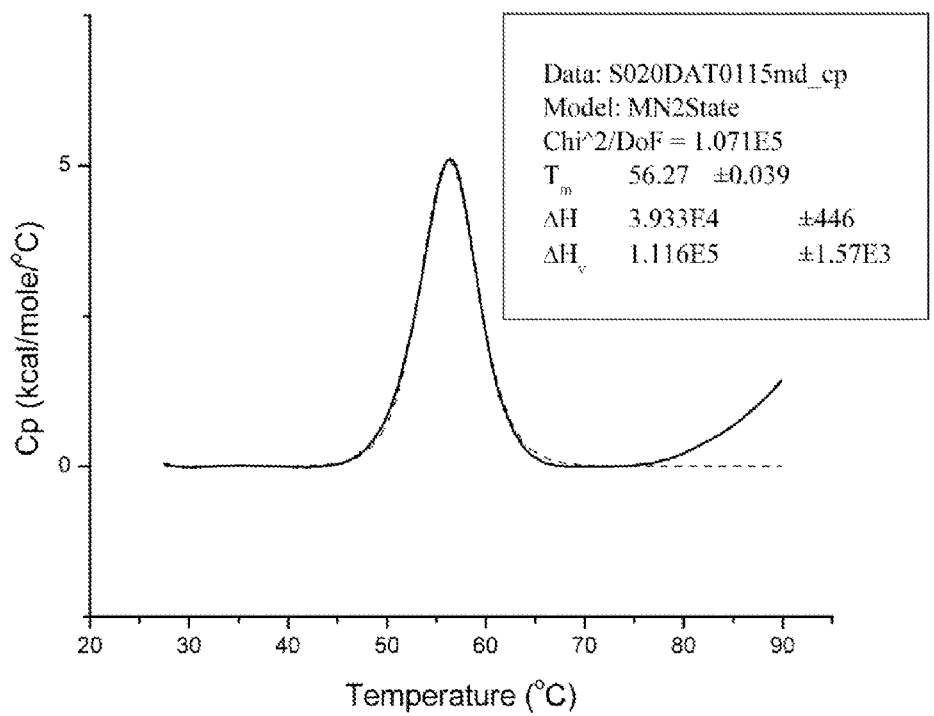

FIG. 5: DSC of Lysozyme: Solid line – lysozyme trace, dotted line – fit to a non-2-state model (traces overlay so dotted trace cannot be seen)
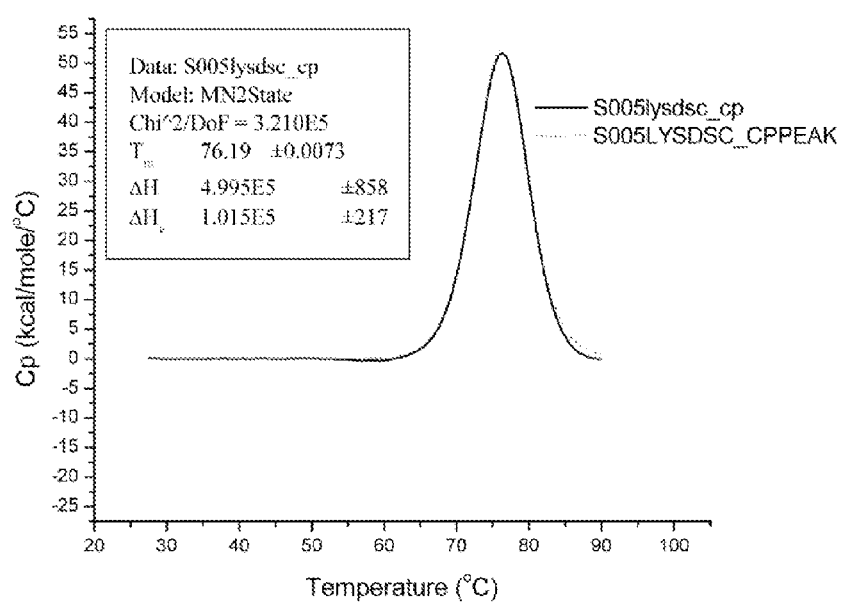

FIG. 6: SEC MALLS of DAT0115
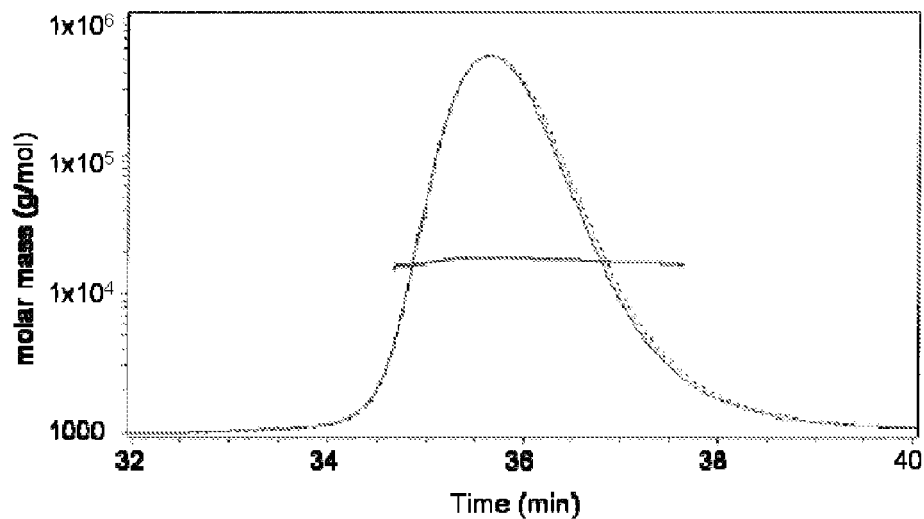
|  | Peak 1 |
|---|---|
| Polydispersity | |
| Mw/Mn | Mw/Mn |
| Mz/Mn | Mz/Mn |
| Molar mass moments (g/mol) | |
| Mn | 1.741e+4 (1%) |
| Mw | 1.743e+4 (1%) |
| Mz | 1.744e+4 (3%) |
| Peak limits (min) | 34.682 - 37.664 |
| Injected mass (g) | 1.0000e-4 |
| Calc. mass (g) | 9.9398e-5 |

FIG. 7: SEC MALLS of DAT0117
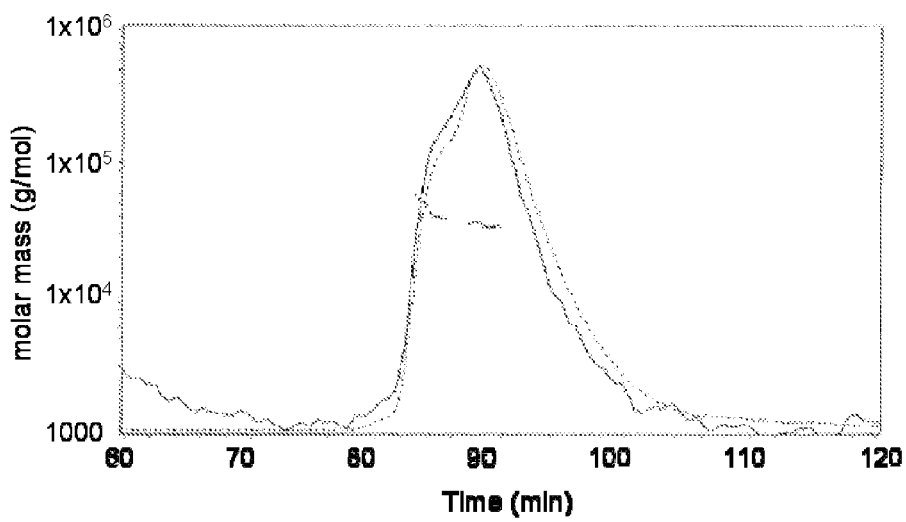
|  | Peak 1 | Peak 2 |
|---|---|---|
| Polydispersity | | |
| Mw/Mn | 1.017(25%) | 1.001(17%) |
| Mz/Mn | 1.037(46%) | 1.003(30%) |
| Molar mass moments (g/mol) | | |
| Mn | 4.378e+4 (17%) | 3.471e+4 (12%) |
| Mw | 4.454e+4 (18%) | 3.475e+4 (12%) |
| Mz | 4.538e+4 (42%) | 3.480e+4 (27%) |
| Peak limits (min) | 8.311 - 8.564 | 8.728 - 8.992 |
| Injected mass (g) | 2.0000e-4 | |
| Calc. mass (g) | 2.2014e-5 | 3.5001e-5 |

FIG. 8: SEC MALLS of DAT0120
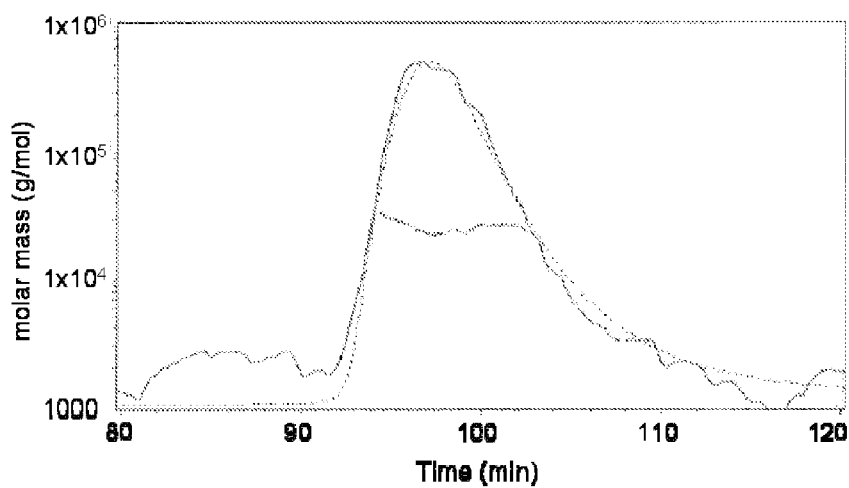
|  | Peak 1 |
|---|---|
| Polydispersity |  |
| Mw/Mn | 1.009(16%) |
| Mz/Mn | 1.019(29%) |
| Molar mass moments (g/mol) |  |
| Mn | 2.532e+4 (11%) |
| Mw | 2.555e+4 (12%) |
| Mz | 2.579e+4 (26%) |
| Peak limits (min) | 9.447-10.272 |
| Injected mass (g) | 1.5500e-4 |
| Calc. mass (g) | 6.3720e-5 |

FIG. 9A: amino acid sequences of leaders (a) ompA (E. coli derived)

MKKTAIAIAVALAGFATVAQA
(SEQ ID NO 34)

(b) ompA-AMA (artificial sequence)

MKKTAIAIAVALAGFATVAMA (artificial sequence)
(SEQ ID NO 35)

(c) ompA-AWA (artificial sequence)

MKKTAIAIAVALAGFATVAWA (artificial sequence)
(SEQ ID NO 36)

(d) ompT (E. coli derived)

MRAKLLGIVLTTPIAISSFA (E. coli)
(SEQ ID NO 37)

(e) ompT-AMA (artificial sequence)

MRAKLLGIVLTTPIAISAMA (artificial sequence)
(SEQ ID NO 38)

FIG. 9B

(f) GAS (S. cerevisiae derived)

MLFKSLSKLATAAAFFAGVATA (S. cerevisiae)
(SEQ ID NO 39)

(g) GAS-AMA (artificial sequence)

MLFKSLSKLATAAAFFAGVAMA (artificial sequence)
(SEQ ID NO 40)

(h) GAS-AWA (artificial sequence)

MLFKSLSKLATAAAFFAGVAWA (artificial sequence)
(SEQ ID NO 41)

(i) Pel B (Erwinia carotovora)

MKYLLPTAAAGLLLLAAQPAMA
(SEQ ID NO 46)

(j) Mal E signal sequence

MKIKTGARILALSALTTMMFSASALA
(SEQ ID NO 49)

FIG. 10: Purified DMS7139 analyzed by mass spectrometry
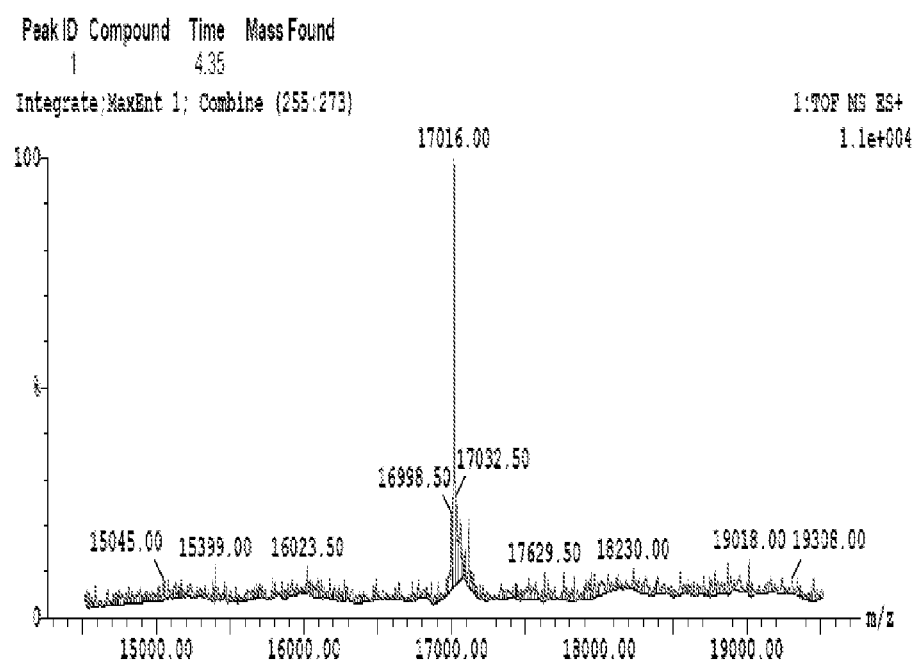

FIG. 11A: An illustration of the statistical significance of blood glucose lowering including comparisons between DAT0115 and control, DMS7139 and control and between DMS7139 and DAT0115, (A) shows study design and (B) graphical representation of glucose AUC.
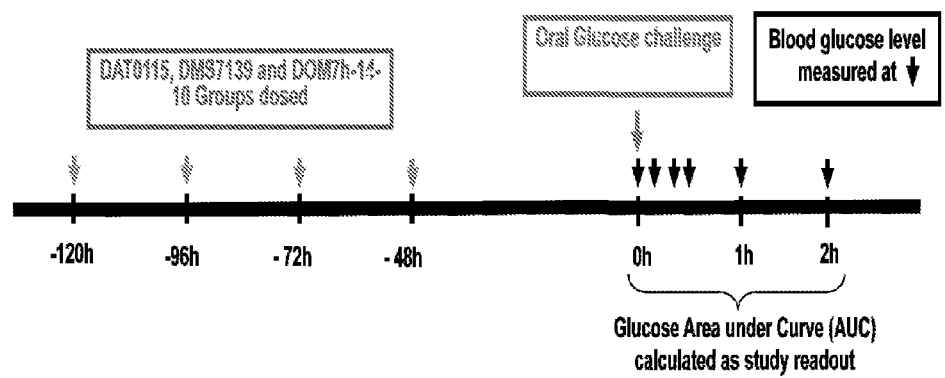

FIG. 11B: An illustration of the statistical significance of blood glucose lowering including comparisons between DAT0115 and control, DMS7139 and control and between DMS7139 and DAT0115, (A) shows study design and (B) graphical representation of glucose AUC.
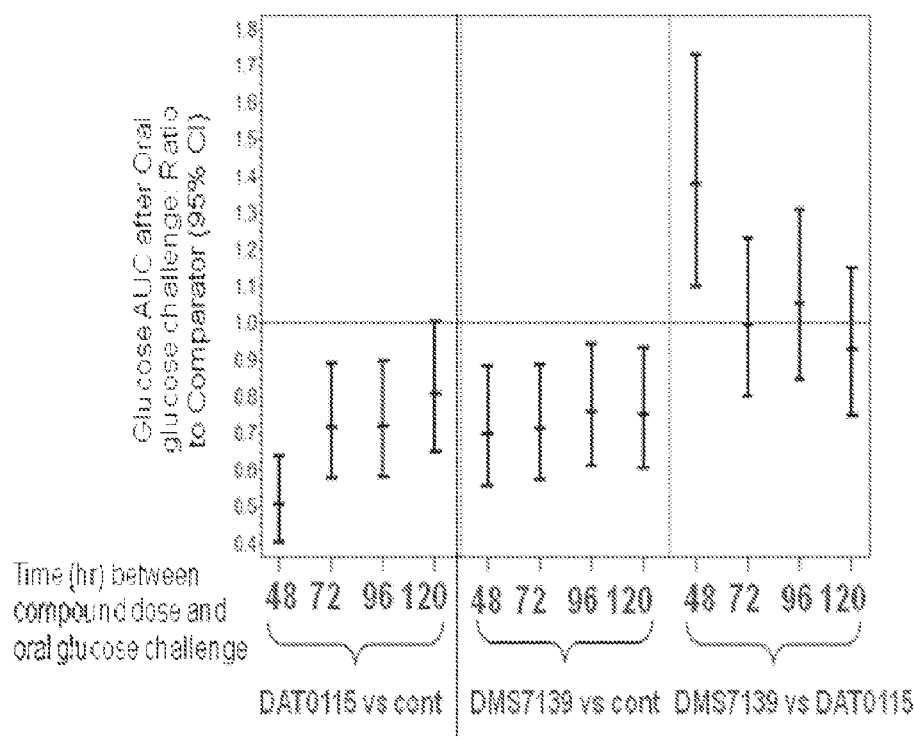

FIG. 12: Repeat dose of DMS7139 shows dose-dependent lowering of HbA1c when compared to DOM7h-14 control.
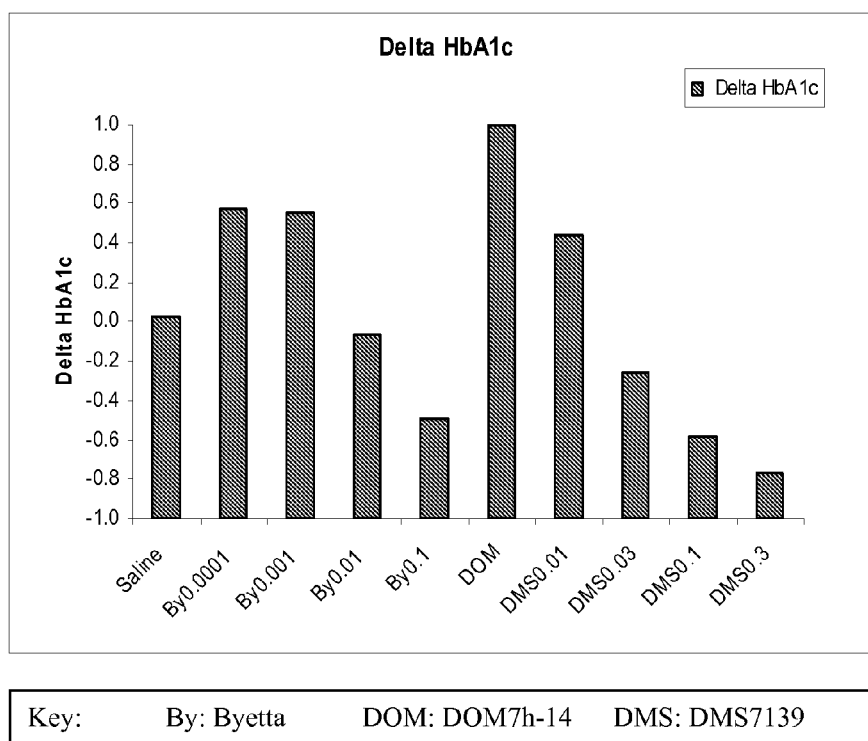

FIG. 13: DAT0115 and DMS7139 show dose dependent reduction in food consumption and body weight compared to the DOM7h-14 control in DIO mouse model of obesity.
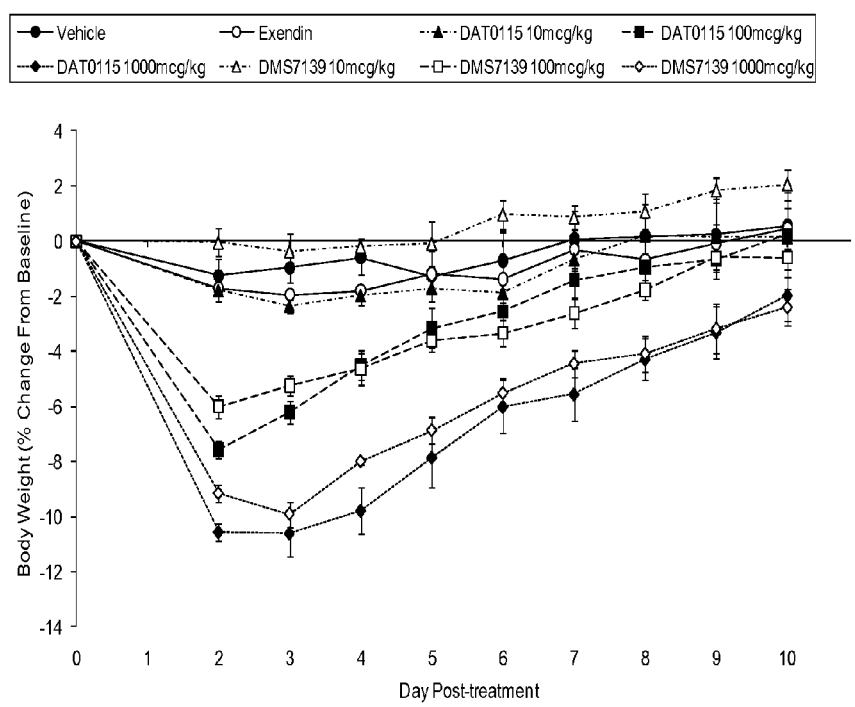

FIG. 14

A peptide conjugate which is:
a Dom7h-14-10 (R108C) albudab conjugated to a C-terminally amidated PYY3-36 via a lysine (introduced at position 10 of PYY) and a 4 repeat PEG linker. The line represents the linker which is covalently attached to the free C terminal cysteine of the Dom7h-14-10 (R108C) AlbudAb and the lysine at position 10 of the PYY sequence. The amino acid sequence and structure of this peptide conjugate is as follows.

diqmtqspsslsasvgdrvtitcrasqwigsqlswyqqkpgkapklllmwrsslqsgvps
rfsgsgsgtdfltlissIqpedfatyycaqgIrhpktfgqgtkveikc

IKPEAPGKDASPEELNRYYASLRHYLNLVTRQRY-NH2

(SEQ ID NO 43)

Where the | denotes the chemical linker

The chemical linker has the following structure:

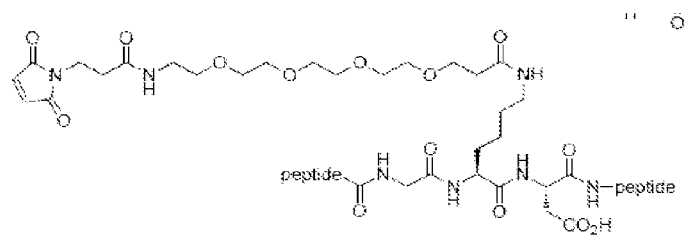

FIG. 15: DMS7605 showed a dose dependent reduction in body weight compared to the vehicle control.
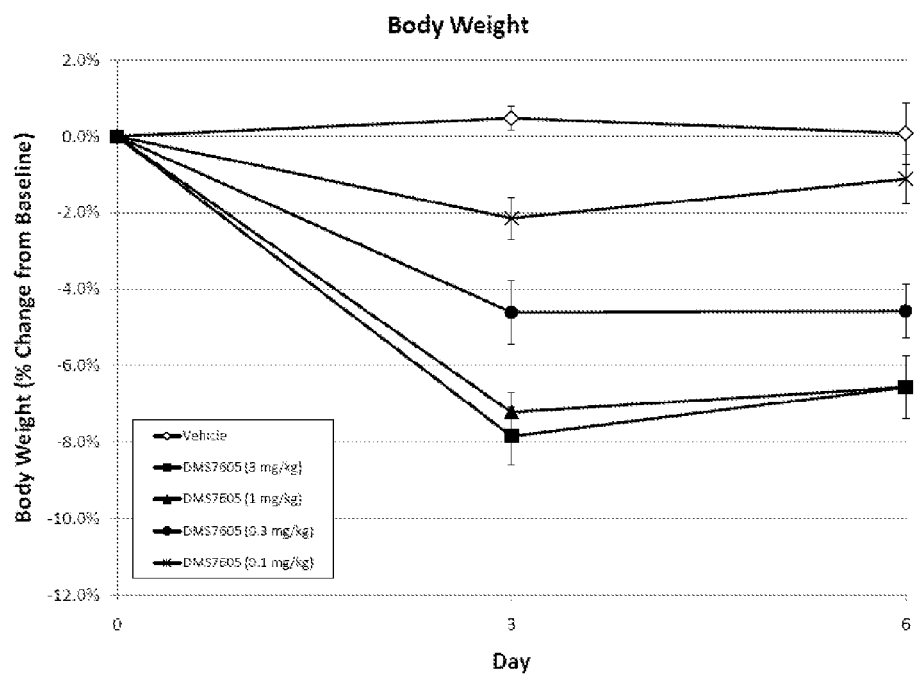

SEQUENCE LISTING

<160> NUMBER OF SEQ ID NOS: 50

<210> SEQ ID NO 1
<211> LENGTH: 168
<212> TYPE: PRT
<213> ORGANISM: Artificial Sequence
<220> FEATURE:
<223> OTHER INFORMATION: 2xGLP-1 A8G DOM7h-14 fusion (DAT0114)

<400> SEQUENCE: 1

```
His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg His Gly
            20                  25                  30

Glu Gly Thr Phe Thr Ser Asp Val Ser Ser Tyr Leu Glu Gly Gln Ala
        35                  40                  45

Ala Lys Glu Phe Ile Ala Trp Leu Val Lys Gly Arg Asp Ile Gln Met
    50                  55                  60
```

```
Thr Gln Ser Pro Ser Ser Leu Ser Ala Ser Val Gly Asp Arg Val Thr
 65                  70                  75                  80

Ile Thr Cys Arg Ala Ser Gln Trp Ile Gly Ser Gln Leu Ser Trp Tyr
                 85                  90                  95

Gln Gln Lys Pro Gly Lys Ala Pro Lys Leu Leu Ile Met Trp Arg Ser
            100                 105                 110

Ser Leu Gln Ser Gly Val Pro Ser Arg Phe Ser Gly Ser Gly Ser Gly
        115                 120                 125

Thr Asp Phe Thr Leu Thr Ile Ser Ser Leu Gln Pro Glu Asp Phe Ala
    130                 135                 140

Thr Tyr Tyr Cys Ala Gln Gly Ala Ala Leu Pro Arg Thr Phe Gly Gln
145                 150                 155                 160

Gly Thr Lys Val Glu Ile Lys Arg
                165

<210> SEQ ID NO 2
<211> LENGTH: 163
<212> TYPE: PRT
<213> ORGANISM: Artificial Sequence
<220> FEATURE:
<223> OTHER INFORMATION: Exendin 4, (G4S)3 linker, DOM7h-14 fusion
      (DAT0115)

<400> SEQUENCE: 2

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30

Ser Gly Ala Pro Pro Pro Ser Gly Gly Gly Gly Ser Gly Gly Gly Gly
         35                  40                  45

Gly Ser Gly Gly Gly Gly Ser Asp Ile Gln Met Thr Gln Ser Pro Ser
     50                  55                  60

Ser Leu Ser Ala Ser Val Gly Asp Arg Val Thr Ile Thr Cys Arg Ala
 65                  70                  75                  80

Ser Gln Trp Ile Gly Ser Gln Leu Ser Trp Tyr Gln Gln Lys Pro Gly
                 85                  90                  95

Lys Ala Pro Lys Leu Leu Ile Met Trp Arg Ser Ser Leu Gln Ser Gly
            100                 105                 110

Val Pro Ser Arg Phe Ser Gly Ser Gly Ser Gly Thr Asp Phe Thr Leu
        115                 120                 125

Thr Ile Ser Ser Leu Gln Pro Glu Asp Phe Ala Thr Tyr Tyr Cys Ala
    130                 135                 140

Gln Gly Ala Ala Leu Pro Arg Thr Phe Gly Gln Gly Thr Lys Val Glu
145                 150                 155                 160

Ile Lys Arg

<210> SEQ ID NO 3
<211> LENGTH: 148
<212> TYPE: PRT
<213> ORGANISM: Artificial Sequence
<220> FEATURE:
<223> OTHER INFORMATION: Exendin 4 DOM7h-14 fusion (DAT0116)

<400> SEQUENCE: 3

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30
```

Ser Gly Ala Pro Pro Ser Gly Asp Ile Gln Met Thr Gln Ser Pro
         35                  40                  45

Ser Ser Leu Ser Ala Ser Val Gly Asp Arg Val Thr Ile Thr Cys Arg
 50                  55                  60

Ala Ser Gln Trp Ile Gly Ser Gln Leu Ser Trp Tyr Gln Gln Lys Pro
 65                  70                  75                  80

Gly Lys Ala Pro Lys Leu Leu Ile Met Trp Arg Ser Ser Leu Gln Ser
                 85                  90                  95

Gly Val Pro Ser Arg Phe Ser Gly Ser Gly Ser Gly Thr Asp Phe Thr
            100                 105                 110

Leu Thr Ile Ser Ser Leu Gln Pro Glu Asp Phe Ala Thr Tyr Tyr Cys
        115                 120                 125

Ala Gln Gly Ala Ala Leu Pro Arg Thr Phe Gly Gln Gly Thr Lys Val
    130                 135                 140

Glu Ile Lys Arg
145

<210> SEQ ID NO 4
<211> LENGTH: 188
<212> TYPE: PRT
<213> ORGANISM: Artificial Sequence
<220> FEATURE:
<223> OTHER INFORMATION: Exendin 4, helical linker, DOM7h-14 fusion
      (DAT0117)

<400> SEQUENCE: 4

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30

Ser Gly Ala Pro Pro Ser Gly Lys Glu Ala Ala Ala Lys Glu Ala
         35                  40                  45

Ala Ala Lys Glu Ala Ala Ala Lys Glu Leu Ala Ala Lys Glu Ala Ala
     50                  55                  60

Ala Lys Glu Ala Ala Ala Lys Glu Ala Ala Ala Lys Glu Leu Ala Ala
 65                  70                  75                  80

Asp Ile Gln Met Thr Gln Ser Pro Ser Ser Leu Ser Ala Ser Val Gly
                 85                  90                  95

Asp Arg Val Thr Ile Thr Cys Arg Ala Ser Gln Trp Ile Gly Ser Gln
            100                 105                 110

Leu Ser Trp Tyr Gln Gln Lys Pro Gly Lys Ala Pro Lys Leu Leu Ile
        115                 120                 125

Met Trp Arg Ser Ser Leu Gln Ser Gly Val Pro Ser Arg Phe Ser Gly
    130                 135                 140

Ser Gly Ser Gly Thr Asp Phe Thr Leu Thr Ile Ser Ser Leu Gln Pro
145                 150                 155                 160

Glu Asp Phe Ala Thr Tyr Tyr Cys Ala Gln Gly Ala Ala Leu Pro Arg
                165                 170                 175

Thr Phe Gly Gln Gly Thr Lys Val Glu Ile Lys Arg
            180                 185

<210> SEQ ID NO 5
<211> LENGTH: 153
<212> TYPE: PRT
<213> ORGANISM: Artificial Sequence
<220> FEATURE:
<223> OTHER INFORMATION: GLP-1 A8G, (G4S)3, linker DOM7h-14 fusion (DAT0118)

<400> SEQUENCE: 5

```
His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly Gly
             20                  25                  30

Gly Gly Ser Gly Gly Gly Gly Ser Gly Gly Gly Ser Asp Ile Gln
         35                  40                  45

Met Thr Gln Ser Pro Ser Ser Leu Ser Ala Ser Val Gly Asp Arg Val
 50                  55                  60

Thr Ile Thr Cys Arg Ala Ser Gln Trp Ile Gly Ser Gln Leu Ser Trp
 65                  70                  75                  80

Tyr Gln Gln Lys Pro Gly Lys Ala Pro Lys Leu Leu Ile Met Trp Arg
                 85                  90                  95

Ser Ser Leu Gln Ser Gly Val Pro Ser Arg Phe Ser Gly Ser Gly Ser
                100                 105                 110

Gly Thr Asp Phe Thr Leu Thr Ile Ser Ser Leu Gln Pro Glu Asp Phe
            115                 120                 125

Ala Thr Tyr Tyr Cys Ala Gln Gly Ala Ala Leu Pro Arg Thr Phe Gly
        130                 135                 140

Gln Gly Thr Lys Val Glu Ile Lys Arg
145                 150
```

<210> SEQ ID NO 6
<211> LENGTH: 142
<212> TYPE: PRT
<213> ORGANISM: Artificial Sequence
<220> FEATURE:
<223> OTHER INFORMATION: GLP-1 A8G, PSS linker, DOM7h-14 fusion
      (DAT0119)

<400> SEQUENCE: 6

```
His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly Pro
             20                  25                  30

Ser Ser Asp Ile Gln Met Thr Gln Ser Pro Ser Ser Leu Ser Ala Ser
         35                  40                  45

Val Gly Asp Arg Val Thr Ile Thr Cys Arg Ala Ser Gln Trp Ile Gly
 50                  55                  60

Ser Gln Leu Ser Trp Tyr Gln Gln Lys Pro Gly Lys Ala Pro Lys Leu
 65                  70                  75                  80

Leu Ile Met Trp Arg Ser Ser Leu Gln Ser Gly Val Pro Ser Arg Phe
             85                  90                  95

Ser Gly Ser Gly Ser Gly Thr Asp Phe Thr Leu Thr Ile Ser Ser Leu
            100                 105                 110

Gln Pro Glu Asp Phe Ala Thr Tyr Tyr Cys Ala Gln Gly Ala Ala Leu
        115                 120                 125

Pro Arg Thr Phe Gly Gln Gly Thr Lys Val Glu Ile Lys Arg
    130                 135                 140
```

<210> SEQ ID NO 7
<211> LENGTH: 179
<212> TYPE: PRT
<213> ORGANISM: Artificial Sequence
<220> FEATURE:
<223> OTHER INFORMATION: GLP-1 A8G, helical linker, DOM7h-14 fusion (DAT0120)

<400> SEQUENCE: 7

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Lys
            20                  25                  30

Glu Ala Ala Ala Lys Glu Ala Ala Ala Lys Glu Ala Ala Ala Lys Glu
        35                  40                  45

Leu Ala Ala Lys Glu Ala Ala Ala Lys Glu Ala Ala Ala Lys Glu Ala
50                  55                  60

Ala Ala Lys Glu Leu Ala Ala Asp Ile Gln Met Thr Gln Ser Pro Ser
65                  70                  75                  80

Ser Leu Ser Ala Ser Val Gly Asp Arg Val Thr Ile Thr Cys Arg Ala
                85                  90                  95

Ser Gln Trp Ile Gly Ser Gln Leu Ser Trp Tyr Gln Gln Lys Pro Gly
            100                 105                 110

Lys Ala Pro Lys Leu Leu Ile Met Trp Arg Ser Ser Leu Gln Ser Gly
        115                 120                 125

Val Pro Ser Arg Phe Ser Gly Ser Gly Thr Asp Phe Thr Leu
130                 135                 140

Thr Ile Ser Ser Leu Gln Pro Glu Asp Phe Ala Thr Tyr Tyr Cys Ala
145                 150                 155                 160

Gln Gly Ala Ala Leu Pro Arg Thr Phe Gly Gln Gly Thr Lys Val Glu
                165                 170                 175

Ile Lys Arg

<210> SEQ ID NO 8
<211> LENGTH: 108
<212> TYPE: PRT
<213> ORGANISM: Artificial Sequence
<220> FEATURE:
<223> OTHER INFORMATION: DOM7h-14

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Lys Leu Leu Ile
        35                  40                  45

Met Trp Arg Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Ala Ala Leu Pro Arg
                85                  90                  95

Thr Phe Gly Gln Gly Thr Lys Val Glu Ile Lys Arg
            100                 105

<210> SEQ ID NO 9
<211> LENGTH: 31
<212> TYPE: PRT
<213> ORGANISM: Artificial Sequence
<220> FEATURE:
<223> OTHER INFORMATION: GLP-1 (7-37) A8G

<400> SEQUENCE: 9

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 10
<211> LENGTH: 39
<212> TYPE: PRT
<213> ORGANISM: Artificial Sequence
<220> FEATURE:
<223> OTHER INFORMATION: exendin-4

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 11
<211> LENGTH: 40
<212> TYPE: PRT
<213> ORGANISM: Artificial Sequence
<220> FEATURE:
<223> OTHER INFORMATION: helical linker

<400> SEQUENCE: 11

Lys Glu Ala Ala Ala Lys Glu Ala Ala Ala Lys Glu Ala Ala Ala Lys
1               5                   10                  15

Glu Leu Ala Ala Lys Glu Ala Ala Ala Lys Glu Ala Ala Ala Lys Glu
            20                  25                  30

Ala Ala Ala Lys Glu Leu Ala Ala
        35                  40

<210> SEQ ID NO 12
<211> LENGTH: 16
<212> TYPE: PRT
<213> ORGANISM: Artificial Sequence
<220> FEATURE:
<223> OTHER INFORMATION: Gly-ser linker

<400> SEQUENCE: 12

Gly Gly Gly Gly Gly Ser Gly Gly Gly Gly Ser Gly Gly Gly Gly Ser
1               5                   10                  15

<210> SEQ ID NO 13
<211> LENGTH: 504
<212> TYPE: DNA
<213> ORGANISM: Artificial Sequence
<220> FEATURE:
<223> OTHER INFORMATION: DAT0114 - nucleic acid sequence (from mammalian
      construct)

<400> SEQUENCE: 13
catggtgaag ggacctttac cagtgatgta agttcttatt tggaaggcca agctgccaag      60
gaattcattg cttggctggt gaaaggccga catggtgaag ggacctttac cagtgatgta     120
agttcttatt tggaaggcca agctgccaag gaattcattg cttggctggt gaaaggccga     180
gacatccaga tgacccagtc tccatcctcc ctgtctgcat ctgtaggaga ccgtgtcacc     240
atcacttgcc gggcaagtca gtggattggg tctcagttat cttggtacca gcagaaacca     300

```
gggaaagccc ctaagctcct gatcatgtgg cgttcctcgt tgcaaagtgg ggtcccatca    360
cgtttcagtg gcagtggatc tgggacagat tcactctca ccatcagcag tctgcaacct    420
gaagattttg ctacgtacta ctgtgctcag ggtgcggcgt tgcctaggac gttcggccaa    480
gggaccaagg tggaaatcaa acgg                                          504
```

<210> SEQ ID NO 14
<211> LENGTH: 489
<212> TYPE: DNA
<213> ORGANISM: Artificial Sequence
<220> FEATURE:
<223> OTHER INFORMATION: DAT0115 - nucleic acid sequence (from mammalian construct)

<400> SEQUENCE: 14

```
catggtgaag gaacatttac cagtgacttg tcaaaacaga tggaagagga ggcagtgcgg    60
ttatttattg agtggcttaa gaacggagga ccaagtagcg gggcacctcc gccatcgggt    120
ggtggaggcg gttcaggcgg aggtggcagc ggcggtggcg gtcggacat ccagatgacc    180 cagtctccat cctccctgtc tgcatctgta ggagaccgtg tcaccatcac ttgccgggca    240
agtcagtgga ttgggtctca gttatcttgg taccagcaga aaccagggaa agcccctaag    300
ctcctgatca tgtggcgttc ctcgttgcaa agtggggtcc catcacgttt cagtggcagt    360
ggatctggga cagatttcac tctcaccatc agcagtctgc aacctgaaga ttttgctacg    420
tactactgtg ctcagggtgc ggcgttgcct aggacgttcg gccagggag caaggtggaa    480 atcaaacgg                                                            489
```

<210> SEQ ID NO 15
<211> LENGTH: 495
<212> TYPE: DNA
<213> ORGANISM: Artificial Sequence
<220> FEATURE:
<223> OTHER INFORMATION: DAT0115 - nucleic acid sequence (from E.coli construct)

<400> SEQUENCE: 15

```
cacggtgaag gtaccttcac ctctgacctg agcaaacaga tggaggaaga agcggttcgt    60
ctgttcatcg agtggctgaa aaacggtggt ccgtcttctg gtgctccgcc accgtctggt    120
ggtggtggtg gttctggtgg tggtggttct ggtggtggcg gtagcgacat ccagatgact    180
cagtccccaa gctctctgtc tgcctccgtt ggcgatcgtg ttacgatcac gtgccgtgct    240
tctcagtgga tcggttccca gctgtcctgg tatcagcaga aaccgggcaa agccccgaaa    300
ctcctgatca tgtggcgtag ctctctgcag tctggtgtac cgagccgctt ctctggttct    360
ggttctggta ccgacttcac cctgaccatt tcctctctgc agccggaaga tttcgcgacc    420
tactactgtg ctcagggtgc ggcactgcca cgtacttttg gccagggtac gaaagtcgag    480
attaaacgtt aatga                                                     495
```

<210> SEQ ID NO 16
<211> LENGTH: 444
<212> TYPE: DNA
<213> ORGANISM: Artificial Sequence
<220> FEATURE:
<223> OTHER INFORMATION: DAT0116 - nucleic acid sequence (from mammalian construct)

<400> SEQUENCE: 16

```
catggtgaag gaacatttac cagtgacttg tcaaaacaga tggaagagga ggcagtgcgg    60
```

```
ttatttattg agtggcttaa gaacggagga ccaagtagcg gggcacctcc gccatcgggt        120
gacatccaga tgacccagtc tccatcctcc ctgtctgcat ctgtaggaga ccgtgtcacc        180
atcacttgcc gggcaagtca gtggattggg tctcagttat cttggtacca gcagaaacca        240
gggaaagccc ctaagctcct gatcatgtgg cgttcctcgt tgcaaagtgg ggtcccatca        300
cgtttcagtg gcagtggatc tgggacagat ttcactctca ccatcagcag tctgcaacct        360
gaagattttg ctacgtacta ctgtgctcag ggtgcggcgt tgcctaggac gttcggccaa        420
gggaccaagg tggaaatcaa acgg                                              444
```

<210> SEQ ID NO 17
<211> LENGTH: 447
<212> TYPE: DNA
<213> ORGANISM: Artificial Sequence
<220> FEATURE:
<223> OTHER INFORMATION: DAT0116 - nucleic acid sequence (from E.coli construct)

<400> SEQUENCE: 17

```
cacggtgaag gtaccttcac ctctgacctg agcaaacaga tggaggaaga agcggttcgt        60
ctgttcatcg agtggctgaa aaacggtggt ccgtcttctg gtgctccgcc accgtctgac       120
atccagatga ctcagtcccc aagctctctg tctgcctccg ttggcgatcg tgttacgatc       180
acgtgccgtg cttctcagtg gatcggttcc cagctgtcct ggtatcagca gaaaccgggc      240
aaagccccga actcctgat catgtggcgt agctctctgc agtctggtgt accgagccgc       300
ttctctggtt ctggttctgg taccgacttc accctgacca tttcctctct gcagccggaa       360
gatttcgcga cctactactg tgctcagggt gcggcactgc cacgtacttt tggccagggt       420
acgaaagtcg agattaaacg ttaatga                                           447
```

<210> SEQ ID NO 18
<211> LENGTH: 564
<212> TYPE: DNA
<213> ORGANISM: Artificial Sequence
<220> FEATURE:
<223> OTHER INFORMATION: DAT0117 - nucleic acid sequence (from mammalian construct)

<400> SEQUENCE: 18

```
catggtgaag gaacatttac cagtgacttg tcaaaacaga tggaagagga ggcagtgcgg        60
ttatttattg agtggcttaa gaacggagga ccaagtagcg gggcacctcc gccatcgggt       120
aaagaagcgg cggcgaaaga agcggcggcg aaagaagcgg cggcgaaaga attggccgca       180
aaagaagcgg cggcgaaaga agcggcggcg aaagaagcgg cggcgaaaga attggccgca       240
gacatccaga tgacccagtc tccatcctcc ctgtctgcat ctgtaggaga ccgtgtcacc       300
atcacttgcc gggcaagtca gtggattggg tctcagttat cttggtacca gcagaaacca       360
gggaaagccc ctaagctcct gatcatgtgg cgttcctcgt tgcaaagtgg ggtcccatca       420
cgtttcagtg gcagtggatc tgggacagat ttcactctca ccatcagcag tctgcaacct       480
gaagattttg ctacgtacta ctgtgctcag ggtgcggcgt tgcctaggac gttcggccaa       540
gggaccaagg tggaaatcaa acgg                                              564
```

<210> SEQ ID NO 19
<211> LENGTH: 567
<212> TYPE: DNA
<213> ORGANISM: Artificial Sequence
<220> FEATURE:
<223> OTHER INFORMATION: DAT0117 - nucleic acid sequence (from E.coli construct)

<400> SEQUENCE: 19

```
cacggtgaag gtaccttcac ctctgacctg agcaaacaga tggaggaaga agcggttcgt      60
ctgttcatcg agtggctgaa aaacggtggt ccgtcttctg gtgctccgcc accgtctaaa     120
gaagcggcgg cgaaagaagc ggcggcgaaa gaagcggcgg cgaaagaatt ggccgcaaaa     180
gaagcggcgg cgaaagaagc ggcggcgaaa gaagcggcgg cgaaagaatt ggccgcagac     240
atccagatga ctcagtcccc aagctctctg tctgcctccg ttggcgatcg tgttacgatc     300
acgtgccgtg cttctcagtg gatcggttcc cagctgtcct ggtatcagca gaaaccgggc     360
aaagccccga actcctgat  catgtggcgt agctctctgc agtctggtgt accgagccgc     420
ttctctggtt ctggttctgg taccgacttc accctgacca tttcctctct gcagccggaa     480
gatttcgcga cctactactg tgctcagggt gcggcactgc cacgtacttt tggccagggt     540
acgaaagtcg agattaaacg ttaatga                                         567
```

<210> SEQ ID NO 20
<211> LENGTH: 459
<212> TYPE: DNA
<213> ORGANISM: Artificial Sequence
<220> FEATURE:
<223> OTHER INFORMATION: DAT0118 - nucleic acid sequence (from mammalian construct)

<400> SEQUENCE: 20

```
catggtgaag gacctttac  cagtgatgta agttcttatt tggaaggcca agctgccaag      60
gaattcattg cttggctggt gaaaggccga ggtggaggcg gttcaggcgg aggtggcagc     120
ggcggtggcg ggtcggacat ccagatgacc cagtctccat cctccctgtc tgcatctgta     180
ggagaccgtg tcaccatcac ttgccgggca agtcagtgga ttgggtctca gttatcttgg     240
taccagcaga aaccagggaa agcccctaag ctcctgatca tgtggcgttc ctcgttgcaa     300
agtggggtcc catcacgttt cagtggcagt ggatctggga cagatttcac tctcaccatc     360
agcagtctgc aacctgaaga ttttgctacg tactactgtg ctcagggtgc ggcgttgcct     420
aggacgttcg gccaagggac caaggtggaa atcaaacgg                            459
```

<210> SEQ ID NO 21
<211> LENGTH: 426
<212> TYPE: DNA
<213> ORGANISM: Artificial Sequence
<220> FEATURE:
<223> OTHER INFORMATION: DAT0119 - nucleic acid sequence (from mammalian construct)

<400> SEQUENCE: 21

```
catggtgaag gacctttac  cagtgatgta agttcttatt tggaaggcca agctgccaag      60
gaattcattg cttggctggt gaaaggccga ggaccaagct cggacatcca gatgacccag     120
tctccatcct ccctgtctgc atctgtagga gaccgtgtca ccatcacttg ccgggcaagt     180
cagtggattg gtctcagtt  atcttggtac cagcagaaac cagggaaagc ccctaagctc     240
ctgatcatgt ggcgttcctc gttgcaaagt ggggtcccat cacgtttcag tggcagtgga     300
tctgggacag atttcactct caccatcagc agtctgcaac ctgaagattt tgctacgtac     360
tactgtgctc agggtgcggc gttgcctagg acgttcggcc aagggaccaa ggtggaaatc     420
aaacgg                                                                426
```

<210> SEQ ID NO 22
<211> LENGTH: 537
<212> TYPE: DNA
<213> ORGANISM: Artificial Sequence
<220> FEATURE:
<223> OTHER INFORMATION: DAT0120 - nucleic acid sequence (from mammalian construct)

<400> SEQUENCE: 22

```
catggtgaag ggacctttac cagtgatgta agttcttatt tggaaggcca agctgccaag    60
gaattcattg cttggctggt gaaaggccga ggaaaagaag cggcggcgaa agaagcggcg   120
gcgaaagaag cggcggcgaa agaattggcc gcaaaagaag cggcggcgaa agaagcggcg   180
gcgaaagaag cggcggcgaa agaattggcc gcagacatcc agatgaccca gtctccatcc   240
tccctgtctg catctgtagg accgtgtc accatcactt gccgggcaag tcagtggatt     300
gggtctcagt tatcttggta ccagcagaaa ccagggaaag cccctaagct cctgatcatg   360
tggcgttcct cgttgcaaag tggggtccca tcacgtttca gtggcagtgg atctgggaca   420
gatttcactc tcaccatcag cagtctgcaa cctgaagatt ttgctacgta ctactgtgct   480
cagggtgcgg cgttgcctag gacgttcggc caagggacca aggtggaaat caaacgg     537
```

<210> SEQ ID NO 23
<211> LENGTH: 324
<212> TYPE: DNA
<213> ORGANISM: Artificial Sequence
<220> FEATURE:
<223> OTHER INFORMATION: Dom7h-14 - nucleic acid sequence

<400> SEQUENCE: 23

```
gacatccaga tgacccagtc tccatcctcc ctgtctgcat ctgtaggaga ccgtgtcacc    60
atcacttgcc gggcaagtca gtggattggg tctcagttat cttggtacca gcagaaacca   120
gggaaagccc ctaagctcct gatcatgtgg cgttcctcgt tgcaaagtgg ggtcccatca   180
cgtttcagtg gcagtggatc tgggacagat tcactctca ccatcagcag tctgcaacct    240
gaagattttg ctacgtacta ctgtgctcag ggtgcggcgt tgcctaggac gttcggccaa   300
gggaccaagg tggaaatcaa acgg                                          324
```

<210> SEQ ID NO 24
<211> LENGTH: 163
<212> TYPE: PRT
<213> ORGANISM: Artificial Sequence
<220> FEATURE:
<223> OTHER INFORMATION: Exendin 4, (G4S)3, linker DOM7h-14-10 fusion (DMS7139)

<400> SEQUENCE: 24

```
His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Gly Ser Gly Gly Gly
        35                  40                  45

Gly Ser Gly Gly Gly Gly Ser Asp Ile Gln Met Thr Gln Ser Pro Ser
    50                  55                  60

Ser Leu Ser Ala Ser Val Gly Asp Arg Val Thr Ile Thr Cys Arg Ala
65                  70                  75                  80

Ser Gln Trp Ile Gly Ser Gln Leu Ser Trp Tyr Gln Gln Lys Pro Gly
                85                  90                  95
```

```
Lys Ala Pro Lys Leu Leu Ile Met Trp Arg Ser Ser Leu Gln Ser Gly
            100                 105                 110

Val Pro Ser Arg Phe Ser Gly Ser Gly Ser Gly Thr Asp Phe Thr Leu
            115                 120                 125

Thr Ile Ser Ser Leu Gln Pro Glu Asp Phe Ala Thr Tyr Tyr Cys Ala
            130                 135                 140

Gln Gly Leu Arg His Pro Lys Thr Phe Gly Gln Gly Thr Lys Val Glu
145                 150                 155                 160

Ile Lys Arg

<210> SEQ ID NO 25
<211> LENGTH: 163
<212> TYPE: PRT
<213> ORGANISM: Artificial Sequence
<220> FEATURE:
<223> OTHER INFORMATION: Exendin 4, (G4S)3, linker DOM7h-11-15 fusion
      (DMS7143)

<400> SEQUENCE: 25

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Gly Ser Gly Gly Gly Gly
        35                  40                  45

Gly Ser Gly Gly Gly Gly Ser Asp Ile Gln Met Thr Gln Ser Pro Ser
    50                  55                  60

Ser Leu Ser Ala Ser Val Gly Asp Arg Val Thr Ile Thr Cys Arg Ala
65                  70                  75                  80

Ser Arg Pro Ile Gly Thr Met Leu Ser Trp Tyr Gln Gln Lys Pro Gly
                85                  90                  95

Lys Ala Pro Lys Leu Leu Ile Leu Ala Phe Ser Arg Leu Gln Ser Gly
            100                 105                 110

Val Pro Ser Arg Phe Ser Gly Ser Gly Ser Gly Thr Asp Phe Thr Leu
            115                 120                 125

Thr Ile Ser Ser Leu Gln Pro Glu Asp Phe Ala Thr Tyr Tyr Cys Ala
            130                 135                 140

Gln Ala Gly Thr His Pro Thr Thr Phe Gly Gln Gly Thr Lys Val Glu
145                 150                 155                 160

Ile Lys Arg

<210> SEQ ID NO 26
<211> LENGTH: 108
<212> TYPE: PRT
<213> ORGANISM: Artificial Sequence
<220> FEATURE:
<223> OTHER INFORMATION: DOM7h-14-10

<400> SEQUENCE: 26

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Lys Leu Leu Ile
        35                  40                  45

Met Trp Arg Ser Ser Leu Gln Ser Gly Val Pro Ser Arg Phe Ser Gly
    50                  55                  60
```

-continued

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Gly Leu Arg His Pro Lys
                 85                  90                  95

Thr Phe Gly Gln Gly Thr Lys Val Glu Ile Lys Arg
            100                 105

<210> SEQ ID NO 27
<211> LENGTH: 108
<212> TYPE: PRT
<213> ORGANISM: Artificial Sequence
<220> FEATURE:
<223> OTHER INFORMATION: DOM7h-11-15

<400> SEQUENCE: 27

Asp Ile Gln Met Thr Gln Ser Pro Ser Ser Leu Ser Ala Ser Val Gly
 1               5                  10                  15

Asp Arg Val Thr Ile Thr Cys Arg Ala Ser Arg Pro Ile Gly Thr Met
                20                  25                  30

Leu Ser Trp Tyr Gln Gln Lys Pro Gly Lys Ala Pro Lys Leu Leu Ile
             35                  40                  45

Leu Ala Phe Ser Arg Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Ala Gly Thr His Pro Thr
                 85                  90                  95

Thr Phe Gly Gln Gly Thr Lys Val Glu Ile Lys Arg
            100                 105

<210> SEQ ID NO 28
<211> LENGTH: 20
<212> TYPE: PRT
<213> ORGANISM: Artificial Sequence
<220> FEATURE:
<223> OTHER INFORMATION: OmpT AWA signal peptide (leader)

<400> SEQUENCE: 28

Met Arg Ala Lys Leu Leu Gly Ile Val Leu Thr Thr Pro Ile Ala Ile
 1               5                  10                  15

Ser Ala Trp Ala
            20

<210> SEQ ID NO 29
<211> LENGTH: 489
<212> TYPE: DNA
<213> ORGANISM: Artificial Sequence
<220> FEATURE:
<223> OTHER INFORMATION: Exendin 4, (G4S)3, linker DOM7h-14-10 fusion
      (DMS7139)

<400> SEQUENCE: 29
catggtgaag gaacatttac cagtgacttg tcaaaacaga tggaagagga ggcagtgcgg      60
ttatttattg agtggcttaa gaacggagga ccaagtagcg gggcacctcc gccatcgggt     120
ggtggaggcg gttcaggcgg aggtggcagc ggcggtggcg gtcgacat ccagatgacc      180 cagtctccat cctccctgtc tgcatctgta ggagaccgtg tcaccatcac ttgccgggca     240
agtcagtgga ttgggtctca gttatcttgg taccagcaga aaccagggaa agcccctaag     300
ctcctgatca tgtggcgttc ctcgttgcaa agtggggtcc catcacgttt cagtggcagt     360
```

```
ggatctggga cagatttcac tctcaccatc agcagtctgc aacctgaaga ttttgctacg    420
tactactgtg ctcagggttt gaggcatcct aagacgttcg ccaagggac caaggtggaa    480 atcaaacgg                                                          489

<210> SEQ ID NO 30
<211> LENGTH: 489
<212> TYPE: DNA
<213> ORGANISM: Artificial Sequence
<220> FEATURE:
<223> OTHER INFORMATION: Exendin 4, (G4S)3, linker DOM7h-11-115 fusion
      (DMS7143)

<400> SEQUENCE: 30
catggtgaag gaacatttac cagtgacttg tcaaaacaga tggaagagga ggcagtgcgg    60
ttatttattg agtggcttaa gaacggagga ccaagtagcg gggcacctcc gccatcgggt   120
ggtggaggcg gttcaggcgg aggtggcagc ggcggtggcg gtcggacat ccagatgacc   180 cagtctccat cctccctgtc tgcatctgta ggagaccgtg tcaccatcac ttgccgggca   240
agtcgtccga ttgggacgat gttaagttgg taccagcaga accagggaa agcccctaag   300 ctcctgatcc ttgcttttc ccgtttgcaa agtggggtcc catcacgttt cagtggcagt   360
ggatctggga cagatttcac tctcaccatc agcagtctgc aacctgaaga ttttgctacg   420
tactactgcg cgcaggctgg gacgcatcct acgacgttcg ccaagggac caaggtggaa   480 atcaaacgg                                                          489

<210> SEQ ID NO 31
<211> LENGTH: 324
<212> TYPE: DNA
<213> ORGANISM: Artificial Sequence
<220> FEATURE:
<223> OTHER INFORMATION: Dom7h-14-10  - nucleic acid

<400> SEQUENCE: 31
gacatccaga tgacccagtc tccatcctcc ctgtctgcat ctgtaggaga ccgtgtcacc    60
atcacttgcc gggcaagtca gtggattggg tctcagttat cttggtacca gcagaaacca   120
gggaaagccc ctaagctcct gatcatgtgg cgttcctcgt tgcaaagtgg ggtcccatca   180
cgtttcagtg gcagtggatc tgggacagat tcactctca ccatcagcag tctgcaacct   240
gaagattttg ctacgtacta ctgtgctcag ggtttgaggc atcctaagac gttcggccaa   300
gggaccaagg tggaaatcaa acgg                                         324

<210> SEQ ID NO 32
<211> LENGTH: 324
<212> TYPE: DNA
<213> ORGANISM: Artificial Sequence
<220> FEATURE:
<223> OTHER INFORMATION: Dom7h-11-15  - nucleic acid

<400> SEQUENCE: 32
gacatccaga tgacccagtc tccatcctcc ctgtctgcat ctgtaggaga ccgtgtcacc    60
atcacttgcc gggcaagtcg tccgattggg acgatgttaa gttggtacca gcagaaacca   120
gggaaagccc ctaagctcct gatccttgct ttttccgtt tgcaaagtgg ggtcccatca   180
cgtttcagtg gcagtggatc tgggacagat tcactctca ccatcagcag tctgcaacct   240
gaagattttg ctacgtacta ctgcgcgcag gctgggacgc atcctacgac gttcggccaa   300
gggaccaagg tggaaatcaa acgg                                         324
```

<210> SEQ ID NO 33
<211> LENGTH: 60
<212> TYPE: DNA
<213> ORGANISM: Artificial Sequence
<220> FEATURE:
<223> OTHER INFORMATION: OmpAWA signal peptide - nucleic acid sequence

<400> SEQUENCE: 33
atgcgggcga aactcctagg aatagtcctg acaaccccta tcgcgatcag cgcttgggcc    60

<210> SEQ ID NO 34
<211> LENGTH: 21
<212> TYPE: PRT
<213> ORGANISM: Artificial Sequence
<220> FEATURE:
<223> OTHER INFORMATION: ompA (E. coli derived)

<400> SEQUENCE: 34

Met Lys Lys Thr Ala Ile Ala Ile Ala Val Ala Leu Ala Gly Phe Ala
1               5                   10                  15

Thr Val Ala Gln Ala
            20

<210> SEQ ID NO 35
<211> LENGTH: 21
<212> TYPE: PRT
<213> ORGANISM: Artificial Sequence
<220> FEATURE:
<223> OTHER INFORMATION: ompA-AMA (artificial sequence)

<400> SEQUENCE: 35

Met Lys Lys Thr Ala Ile Ala Ile Ala Val Ala Leu Ala Gly Phe Ala
1               5                   10                  15

Thr Val Ala Met Ala
            20

<210> SEQ ID NO 36
<211> LENGTH: 21
<212> TYPE: PRT
<213> ORGANISM: Artificial Sequence
<220> FEATURE:
<223> OTHER INFORMATION: ompA-AWA

<400> SEQUENCE: 36

Met Lys Lys Thr Ala Ile Ala Ile Ala Val Ala Leu Ala Gly Phe Ala
1               5                   10                  15

Thr Val Ala Trp Ala
            20

<210> SEQ ID NO 37
<211> LENGTH: 20
<212> TYPE: PRT
<213> ORGANISM: Artificial Sequence
<220> FEATURE:
<223> OTHER INFORMATION: ompT (E. coli derived)

<400> SEQUENCE: 37

Met Arg Ala Lys Leu Leu Gly Ile Val Leu Thr Thr Pro Ile Ala Ile
1               5                   10                  15

Ser Ser Phe Ala
            20

<210> SEQ ID NO 38
<211> LENGTH: 20

```
<212> TYPE: PRT
<213> ORGANISM: Artificial Sequence
<220> FEATURE:
<223> OTHER INFORMATION: ompT-AMA

<400> SEQUENCE: 38

Met Arg Ala Lys Leu Leu Gly Ile Val Leu Thr Thr Pro Ile Ala Ile
1               5                   10                  15

Ser Ala Met Ala
            20

<210> SEQ ID NO 39
<211> LENGTH: 22
<212> TYPE: PRT
<213> ORGANISM: Artificial Sequence
<220> FEATURE:
<223> OTHER INFORMATION: GAS  (S. cerevisiae derived)

<400> SEQUENCE: 39

Met Leu Phe Lys Ser Leu Ser Lys Leu Ala Thr Ala Ala Ala Phe Phe
1               5                   10                  15

Ala Gly Val Ala Thr Ala
            20

<210> SEQ ID NO 40
<211> LENGTH: 22
<212> TYPE: PRT
<213> ORGANISM: Artificial Sequence
<220> FEATURE:
<223> OTHER INFORMATION: GAS-AMA

<400> SEQUENCE: 40

Met Leu Phe Lys Ser Leu Ser Lys Leu Ala Thr Ala Ala Ala Phe Phe
1               5                   10                  15

Ala Gly Val Ala Met Ala
            20

<210> SEQ ID NO 41
<211> LENGTH: 22
<212> TYPE: PRT
<213> ORGANISM: Artificial Sequence
<220> FEATURE:
<223> OTHER INFORMATION: GAS-AWA

<400> SEQUENCE: 41

Met Leu Phe Lys Ser Leu Ser Lys Leu Ala Thr Ala Ala Ala Phe Phe
1               5                   10                  15

Ala Gly Val Ala Trp Ala
            20

<210> SEQ ID NO 42
<211> LENGTH: 108
<212> TYPE: PRT
<213> ORGANISM: Artificial Sequence
<220> FEATURE:
<223> OTHER INFORMATION: DOM7h-14-10R108C

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Lys Leu Leu Ile
        35                  40                  45
```

```
Met Trp Arg Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65              70                  75                  80

Glu Asp Phe Ala Thr Tyr Tyr Cys Ala Gln Gly Leu Arg His Pro Lys
                 85                  90                  95

Thr Phe Gly Gln Gly Thr Lys Val Glu Ile Lys Cys
                100                 105
```

<210> SEQ ID NO 43
<211> LENGTH: 34
<212> TYPE: PRT
<213> ORGANISM: Artificial Sequence
<220> FEATURE:
<223> OTHER INFORMATION: PYY 3-36 (with a lysine at position 10)

<400> SEQUENCE: 43

```
Ile Lys Pro Glu Ala Pro Gly Lys Asp Ala Ser Pro Glu Glu Leu Asn
 1               5                  10                  15

Arg Tyr Tyr Ala Ser Leu Arg His Tyr Leu Asn Leu Val Thr Arg Gln
                 20                  25                  30

Arg Tyr
```

<210> SEQ ID NO 44
<211> LENGTH: 324
<212> TYPE: DNA
<213> ORGANISM: Artificial Sequence
<220> FEATURE:
<223> OTHER INFORMATION: DOM 7h-14-10 R108C - nucleic acid sequence

<400> SEQUENCE: 44

```
gacatccaga tgacccagtc tccatcctcc ctgtctgcat ctgtaggaga ccgtgtcacc      60
atcacttgcc gggcaagtca gtggattggg tctcagttat cttggtacca gcagaaacca    120
gggaaagccc ctaagctcct gatcatgtgg cgttcctcgt tgcaaagtgg ggtcccatca    180
cgtttcagtg gcagtggatc tgggacagat tcactctca ccatcagcag tctgcaacct    240
gaagattttg ctacgtacta ctgtgctcag ggtttgaggc atcctaagac gttcggccaa    300
gggaccaagg tggaaatcaa atgt                                            324
```

<210> SEQ ID NO 45
<211> LENGTH: 1389
<212> TYPE: DNA
<213> ORGANISM: Artificial Sequence
<220> FEATURE:
<223> OTHER INFORMATION: Cynomolgus GLP-1 receptor cDNA sequence

<400> SEQUENCE: 45

```
atggccggca cccccggccc gctgcgcctc gcgctcctgc tgctcggggt ggtgggcagg      60
gccggccccc gccccagggt gccactgtgt ccctctggg agacggtgca gaaatggcga    120
gaataccgac gccagtgcca cgctccctg actgaggacc acctcccgc acagacttg      180 ttctgcaacc ggaccttcga tgaatatgcc tgctggccag atggggagcc aggctccttc    240
gtgaatgtca gctgccctg gtacctgccc tgggccagca gtgtgccgca gggccacgtg    300
taccggttct gcacagctga aggcctctgg ctgcagaagg acaactccag cctgccctgg    360
agggacttgt cggagtgtga ggagtccaag cgaggggaga gaaattcccc ggaggagcag    420
ctcctgtccc tctacatcat ctacacggtg ggctacgcac tctccttctc tgctctggtt    480
```

```
atcgcctctg cgatcctcct tggcttcaga cacctgcact gcacccggaa ctacatccac      540
ctgaacctgt ttgcatcctt catcctgcga gcattgtccg tcttcatcaa ggacgcagcc      600
ctcaagtgga tgtacagcac ggccgcccag cagcaccagt gggatgggct cctctcctac      660
caggactctc tgggctgccg cgtggtgttt ctgctcatgc aatactgtgt ggcggccaat      720
tactactggc tcttggtgga gggcgtgtac ctgtacacac tgctggcctt ctcggtcttc      780
tctgagcaac gaatcttcag gctgtatgtg agcgtaggct ggggtgttcc cctgctgttt      840
gttgtcccct ggggcattgt caagtacctc tatgaggacg agggctgctg gaccaggaac      900
tccaacatga actactggct cattatccgg ctgcccattc tctttgccat gggggtgaac      960
ttcctcatct ttgttcgggt catctgcatc gtggtatcca aactgaaggc caatctcatg     1020
tgcaagacag acatcaaatg cagacttgcc aagtccacgc tgacactcat ccccctgctg     1080
gggactcatg aggtcatctt tgcctttgtg atggacgagc atgcccgggg caccctgcgc     1140
ttcatcaagc tgttcacgga gctctccttt acctccttcc aggggctgat ggtggccatc     1200
ttgtactgct ttgtcaacaa tgaggtccag ttggaatttc ggaagagctg ggagcgctgg     1260
cggcttgagc acttgcacat ccagagggac agcagcatga agcccctcaa gtgtcccacc     1320
agcagcctga gcagtggggc cacggcgggc agcagcatgt acacagccac ttgccaggcc     1380
tcctgcagc                                                            1389

<210> SEQ ID NO 46
<211> LENGTH: 22
<212> TYPE: PRT
<213> ORGANISM: Artificial Sequence
<220> FEATURE:
<223> OTHER INFORMATION: Pel B

<400> SEQUENCE: 46

Met Lys Tyr Leu Leu Pro Thr Ala Ala Ala Gly Leu Leu Leu Leu Ala
 1               5                  10                  15

Ala Gln Pro Ala Met Ala
            20

<210> SEQ ID NO 47
<211> LENGTH: 115
<212> TYPE: DNA
<213> ORGANISM: Artificial Sequence
<220> FEATURE:
<223> OTHER INFORMATION: Oligonucleotide 1

<400> SEQUENCE: 47
ggaattccat atgaaaatca aaaccggtgc tcgcatcctg gctctgtccg ctctgaccac       60
tatgatgttc tccgcttccg cgctggctca tggtgaagga acatttacca gtgac          115

<210> SEQ ID NO 48
<211> LENGTH: 44
<212> TYPE: DNA
<213> ORGANISM: Artificial Sequence
<220> FEATURE:
<223> OTHER INFORMATION: Oligonucleotide 2

<400> SEQUENCE: 48
gttcagaatt cttattaccg tttgatttcc accttggtcc cttg                        44

<210> SEQ ID NO 49
<211> LENGTH: 26
<212> TYPE: PRT
<213> ORGANISM: Artificial Sequence
```

```
<220> FEATURE:
<223> OTHER INFORMATION: Mal E signal sequence

<400> SEQUENCE: 49

Met Lys Ile Lys Thr Gly Ala Arg Ile Leu Ala Leu Ser Ala Leu Thr
 1               5                  10                  15

Thr Met Met Phe Ser Ala Ser Ala Leu Ala
            20                  25

<210> SEQ ID NO 50
<211> LENGTH: 489
<212> TYPE: DNA
<213> ORGANISM: Artificial Sequence
<220> FEATURE:
<223> OTHER INFORMATION: DMS 7139 nucleic acid sequence for E.coli
      expression

<400> SEQUENCE: 50
cacggtgaag gtacgttcac ctctgacctg agcaaacaga tggaggaaga agcggttcgt    60
ctgttcatcg agtggctgaa aaacggtggt ccgtcttctg gtgctccgcc gccgtctggt   120
ggtggtggtg gttctggtgg tggtggttct ggtggtggtg gcagcgatat ccagatgact   180
cagtccccgt cttctctctc cgcctctgtt ggcgaccgtg ttaccatcac ttgtcgtgcg   240
agccagtgga tcggttccca gctgagctgg tatcagcaga aaccgggcaa agcgccgaaa   300
ctgctgatca tgtggcgctc tagcctgcag tctggtgtac cgtctcgttt ctccggctct   360
ggttctggta cggacttcac cctcacgatc tcttccctgc agccggaaga ctttgccacc   420
tactactgcg cacagggtct gcgtcacccg aaaaccttcg gtcagggtac caaagtcgag   480
atcaaacgt                                                          489
```

DRUG FUSIONS AND CONJUGATES

This application is a 371 of International Application No. PCT/EP2010/053806, filed 24 Mar. 2010, which claims the benefit of U.S. Provisional Application No. 61/163,917, filed 27 Mar. 2009, which are both incorporated by reference in their entireties.

The present invention relates to drug fusions and conjugates that have improved serum half lives. These fusions and conjugates comprise immunoglobulin (antibody) single variable domains and GLP and/or exendin molecules. The invention further relates to uses, formulations, compositions and devices comprising such drug fusions and conjugates.

BACKGROUND OF THE INVENTION

Many drugs that possess activities that could be useful for therapeutic and/or diagnostic purposes have limited value because they are rapidly eliminated from the body when administered. For example, many polypeptides that have therapeutically useful activities are rapidly cleared from the circulation via the kidney. Accordingly, a large dose must be administered in order to achieve a desired therapeutic effect. A need exists for improved therapeutic and diagnostic agents that have improved pharmacokinetic properties.

One such class of drugs that have a short half life in the body or systemic circulation is the incretin hormones such as Glucagon-like peptide 1, or Peptide YY and also exendin, for example exendin-4.

Glucagon-like peptide (GLP)-1 is an incretin hormone with potent glucose-dependent insulinotropic and glucagonostatic actions, trophic effects on the pancreatic β cells, and inhibitory effects on gastrointestinal secretion and motility, which combine to lower plasma glucose and reduce glycemic excursions. Furthermore, via its ability to enhance satiety, GLP-1 reduces food intake, thereby limiting weight gain, and may even cause weight loss. Taken together, these actions give GLP-1 a unique profile, considered highly desirable for an antidiabetic agent, particularly since the glucose dependency of its antihyperglycemic effects should minimize any risk of severe hypoglycemia. However, its pharmacokinetic/pharmacodynamic profile is such that native GLP-1 is not therapeutically useful. Thus, while GLP-1 is most effective when administered continuously, single subcutaneous injections have short-lasting effects. GLP-1 is highly susceptible to enzymatic degradation in vivo, and cleavage by dipeptidyl peptidase IV (DPP-IV) is probably the most relevant, since this occurs rapidly and generates a noninsulinotropic metabolite. Strategies for harnessing GLP-1's therapeutic potential, based on an understanding of factors influencing its metabolic stability and pharmacokinetic/pharmacodynamic profile, have therefore been the focus of intense research.

Extensive work has been done to attempt to inhibit the peptidase or to modify GLP-1 in such a way that its degradation is slowed down while still maintaining biological activity. WO05/027978 discloses GLP-1 derivatives having a protracted profile of action. WO 02/46227 discloses heterologous fusion proteins comprising a polypeptide (for example, albumin) fused to GLP-1 or analogues (the disclosure of these analogues is incorporated herein by reference as examples of GLP-1 analogues that can be used in the present invention). WO05/003296, WO03/060071, WO03/059934 disclose amino fusion protein wherein GLP-1 has fused with albumin to attempt to increase the half-life of the hormone.

However, despite these efforts a long lasting active GLP-1 has not been produced.

As such, particularly in the fields of diabetes and obesity, there is a tremendous need for improved GLP-1 peptides or other agents such as exendin-4 or PYY that similarly have an insulinotropic effect amenable to treatment for diabetes and obesity in particular. There is thus a need to modify GLP-1, exendin-4 and other insulinotropic peptides to provide longer duration of action in vivo while maintaining their low toxicity and therapeutic advantages.

SUMMARY OF THE INVENTION

The present invention provides a composition which is a fusion or conjugate and which comprises or consists of (a) an insulinotropic agent or molecule, or an incretin drug or molecule, which can for example be an exendin-4, PYY e.g. 3-26 PYY or a GLP-1 e.g. the GLP-1 (7-37) A8G mutant, present as a fusion or conjugate with (b) a dAb which binds specifically to serum albumin (AlbudAb TM) selected from: (i) the DOM 7h-14 domain antibody (dAb) (the amino acid sequence of DOM 7h-14 is shown in FIG. 1(h): SEQ ID NO 8), (ii) the DOM 7h-14-10 domain antibody (dAb) (the amino acid sequence of DOM 7h-14-10 is shown in FIG. 1(o):SEQ ID NO 26) or a dAb which has up to 4 amino acid differences from the sequence of the DOM 7h-14-10 dAb; and (iii) the DOM 7h-11-15 dAb (the amino acid sequence of DOM 7h-11-15 is shown in FIG. 1(p): SEQ ID NO 27) or (iv) the DOM 7h-14-10 R108C domain antibody (dAb) (the amino acid sequence of DOM 7h-14-10 is shown in FIG. 1(r).

An amino acid or chemical linker may also optionally be present joining the insulinotropic agent or incretin drug, e.g. exendin-4 and/or GLP-1, or PYY with the dAb e.g. with the DOM7h-14 dAb, DOM 7h-14-10 dAb, DOM 7h-11-15 dAb. The linker can be for example a helical linker e.g. the helical linker of sequence shown in FIG. 1 (k): SEQ ID NO 11, or it may be a gly-ser linker e.g. with an amino acid sequence shown in FIG. 1 (l): SEQ ID NO 12.

In certain embodiments, the fusions (or conjugates) of the invention can comprise further molecules e.g. further peptides or polypeptides.

The insulinotropic agent or incretin drug (e.g. exendin and/or GLP-1) can be present as a fusion (or conjugate) with either the N-terminal or C-terminal of the dAb.

In certain embodiments the invention provides a polypeptide comprising or consisting of a fusion molecule which is selected from the following:
(a) 2×GLP-1 (7-37) A8G DOM7h-14 dAb fusion (DAT0114, the amino acid sequence is shown in FIG. 1 (a): SEQ ID NO 1)
(b) Exendin 4 (G4S linker)3 DOM7h-14 dAb fusion (DAT0115, the amino acid sequence is shown in FIG. 1(b): SEQ ID NO 2),
(c) Exendin 4—DOM7h-14 dAb fusion (DAT0116, the amino acid sequence is shown in FIG. 1 (c): SEQ ID NO 3).
(d) Exendin 4, helical linker, DOM7h-14 dAb fusion (DAT0117, the amino acid sequence is shown in FIG. 1(d): SEQ ID NO 4).
(e) GLP-1 (7-37) A8G (G4S linker)3 DOM7h-14 dAb fusion (DAT0118, the amino acid sequence is shown in FIG. 1 (e): SEQ ID NO 5),
(f) GLP-1 (7-37) A8G DOM7h-14 dAb fusion (DAT0119, the amino acid sequence is shown in FIG. 1(f): SEQ ID NO 6),
(g) GLP-1 (7-37) A8G, helical linker, DOM7h-14 dAb fusion (DAT0120, the amino acid sequence is shown in FIG. 1 (g): SEQ ID NO 7),
(h) Exendin 4, (G4S)3, linker DOM7h-14-10 fusion (DMS7139, the amino acid sequence is shown in FIG. 1 (m): SEQ ID NO 24), (i) Exendin 4, (G4S)3, linker DOM7h-11-15 fusion (DMS7143, the amino acid sequence is shown in FIG. 1(*n*): SEQ ID NO 25)

The invention also provides conjugate molecules comprising or consisting of the amino acid sequences of those described above i.e. those with the amino acid sequences shown by SEQ ID NOs-1-7 and SEQ ID NOs 24-25.

In certain embodiments the invention provides a polypeptide comprising or consisting of a conjugate molecule which is:

a DOM 7h-14-10 (R108C) AlbudAb conjugated to a C-terminally amidated PYY3-36 via a lysine (introduced at position 10 of PYY) and a 4 repeat PEG linker. The amino acid sequence and structure of this peptide conjugate is shown in FIG. 14.

The invention also provides a polypeptide comprising or consisting of the amino acid sequence of the Exendin 4, (G4S)3, linker DOM7h-14-10 fusion (DMS7139, the amino acid sequence is shown in FIG. 1 (*m*): SEQ ID NO 24), or a fusion or conjugate molecule which has up to 4 amino acids changes from the amino acid sequence of DMS7139, the amino acid sequence is shown in FIG. 1 (*m*).

DOM 7h-14 is a human immunoglobulin single variable domain or dAb (Vk) that binds to serum albumin and its amino acid sequence is shown in FIG. 1(*h*): SEQ ID NO 8. The CDR regions of DOM 7h-14 dAb are underlined in the amino acid sequence shown in FIG. 1(*h*): SEQ ID NO 8.

DOM 7h-14-10 is a human immunoglobulin single variable domain or dAb that binds to serum albumin and its amino acid sequence is shown in FIG. 1(*o*): SEQ ID NO 26. The CDR regions of DOM 7h-14-10 dAb are underlined in the amino acid sequence shown in FIG. 1(*o*): SEQ ID NO 26.

DOM 7h-11-15 is a human immunoglobulin single variable domain or dAb that binds to serum albumin and its amino acid sequence is shown in FIG. 1(*p*): SEQ ID NO 27. The CDR regions of DOM 7h-11-15 dAb are underlined in the amino acid sequence shown in FIG. 1(*p*): SEQ ID NO 27.

As used herein, "fusion" refers to a fusion protein that comprises as a first moiety a DOM7h-14 dAb or a DOM7h-14-10 dAb or a DOM 7h-11-15 dAb that binds serum albumin and as a second moiety an insulinotropic agent or an incretin drug. The dAb that binds serum albumin and the drug or agent are present as discrete parts (moieties) of a single continuous polypeptide chain. The first (dAb) and second (incretin drug or insulinotropic agent) moieties can be directly bonded to each other through a peptide bond or linked through a suitable amino acid, or peptide or polypeptide linker. Additional moieties e.g. peptides or polypeptides (e.g. third, fourth) and/or linker sequences, can be present as appropriate. The first moiety can be in an N-terminal location, C-terminal location or internal relative to the second moiety. In certain embodiments the fusion protein contains one or more than one (e.g. one to about 20) dAb moieties.

As used herein, "conjugate" refers to a composition comprising a dAb that binds serum albumin to which an insulinotropic agent or incretin drug e.g. GLP-1, Exendin-4, PYY e.g. PYY 3-36 is covalently or non-covalently bonded. The insulinotropic agent or incretin drug can be covalently bonded to the dAb directly or indirectly through a suitable linker moiety e.g. a PEG linker moiety. The drug or agent can be bonded to the dAb at any suitable position, such as the amino-terminus, the carboxyl-terminus or through suitable amino acid side chains (e.g., thecamino group of lysine, or thiol group of cysteine). Alternatively, the drug or agent can be noncovalently bonded to the dAb directly (e.g., electrostatic interaction, hydrophobic interaction) or indirectly (e.g., through noncovalent binding of complementary binding partners (e.g., biotin and avidin), wherein one partner is covalently bonded to drug or agent and the complementary binding partner is covalently bonded to the dAb).

The invention further provides (substantially) pure monomer of any of the conjugates or fusions of the invention e.g. of DAT0114, DAT 0115, DAT0116, DAT0117, DAT0118, DAT0119 and DAT120, DMS 7139 or DMS 7143 or DMS 7143. In one embodiment, it is at least 98, 99, 99.5% pure or 100% pure monomer.

The invention also provides nucleic acids encoding the fusions described herein for example nucleic acids encoding DAT0114, DAT 0115, DAT0116, DAT0117, DAT0118, DAT0119 and DAT120, DMS 7139 or DMS 7143 and e.g. wherein the nucleic acid sequences are shown in FIG. 2 (SEQ ID NOS 13-32). Also provided are host cells that comprise these nucleic acids.

The invention also provides amino acids encoding dAbs that bind to serum albumin (AlbudAbs TM) selected from: DOM7h-14 (SEQ ID NO 8), DOM7h-14-10 (SEQ ID NO 26), DOM7h-11-15 (SEQ ID NO 27) and DOM 7h-14-10R108C (SEQ ID NO 42)

The invention also provides nucleic acids encoding dAbs that bind to serum albumin selected from: DOM7h-14 (SEQ ID NO 23), DOM7h-14-10 (SEQ ID NO 31), DOM7h-11-15 (SEQ ID NO 32) and DOM 7h-14-10R108C (SEQ ID NO 44).

The invention further provides a method for producing a fusion of the present invention which method comprises maintaining a host cell that comprises a recombinant nucleic acid and/or construct that encodes a fusion of the invention under conditions suitable for expression of said recombinant nucleic acid, whereby a fusion is produced.

The invention also provides compositions (e.g., pharmaceutical compositions) comprising a fusion or conjugate of the invention.

The invention also provides a method for treating an individual having a disease or disorder, such as those described herein e.g. a metabolic disease such as hyperglycemia, impaired glucose tolerance, beta cell deficiency, diabetes (for example type 1 or type 2 diabetes or gestational diabetes) or obesity or diseases characterised by overeating e.g. it can be used to suppress appetite e.g. in Prader-Willi syndrome, and which comprises administering to said individual a therapeutically effective amount of a fusion or conjugate of the invention.

Other metabolic disorders include, but are not limited to, insulin resistance, insulin deficiency, hyperinsulinemia, hyperglycemia, dyslipidemia, hyperlipidemia, hyperketonemia, hypertension, coronary artery disease, atherosclerosis, renal failure, neuropathy (e.g., autonomic neuropathy, parasympathetic neuropathy, and polyneuropathy), retinopathy, cataracts, metabolic disorders (e.g., insulin and/or glucose metabolic disorders), endocrine disorders, obesity, weight loss, liver disorders (e.g., liver disease, cirrhosis of the liver, and disorders associated with liver transplant), and conditions associated with these diseases or disorders.

In addition, conditions associated with diabetes that can be prevented or treated with the compounds of the present invention include, but are not limited to, hyperglycemia, obesity, diabetic retinopathy, mononeuropathy, polyneuropathy, atherosclerosis, ulcers, heart disease, stroke, anemia, gangrene (e.g., of the feet and hands), impotence, infection, cataract, poor kidney function, malfunctioning of the autonomic nervous system, impaired white blood cell function, Carpal tunnel syndrome, Dupuytren's contracture, and diabetic ketoacidosis.

The invention also provides methods for treating or preventing diseases associated with elevated blood glucose comprising administering at least one dose of the conjugates or fusions and/or pharmaceutical compositions of the present invention to patient or subject.

The invention further relates to methods of regulating insulin responsiveness in a patient, as well as methods of increasing glucose uptake by a cell, and methods of regulating insulin sensitivity of a cell, using the conjugates or fusions of the invention. Also provided are methods of stimulating insulin synthesis and release, enhancing adipose, muscle or liver tissue sensitivity towards insulin uptake, stimulating glucose uptake, slowing digestive process, or blocking the secretion of glucagon in a patient, comprising administering to said patient a fusion or conjugate of the invention e.g. comprising administering at least one dose of the drug conjugate or fusions and/or pharmaceutical composition of the present invention.

The fusions or conjugates and/or pharmaceutical compositions of the invention may be administered alone or in combination with other molecules or moieties e.g. polypeptides, therapeutic proteins and/or molecules (e.g., insulin and/or other proteins (including antibodies), peptides, or small molecules that regulate insulin sensitivity, weight, heart disease, hypertension, neuropathy, cell metabolism, and/or glucose, insulin, or other hormone levels, in a patient). In specific embodiments, the conjugates or fusions of the invention are administered in combination with insulin (or an insulin derivative, analog, fusion protein, or secretagogue).

The invention also provides for use of a conjugate or fusion of the invention for the manufacture of a medicament for treatment of a disease or disorder, such as any of those mentioned above e.g. a metabolic disorder such as hyperglycemia, diabetes (type 1 or 2 or gestational diabetes) or obesity.

The invention also relates to use of a fusion or conjugate as described herein for use in therapy, diagnosis or prophylaxis.

The fusions or conjugates of the invention e.g. the dAb component of the fusion can be further formatted to have a larger hydrodynamic size to further extend the half life, for example, by attachment of a PEG group, serum albumin, transferrin, transferrin receptor or at least the transferrin-binding portion thereof, an antibody Fc region, or by conjugation to an antibody domain. For example, the dAb that binds serum albumin can be formatted as a larger antigen-binding fragment of an antibody (e.g., formatted as a Fab, Fab', $F(ab)_2$, $F(ab')_2$, IgG, scFv).

In other embodiments of the invention described throughout this disclosure, instead of the use of a "dAb" in a fusion of the invention, it is contemplated that the skilled addressee can use a domain that comprises the CDRs of a dAb e.g. CDRs of DOM 7h-14, DOM 7h-14-10 or DOM 7h-11-15 that binds serum albumin (e.g., CDRs grafted onto a suitable protein scaffold or skeleton, e.g. an affibody, an SpA scaffold, an LDL receptor class A domain or an EGF domain). The disclosure as a whole is to be construed accordingly to provide disclosure of such domains in place of a dAb.

In certain embodiments, the invention provides a fusion or conjugate according to the invention that comprises an insulinotropic agent or incretin drug and a dual-specific ligand or multi-specific ligand that comprises a first dAb according to the invention that binds serum albumin e.g. DOM 7h-14, DOM 7h-14-10 or DOM 7h-11-15 and a second dAb that has the same or a different binding specificity from the first dAb and optionally in the case of multi-specific ligands further dAbs. The second dAb (or further dAbs) may optionally bind a different target e.g. FgFr 1c, or CD5 target.

Thus, in one aspect, the invention provides the fusions or conjugates of the invention for delivery by parenteral administration e.g. by subcutaneous, intramuscular or intravenous injection, inhalation, nasal delivery, transmucossal delivery, oral delivery, delivery to the GI tract of a patient, rectal delivery or ocular delivery. In one aspect, the invention provides the use of the fusions or conjugates of the invention in the manufacture of a medicament for delivery by subcutaneous injection, inhalation, intravenous delivery, nasal delivery, transmucossal delivery, oral delivery, delivery to the GI tract of a patient, rectal delivery or ocular delivery.

In one aspect, the invention provides a method for delivery to a patient by subcutaneous injection, pulmonary delivery, intravenous delivery, nasal delivery, transmucossal delivery, oral delivery, delivery to the GI tract of a patient, rectal or ocular delivery, wherein the method comprises administering to the patient a pharmaceutically effective amount of a fusion or conjugate of the invention.

In one aspect, the invention provides an oral, injectable, inhalable, nebulisable or ocular formulation comprising a fusion or conjugate of the invention. The formulation can be a tablet, pill, capsule, liquid or syrup. In one aspect the compositions can be administered orally e.g. as a drink, for example marketed as a weight loss drink for obesity treatment. In one aspect, the invention provides a formulation for rectal delivery to a patient, the formulation can be provided e.g. as a suppository.

A composition for parenteral administration of GLP-1 compounds may, for example, be prepared as described in WO 03/002136 (incorporated herein by reference).

A composition for nasal administration of certain peptides may, for example, be prepared as described in European Patent No. 272097 (to Novo Nordisk A/S) or in WO 93/18785 (all incorporated herein by reference).

The term "subject" or "individual" is defined herein to include animals such as mammals, including, but not limited to, primates (e.g., humans), cows, sheep, goats, horses, dogs, cats, rabbits, guinea pigs, rats, mice or other bovine, ovine, equine, canine, feline, rodent or murine species.

The invention also provides a kit for use in administering compositions according to the invention (e.g., conjugates or fusions of the invention) to a subject (e.g., patient), comprising a composition (e.g., conjugate or fusion of the invention), a drug delivery device and, optionally, instructions for use. The composition (e.g., conjugate, or fusion) can be provided as a formulation, such as a freeze dried formulation. In certain embodiments, the drug delivery device is selected from the group consisting of a syringe, an inhaler, an intranasal or ocular administration device (e.g., a mister, eye or nose dropper), and a needleless injection device.

The compositions (e.g. conjugates or fusions) of this invention can be lyophilized for storage and reconstituted in a suitable carrier prior to use. Any suitable lyophilization method (e.g., spray drying, cake drying) and/or reconstitution techniques can be employed. It will be appreciated by those skilled in the art that lyophilisation and reconstitution can lead to varying degrees of antibody activity loss and that use levels may have to be adjusted to compensate. In a particular embodiment, the invention provides a composition comprising a lyophilized (freeze dried) composition (e.g., drug conjugate, drug fusion) as described herein. Preferably, the lyophilized (freeze dried) composition (e.g., drug conjugate, drug fusion) loses no more than about 20%, or no more than about 25%, or no more than about 30%, or no more than about 35%, or no more than about 40%, or no more than about 45%, or no more than about 50% of its activity (e.g., binding activity for serum albumin) when rehydrated. Activity is the amount of composition (e.g., drug conjugate, drug fusion) required to produce the effect of the s composition before it was lyophilized. For example, the amount of conjugate or fusion needed to achieve and maintain a desired serum concentration for a desired period of time. The activity of the composition (e.g., drug conjugate, drug fusion) can be determined using any suitable method before lyophilization, and the activity can be determined using the same method after rehydration to determine amount of lost activity.

The invention also provides sustained release formulations comprising the fusions or conjugates of the invention, such sustained release formulations can comprise the fusion or conjugate of the invention in combination with, e.g. hyaluronic acid, microspheres or liposomes and other pharmaceutically or pharmacologically acceptable carriers, excipients and/or diluents. Such sustained release formulations can in the form of for example suppositories.

In one aspect, the invention provides a pharmaceutical composition comprising a fusion or conjugate of the invention, and a pharmaceutically or physiologically acceptable carrier, excipient or diluent.

The invention also provides, a modified leader sequence, which has at its C terminal end the amino acid sequence AMA or AWA, wherein the leader sequence is not the wild type sequence. The modified leader sequence may be OmpA-AMA or -AWA; or OmpT-AMA or -AWA; or GAS-AMA or -AWA.

The modified leader sequence may be used for expression of a heterologous polypeptide in a host cell. The heterologous polypeptide may comprise or consist of an insulinotropic agent or an incretin drug. The heterologous polypeptide may comprise or consist of a domain antibody (dAb) e.g. a dAb that binds serum albumin.

The heterologous polypeptide for expression by the modified leader may be a fusion or conjugate comprising or consisting of (a) an insulinotropic agent or an incretin drug present as a fusion or a conjugate with, (b) a dAb e.g. a dAb that binds serum albumin e.g. a dAb selected from: the DOM 7h-14 Vk domain antibody (dAb) which binds serum albumin and which has the amino acid sequence shown in FIG. 1(*h*) (SEQ ID NO 8), the DOM 7h-14-10 dAb which has the amino acid sequence shown in FIG. 1(*o*) (SEQ ID NO 26), and the DOM 7h-11-15 dAb which has the amino acid sequence shown in FIG. 1(*p*) (SEQ ID NO 27).

The modified leader sequence may also be used for expression of a heterologous polypeptide which comprises or consists of a fusion selected from:
(a) 2×GLP-1 (7-37) A8G DOM7h-14 dAb fusion (DAT0114, the amino acid sequence is shown in FIG. 1 (*a*): SEQ ID NO 1)
(b) Exendin 4 (G4S linker)3 DOM7h-14 dAb fusion (DAT0115, the amino acid sequence is shown in FIG. 1(*b*): SEQ ID NO 2),
(c) Exendin 4—DOM7h-14 dAb fusion (DAT0116, the amino acid sequence is shown in FIG. 1 (*c*): SEQ ID NO 3).
(d) Exendin 4, helical linker, DOM7h-14 dAb fusion (DAT0117, the amino acid sequence is shown in FIG. 1(*d*): SEQ ID NO 4).
(e) GLP-1 (7-37) A8G (G4S linker)3 DOM7h-14 dAb fusion (DAT0118, the amino acid sequence is shown in FIG. 1 (*e*): SEQ ID NO 5),
(f) GLP-1 (7-37) A8G DOM7h-14 dAb fusion (DAT0119, the amino acid sequence is shown in FIG. 1(*f*): SEQ ID NO 6),
(g) GLP-1 (7-37) A8G, helical linker, DOM7h-14 dAb fusion (DAT0120, the amino acid sequence is shown in FIG. 1 (*g*): SEQ ID NO 7),
(h) Exendin 4, (G4S)3, linker DOM7h-14-10 fusion (DMS7139, the amino acid sequence is shown in FIG. 1 (*m*): SEQ ID NO 24),
(i) Exendin 4, (G4S)3, linker DOM7h-11-15 fusion (DMS7143, the amino acid sequence is shown in FIG. 1 (*n*): SEQ ID NO 25).

The heterologous polypeptide to be expressed by the modified leader can also comprise or consist of conjugate molecules with the amino acid sequences of those described above i.e. those with the amino acid sequences shown by SEQ ID NOs-1-7 and SEQ ID NOs 24-25.

The heterologous polypeptide to be expressed by the modified leader can also comprise or consist of the amino acid sequence of the Exendin 4, (G4S)3, linker DOM7h-14-10 fusion (DMS7139, the amino acid sequence is shown in FIG. 1 (*m*): SEQ ID NO 24), or a fusion or conjugate molecule which has up to 4 amino acids changes from the amino acid sequence of DMS7139, the amino acid sequence is shown in FIG. 1 (*m*).

The host cell for expression may be a microbial host cell, a prokaryotic host cell, a Gram negative bacterial host cell, or an *E. coli* host cell.

Also provided is a process of producing a mixture of (i) an insulinotropic agent or an incretin drug; and (ii) an insulinotropic agent or an incretin drug minus 2 amino acids at the N-terminus of the insulinotropic agent or incretin drug; the process comprising the step of expressing (i) in a host cell using a leader sequence which results in cleavage before position 1 and cleavage before position 3 of the insulinotropic agent or incretin drug. The insulinotropic agent or an incretin drug may be in the form of a fusion or conjugate e.g. with a dAb which binds serum albumin as defined above. The invention also provides mixtures obtained or obtainable by the process described above.

The leader sequence may ompA, ompT, GAS, or any one of the modified sequences described above. The process may comprise the step of producing the mixture in a host cell by heterologous expression. The host cell may be a microbial host cell, a prokaryotic host cell, a Gram negative bacterial host cell, or an *E. coli* host cell.

Insulinotropic agents and incretin drugs such as GLP-1 have a wide variety of therapeutic effects, which may be mediated via the GLP-1R (such as those stimulating glucose dependent insulin secretion from the pancreas). It has also been proposed that there is a class of effects that may either be mediated by the DPPIV cleavage product, GLP-1 9-36amide (or GLP-1 9-37). GLP-1 9-37 is not active in stimulating glucose sensitive insulin secretion from the pancreas, but it has been proposed to have other biological effects, possibly via a non-GLP-1R driven mechanism. As most clinical applications to date for the GLP-1 class of molecules have targeted diabetes, via pancreatic GLP-1R, stability to DPPIV has been engineered into the peptides, either via using a non-human GLP-1 analogue, such as Exendin-4, or mutating amino acids 8 or 9 in GLP-1 such as used in Albiglutide (Syncria), or via chemical or synthetic modifications at the amino end of the peptide. An additional approach has been the global blockade of DPPIV activity using small molecule DPPIV inhibitors such as vildagliptin (Galvus) and sitagliptin (Januvia), which prolongs the half-life of any endogenous secreted GLP-1. Both of these approaches effectively reduce the level of the DPPIV metabolite GLP-1 9-36amide or GLP-1 9-37.

However, the DPPIV metabolite GLP-1 9-36amide or GLP-1 9-37 has been proposed to have a desirable biological effect. Several studies have shown that the DPPIV cleavage product of GLP-1 7-36 amide, namely GLP-1 9-36amide, which is rapidly formed after secretion of GLP-1 7-36, and is more abundant under normal conditions than GLP-1 7-37, may have a biological effect. Several different routes of action have been proposed for this mechanism, as listed below:

GLP-1(9-37) is an antagonist at the GLP-1R: see for example: Eur J. Pharmacol. 1996 Dec. 30; 318(2-3):429-35.

Glucagon-like peptide-1-(9-36) amide is a major metabolite of glucagon-like peptide-1-(7-36) amide after in vivo administration to dogs, and it acts as an antagonist on the pancreatic receptor (Knudsen L B, Pridal L. J Biol. Chem. 1997 Aug. 22; 272(34): 21201-6) and High potency antagonists of the pancreatic glucagon-like peptide-1 receptor (Montrose-Rafizadeh C, Yang H, Rodgers B D, Beday A, Pritchette L A, Eng J. J Biol. Chem. 1997 Aug. 22; 272(34):21201-6).

GLP-1(9-37) signals via a different mechanism to GLP-1(7-37), via a non-insulin dependent mechanism: (Am J Physiol Endocrinol Metab. 2002 April; 282(4):E873-9.) GLP-1-(9-36) amide reduces blood glucose in anesthetized pigs by a mechanism that does not involve insulin secretion (Deacon C F, Plamboeck A, Møller S, Holst J J.)

Or by acting to increase insulin sensitivity in obese individuals: (Obesity (Silver Spring). 2008 July; 16(7):1501-9. Epub 2008 Apr. 17.

GLP-1 (9-36) amide, cleavage product of GLP-1 (7-36) amide, is a glucoregulatory peptide (Elahi D, Egan J M, Shannon R P, Meneilly G S, Khatri A, Habener J F, Andersen D K).

This activity has not been shown for the minus two amino acid species of exendin, as this is not formed as a result of DPPIV cleavage, but it is possible that this may also be the case for a minus two amino acid species of exendin-4. Exendin-4 has also been shown to work via GLP-1R dependent and independent pathways in terms of cardiac and other effects (Circulation. 2008; 117:2340-2350: Cardioprotective and Vasodilatory Actions of Glucagon-Like Peptide 1 Receptor Are Mediated Through Both Glucagon-Like Peptide 1 Receptor-Dependent and Independent Pathways Kiwon Ban, MSc; M. Hossein Noyan-Ashraf, PhD; Judith Hoefer, M D; Steffen-Sebastian Bolz, M D, PhD; Daniel J. Drucker, M D; Mansoor Husain, M D). This raises the possibility that there may indeed be similar and parallel activities for both the full length and minus two amino acid forms of exendin.

At least two process routes are available for producing mixtures of an insulinotropic agent or an incretin drug and the minus two amino acid versions. For example, there can be the separate production of a full length GLP-1 7-36amide (in the desired half-life prolonging format such as an AlbudAb), and the GLP-1 9-36amide (or desired fusion protein). These could then be mixed to give a product with the desired ratio of GLP-1 7-36 and GLP-1 9-36 molecules. Two parallel GMP processes may be used to yield the drug mixture.

An alternative method is to select a secretion signal for which the signal peptidase enzyme, responsible for removing the signal sequence, does not have a single site of cleavage, but rather has two sites of cleavage. These are cut in a ratio defined by the secretion signal used. Thus, depending of the secretion signal selected, the ratio produced may be:

100% cleavage before position 1 to give GLP-1 7-36 (or other insulinotropic agent or incretin drug full length molecule); or 100% cleavage before position 3 to give GLP-1 9-36 (or other insulinotropic agent or incretin drug minus two amino acid sequence); or any % between 0 and 100 for each of the full length or minus 2 versions. For example, the ratio could be:

90% full length:10% minus 2 amino acid;
80% full length:20% minus 2 amino acid;
75% full length:25% minus 2 amino acid;
50% full length:50% minus 2 amino acid;
25% full length:75% minus 2 amino acid;
20% full length:80% minus 2 amino acid; or
10% full length:90% minus 2 amino acid.

Selection of the appropriate leader sequence to yield the desired ratio will allow production from one single host cell. This is a key advantage in terms of GMP process. This allows the exploitation of the potential therapeutic effects of both species while retaining stability to endogenous enzymes.

A whole range of other endogenous peptides and analogues are also processed by amino terminal dipeptidases, yielding the original full length molecule and/or a dipeptidase susceptible species. Thus this approach may be useful for the production of any peptides and protein where a single manufacturing run can yield a defined mixture of two species differing in length by a few amino acids, where the differing amino acids comprise part of a recognition site for a signal peptidase. Utilisation of this process may be possible in mammalian, eukaryotic, or prokaryotic host cells, for example in *E. coli*.

BRIEF DESCRIPTION OF THE DRAWINGS

FIG. 1: is an illustration of the amino acid sequences of (a) DAT0114 (SEQ ID NO 1), (b) DAT0115 (SEQ ID NO 2), (c) DAT0116 (SEQ ID NO 3), (d) DAT0117 (SEQ ID NO 4), (e) DAT0118 (SEQ ID NO 5), (f) DAT0119 (SEQ ID NO 6) (g) DAT0120 (SEQ ID NO 7) (h) DOM 7h-14 (SEQ ID NO 8) (dAb) (the CDRs are underlined), (i) GLP-1 7-37 A(8)G (SEQ ID NO 9), (j) exendin-4 (SEQ ID NO 10), (k) Helical linker (SEQ ID NO 11) (l) Gly-ser linker (SEQ ID NO 12), (m) DMS 7139 (SEQ ID NO 24, (n) DMS 7143 (SEQ ID NO 25) (o) DOM 7h-14-10 (SEQ ID NO 26) (dAb) (the CDRs are underlined), (p) DOM 7h-11-15 (SEQ ID NO 27) (dAb) (the CDRs are underlined) (q) OmpT AWA signal peptide (leader) (SEQ ID NO 28) (r) DOM7h-14-10R108C (SEQ ID NO 42) (s) PYY 3-36 (with a lysine at position 10) (SEQ ID NO 43).

FIG. 2: is an illustration of the nucleic acid sequences of: (a) DAT0114 (mammalian construct) (SEQ ID NO 13), (b) DAT0115 (mammalian construct) (SEQ ID NO 14), (c) DAT0115 (optimized for *E. coli* construct) (SEQ ID NO 15), (d) DAT0116 (mammalian construct) (SEQ ID NO 16), (e) DAT0116 (optimized for *E. coli* construct) (SEQ ID NO 17), (f) DAT0117 (mammalian construct) (SEQ ID NO 18), (g) DAT0117 (optimized for *E. coli* construct) (SEQ ID NO 19), (h) DAT0118 (mammalian construct) (SEQ ID NO 20), (i) DAT0119 (mammalian construct) (SEQ ID NO 21), (j) DAT0120 (mammalian construct) (SEQ ID NO 22), (k) Dom7h-14 (SEQ ID NO 23) (l) DMS 7139 (SEQ ID NO 29, (m) DMS 7143 (SEQ ID NO 30) (n) Dom7h-14-10 (SEQ ID NO 31) (dAb), (o) DOM7h-11-15 (SEQ ID NO 32) (dAb) (p) Omp AWA signal peptide (SEQ ID NO 33), (q) DOM 7h-14-10 R108C (dAb) (SEQ ID NO 44), (r) cDNA of cynomologous monkey (SEQ ID NO 45) (s) Oligonucleotide 1 (SEQ ID NO 47), (t) Oligonucleotide 2 (SEQ ID NO 48) (u) Nucleic acid sequence of DMS 7139 for expression in *E. coli* (SEQ ID NO 50).

FIG. 3: (a) shows dose dependent reduction in body weight in mouse model of obesity by administering DAT0115 (b) shows daily food consumption in mouse model of obesity by administering DAT0115.

FIG. 4: shows a DSC of DAT0115: Solid line—DAT0115 trace, dotted line—fit to a non-2-state model.

FIG. 5: shows a DSC of Lysozyme: Solid line—lysozyme trace, dotted line—fit to a non-2-state model (traces overlay so dotted trace cannot be seen).

FIG. 6 shows SEC MALLS of DAT0115.

FIG. 7: shows SEC MALLS of DAT0117.

FIG. 8: shows SEC MALLS of DAT0120.

FIG. 9: shows the amino acid sequences of leaders: (a) ompA (*E. coli* derived) (SEQ ID NO 34), (b) ompA-AMA (artificial sequence) (SEQ ID NO 35), (c) ompA-AWA (artificial sequence) (SEQ ID NO 36), (d) ompT (*E. coli* derived) (SEQ ID NO 37), (e) ompT-AMA (artificial sequence) (SEQ ID NO 38), (f) GAS (*S. cerevisiae* derived) (SEQ ID NO 39), (g) GAS-AMA (artificial sequence) (SEQ ID NO 40), (h) GAS-AWA (artificial sequence) (SEQ ID NO 41) (i) Pel B (*Erwinia carotovora*) (SEQ ID NO 46) (j) Mal E (artificial sequence) (SEQ ID NO 49).

FIG. 10: shows Purified DMS7139 analyzed by mass spectrometry

FIG. 11: shows an illustration of the statistical significance of blood glucose lowering including comparisons between DAT0115 and control, DMS7139 and control and between DMS7139 and DAT0115, (a) shows study design and (b) graphical representation of glucose AUC. Confidence intervals which do not overlap the horizontal line are significant.

FIG. 12: shows repeat dose of DMS7139 shows dose-dependent lowering of HbA1c when compared to DOM7h-14 control FIG. 13: shows DAT0115 and DMS7139 show dose dependent reduction in food consumption and body weight compared to the DOM7h-14 control in DIO mouse model of obesity. In the graph mcg=micrograms.

FIG. 14: shows a peptide conjugate which is: a DOM7h-14-10 (R108C) AlbudAb conjugated to a C-terminally amidated PYY3-36 via a lysine (introduced at position 10 of PYY) and a 4 repeat PEG linker. The line represents the linker which is covalently attached to the free C terminal cysteine of the DOM7h-14-10 (R108C) AlbudAb and the lysine at position 10 of the PYY sequence. The amino acid sequence and structure of this peptide conjugate is as follows.

FIG. 15: shows DMS7605 showed a dose dependent reduction in body weight compared to the vehicle control

DETAILED DESCRIPTION OF THE INVENTION

Within this specification the invention has been described, with reference to embodiments, in a way which enables a clear and concise specification to be written. It is intended and should be appreciated that embodiments may be variously combined or separated without parting from the invention.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4$^{th}$ Ed, John Wiley & Sons, Inc. which are incorporated herein by reference) and chemical methods.

The term "insulinotropic agent" as used herein means a compound which is able to stimulate, or cause the stimulation of, the synthesis or expression of, or the activity of the hormone insulin. Known examples of insulinotropic agents include but are not limited to e.g. glucose, GIP, GLP, Exendin (e.g. exendin-4 and exendin-3), PYY, and OXM.

The term "incretin" as used herein means a type of gastrointestinal hormone that causes an increase in the amount of insulin released when glucose levels are normal or particularly when they are elevated. By way of example they include GLP-1, GIP, OXM, PYY (e.g. PYY 3-36), VIP, and PP (pancreatic polypeptide).

The term "analogue" as used herein referring to a polypeptide means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide or they can be within the peptide. A simple system is used to describe analogues of GLP-1: For example GLP-1 A8G (7-37 amino acids) designates a GLP-1 analogue wherein the naturally occurring alanine at position 8 has been substituted with a glycine residue. Formulae of peptide analogs and derivatives thereof are drawn using standard single letter abbreviation for amino acids used according to IUPAC-IUB nomenclature.

As used herein "fragment," when used in reference to a polypeptide, is a polypeptide having an amino acid sequence that is the same as part but not all of the amino acid sequence of the entire naturally occurring polypeptide. Fragments may be "free-standing" or comprised within a larger polypeptide of which they form a part or region as a single continuous region in a single larger polypeptide. By way of example, a fragment of naturally occurring GLP-1 would include amino acids 7 to 36 of naturally occurring amino acids 1 to 36. Furthermore, fragments of a polypeptide may also be variants of the naturally occurring partial sequence. For instance, a fragment of GLP-1 comprising amino acids 7-30 of naturally occurring GLP-1 may also be a variant having amino acid substitutions within its partial sequence.

Examples of suitable insulinotropic agents of the invention include GLP-1, GLP-1 derivatives, GLP-1 analogues, or a derivative of a GLP-1 analogue. In addition they include Exendin-4, Exendin-4 analogues and Exendin-4 derivatives or fragments and Exendin-3, Exendin-3 derivatives and Exendin-3 analogues.

The term "GLP-1" as used herein means GLP-1 (7-37), GLP-1 (7-36), GLP-1 (7-35), GLP-1 (7-38), GLP-1 (7-39), GLP-1 (7-40), GLP-1 (7-41), a GLP-1 analogue, a GLP-1 peptide, a GLP-1 derivative or mutant or fragment or a derivative of a GLP-1 analogue. Such peptides, mutants, analogues and derivatives are insulinotropic agents.

For example the GLP-1 can be GLP-1 (7-37) A8G mutant with the amino acid sequence shown in FIG. 1 (*i*): SEQ ID NO 9.

Further GLP-1 analogues are described in International Patent Application No. 90/11296 (The General Hospital Corporation) which relates to peptide fragments which comprise GLP-1 (7-36) and functional derivatives thereof and have an insulinotropic activity which exceeds the insulinotropic activity of GLP-1 (1-36) or GLP-1 (1-37) and to their use as insulinotropic agents (incorporated herein by reference, particularly by way of examples of drugs for use in the present invention).

International Patent Application No. WO 91/11457 (Buckley et al.) discloses analogues of the active GLP-1 peptides 7-34, 7-35, 7-36, and 7-37 which can also be useful as GLP-1 drugs according to the present invention.

The term "exendin-4 peptide" as used herein means exendin-4 (1-39), an exendin-4 analogue, a fragment of exendin-4 peptide, an exendin-4 derivative or a derivative of an exendin-4 analogue. Such peptides, fragments, analogues and derivatives are insulinotropic agents. The amino acid sequence of exendin-4 (1-39) is shown in FIG. 1 (j): SEQ ID NO 10.

Further Exendin-analogs that are useful for the present invention are described in PCT patent publications WO 99/25728 (Beeley et al.), WO 99/25727 Beeley et al.), WO 98/05351 (Young et al.), WO 99/40788 (Young et al.), WO 99/07404 (Beeley et al), and WO 99/43708 (Knudsen et al) (all incorporated herein by reference, particularly by way of examples of drugs for use in the present invention).

As used herein, "peptide" refers to about two to about 50 amino acids that are joined together via peptide bonds.

As used herein, "polypeptide" refers to at least about 50 amino acids that are joined together by peptide bonds. Polypeptides generally comprise tertiary structure and fold into functional domains.

As used herein, "display system" refers to a system in which a collection of polypeptides or peptides are accessible for selection based upon a desired characteristic, such as a physical, chemical or functional characteristic. The display system can be a suitable repertoire of polypeptides or peptides (e.g., in a solution, immobilized on a suitable support). The display system can also be a system that employs a cellular expression system (e.g., expression of a library of nucleic acids in, e.g., transformed, infected, transfected or transduced cells and display of the encoded polypeptides on the surface of the cells) or an acellular expression system (e.g., emulsion compartmentalization and display). Exemplary display systems link the coding function of a nucleic acid and physical, chemical and/or functional characteristics of a polypeptide or peptide encoded by the nucleic acid. When such a display system is employed, polypeptides or peptides that have a desired physical, chemical and/or functional characteristic can be selected and a nucleic acid encoding the selected polypeptide or peptide can be readily isolated or recovered. A number of display systems that link the coding function of a nucleic acid and physical, chemical and/or functional characteristics of a polypeptide or peptide are known in the art, for example, bacteriophage display (phage display, for example phagemid display), ribosome display, emulsion compartmentalization and display, yeast display, puromycin display, bacterial display, display on plasmid, covalent display and the like. (See, e.g., EP 0436597 (Dyax), U.S. Pat. No. 6,172,197 (McCafferty et al.), U.S. Pat. No. 6,489,103 (Griffiths et al.).)

As used herein, "functional" describes a polypeptide or peptide that has biological activity, such as specific binding activity. For example, the term "functional polypeptide" includes an antibody or antigen-binding fragment thereof that binds a target antigen through its antigen-binding site.

As used herein, "target ligand" refers to a ligand which is specifically or selectively bound by a polypeptide or peptide. For example, when a polypeptide is an antibody or antigen-binding fragment thereof, the target ligand can be any desired antigen or epitope. Binding to the target antigen is dependent upon the polypeptide or peptide being functional.

As used herein an antibody refers to IgG, IgM, IgA, IgD or IgE or a fragment (such as a Fab, F(ab')$_2$, Fv, disulphide linked Fv, scFv, closed conformation multispecific antibody, disulphide-linked scFv, diabody) whether derived from any species naturally producing an antibody, or created by recombinant DNA technology; whether isolated from serum, B-cells, hybridomas, transfectomas, yeast or bacteria.

As used herein, "antibody format" refers to any suitable polypeptide structure in which one or more antibody variable domains can be incorporated so as to confer binding specificity for antigen on the structure. A variety of suitable antibody formats are known in the art, such as, chimeric antibodies, humanized antibodies, human antibodies, single chain antibodies, bispecific antibodies, antibody heavy chains, antibody light chains, homodimers and heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab)$_2$ fragment), a single antibody variable domain (e.g., a dAb, $V_H$, $V_{HH}$, $V_L$), and modified versions of any of the foregoing (e.g., modified by the covalent attachment of polyethylene glycol or other suitable polymer or a humanized $V_{HH}$).

The phrase "immunoglobulin single variable domain" refers to an antibody variable domain ($V_H$, $V_{HH}$, $V_L$) that specifically binds an antigen or epitope independently of other V regions or domains. An immunoglobulin single variable domain can be present in a format (e.g., homo- or heteromultimer) with other variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" as the term is used herein. A "single immunoglobulin variable domain" is the same as an "immunoglobulin single variable domain" as the term is used herein. A "single antibody variable domain" is the same as an "immunoglobulin single variable domain" as the term is used herein. An immunoglobulin single variable domain is in one embodiment a human antibody variable domain, but also includes single antibody variable domains from other species such as rodent (for example, as disclosed in WO 00/29004, the contents of which are incorporated herein by reference in their entirety), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. The $V_{HH}$ may be humanized.

A "domain" is a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single antibody variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The term "library" refers to a mixture of heterogeneous polypeptides or nucleic acids. The library is composed of members, each of which has a single polypeptide or nucleic acid sequence. To this extent, "library" is synonymous with "repertoire." Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. In one embodiment, each individual organism or cell contains only one or a limited number of library members. In one embodiment, the nucleic acids are incorporated into expression vectors, in order to allow expression of the polypeptides encoded by the nucleic acids. In an aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of diverse polypeptides.

As used herein, the term "dose" refers to the quantity of fusion or conjugate administered to a subject all at one time (unit dose), or in two or more administrations over a defined time interval. For example, dose can refer to the quantity of fusion or conjugate administered to a subject over the course of one day (24 hours) (daily dose), two days, one week, two weeks, three weeks or one or more months (e.g., by a single administration, or by two or more administrations). The interval between doses can be any desired amount of time.

The phrase, "half-life," refers to the time taken for the serum or plasma concentration of the fusion or conjugate to reduce by 50%, in vivo, for example due to degradation and/or clearance or sequestration by natural mechanisms. The fusions or conjugates of the invention are stabilized in vivo and their half-life increased by binding to serum albumin molecules e.g. human serum albumin (HSA) which resist degradation and/or clearance or sequestration. These serum albumin molecules are naturally occurring proteins which themselves have a long half-life in vivo. The half-life of a molecule is increased if its functional activity persists, in vivo, for a longer period than a similar molecule which is not specific for the half-life increasing molecule. For example, a fusion or conjugate of the invention comprising a dAb specific for human serum albumin (HSA) and an incretin drug or insulinotropic agent such as GLP-1 or exendin is compared with the same ligand wherein the specificity to HSA is not present, that is does not bind HSA but binds another molecule. For example, it may bind a third target on the cell. Typically, the half-life is increased by 10%, 20%, 30%, 40%, 50% or more. Increases in the range of 2×, 3×, 4×, 5×, 10×, 20×, 30×, 40×, 50×, 100×, 200×, 300× or more of the half-life are possible. Alternatively, or in addition, increases in the range of up to 30×, 40×, 50×, 60×, 70×, 80×, 90×, 100×, 150×, 200×, 300×, 400× of the half-life are possible.

As used herein, "hydrodynamic size" refers to the apparent size of a molecule (e.g., a protein molecule, ligand) based on the diffusion of the molecule through an aqueous solution. The diffusion, or motion of a protein through solution can be processed to derive an apparent size of the protein, where the size is given by the "Stokes radius" or "hydrodynamic radius" of the protein particle. The "hydrodynamic size" of a protein depends on both mass and shape (conformation), such that two proteins having the same molecular mass may have differing hydrodynamic sizes based on the overall conformation of the protein.

Calculations of "homology" or "identity" or "similarity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In an embodiment, the length of a reference sequence aligned for comparison purposes is at least 30%, or at least 40%, or at least 50%, or at least 60%, or at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "homology" is equivalent to amino acid or nucleic acid "identity"). The percent identity between the two sequences is a function of the number of identical positions shared by the sequences, taking into account the number of gaps, and the length of each gap, which need to be introduced for optimal alignment of the two sequences. Amino acid and nucleotide sequence alignments and homology, similarity or identity, as defined herein may be prepared and determined using the algorithm BLAST 2 Sequences, using default parameters (Tatusova, T. A. et al., FEMS Microbiol Lett, 174:187-188 (1999).

Nucleic Acids, Host Cells:

The invention relates to isolated and/or recombinant nucleic acids encoding the fusions of the invention that are described herein e.g. those encoded by SEQ ID NOS 13-23.

Nucleic acids referred to herein as "isolated" are nucleic acids which have been separated away from other material (e.g., other nucleic acids such as genomic DNA, cDNA and/or RNA) in its original environment (e.g., in cells or in a mixture of nucleic acids such as a library). An isolated nucleic acid can be isolated as part of a vector (e.g., a plasmid).

Nucleic acids referred to herein as "recombinant" are nucleic acids which have been produced by recombinant DNA methodology, including methods which rely upon artificial recombination, such as cloning into a vector or chromosome using, for example, restriction enzymes, homologous recombination, viruses and the like, and nucleic acids prepared using the polymerase chain reaction (PCR).

The invention also relates to a recombinant host cell e.g. mammalian or microbial, which comprises a (one or more) recombinant nucleic acid or expression construct comprising a nucleic acid encoding a fusion of the invention as described herein. There is also provided a method of preparing a fusion of the invention as described herein, comprising maintaining a recombinant host cell e.g. mammalian or microbial, of the invention under conditions appropriate for expression of the fusion polypeptide. The method can further comprise the step of isolating or recovering the fusion, if desired.

For example, a nucleic acid molecule (i.e., one or more nucleic acid molecules) encoding a fusion polypeptide of the invention, or an expression construct (i.e., one or more constructs) comprising such nucleic acid molecule(s), can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g., in the presence of an inducer, in a suitable animal, in suitable culture media supplemented with appropriate salts, growth factors, antibiotics, nutritional supplements, etc.), whereby the encoded peptide or polypeptide is produced. If desired, the encoded peptide or polypeptide can be isolated or recovered (e.g., from the animal, the host cell, medium, milk). This process encompasses expression in a host cell of a transgenic animal (see, e.g., WO 92/03918, GenPharm International).

The fusion polypeptides of the invention described herein can also be produced in a suitable in vitro expression system, e.g. by chemical synthesis or by any other suitable method.

As described and exemplified herein, the fusions or conjugates of the invention generally bind serum albumin with high affinity.

For example, the fusions or conjugates of the invention can bind human serum albumin with an affinity (KD; KD=$K_{off}$ (kd)/$K_{on}$ (ka) [as determined by surface plasmon resonance) of about 5 micromolar to about 100 pM, e.g. about 1 micromolar to about 100 pM e.g. about 5-50 nm e.g. about 10-30 nm, e.g. about 20-30 nm.

The fusion or conjugates of the invention can be expressed in *E. coli* or in *Pichia* species (e.g., *P. pastoris*) and they can also be expressed in any yeast or fungal cells. In one embodiment, the fusion is secreted in a quantity of at least about 0.5 mg/L when expressed in *E. coli* or in *Pichia* species (e.g., *P. pastoris*); or in mammalian cell culture (e.g. CHO, or HEK 293 cells). Although, the fusions or conjugates described herein can be secretable when expressed in *E. coli* or in *Pichia* species or mammalian cells they can be produced using any suitable method, such as synthetic chemical methods or biological production methods that do not employ *E. coli* or *Pichia* species.

In certain embodiments, the fusions and conjugates of the invention are efficacious in animal models of such as those described in WO 2006/059106 (e.g. at pages 104-105 of published WO 2006/059106) or those described in the examples herein, when an effective amount is administered. Generally an effective amount is about 0.0001 mg/kg to about 10 mg/kg (e.g., about 0.001 mg/kg to about 10 mg/kg, e.g. about 0.001 mg/kg to about 1 mg/kg, e.g. about 0.01 mg/kg to about 1 mg/kg, e.g. about 0.01 mg/kg to about 0.1 mg/kg) The models of disease are recognized by those skilled in the art as being predictive of therapeutic efficacy in humans.

Generally, the present fusions and conjugates of the invention will be utilised in purified form together with pharmacologically or physiologically appropriate carriers. Typically, these carriers can include aqueous or alcoholic/aqueous solutions, emulsions or suspensions, any including saline and/or buffered media. Parenteral vehicles can include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) *Remington's Pharmaceutical Sciences,* 16th Edition). A variety of suitable formulations can be used, including extended release formulations.

The route of administration of pharmaceutical compositions according to the invention may be any of those commonly known to those of ordinary skill in the art. For therapy, the drug fusions or conjugates of the invention can be administered to any patient in accordance with standard techniques.

The administration can be by any appropriate mode, including parenterally, intravenously, intramuscularly, intraperitoneally, orally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician. Administration can be local or systemic as indicated.

In one embodiment, the invention provides a pulmonary formulation for delivery to the lung which comprises (a) the conjugates or fusions of the invention, and (b) a pharmaceutically acceptable buffer, and wherein the composition comprises liquid droplets and about 40% or more e.g. 50% or more, of the liquid droplets present in the composition have a size in the range which is less than about 6 microns e.g. from about 1 micron to about 6 microns e.g. less than about 5 microns e.g. about 1 to about 5 microns These compositions are e.g. especially suitable for administration to a subject by direct local pulmonary delivery. These compositions can, for example, be administered directly to the lung, e.g. by inhalation, for example by using a nebuliser device. These compositions for pulmonary delivery can comprise a physiologically acceptable buffer, which has a pH range of between about 4 to about 8, e.g. about 7 to about 7.5, and a viscosity which is about equal to the viscosity of a solution of about 2% to about 10% PEG 1000 in 50 mM phosphate buffer containing 1.2% (w/v) sucrose.

The fusions or conjugates of this invention can be lyophilised for storage and reconstituted in a suitable carrier prior to use. This technique has been shown to be effective with conventional immunoglobulins and art-known lyophilisation and reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate.

For prophylactic applications, e.g. when administering to individuals with pre-diabetes or with insulin resistance, compositions containing the present fusions or conjugates may also be administered in similar or slightly lower dosages, to prevent, inhibit or delay onset of disease (e.g., to sustain remission or quiescence, or to prevent acute phase). The skilled clinician will be able to determine the appropriate dosing interval to treat, suppress or prevent disease. When a fusion or conjugate of the invention is administered to treat, suppress or prevent disease, it can be administered up to four times per day, twice weekly, once weekly, once every two weeks, once a month, or once every two months, at a dose of, for example about 0.0001 mg/kg to about 10 mg/kg (e.g., about 0.001 mg/kg to about 10 mg/kg e.g. about 0.001 mg/kg to about 1 mg/kg e.g. about 0.01 mg/kg to about 1 mg/kg, e.g. about 0.01 mg/kg to about 0.1 mg/kg).

Treatment or therapy performed using the compositions described herein is considered "effective" if one or more symptoms are reduced (e.g., by at least 10% or at least one point on a clinical assessment scale), relative to such symptoms present before treatment, or relative to such symptoms in an individual (human or model animal) not treated with such composition or other suitable control. Symptoms will obviously vary depending upon the precise nature of the disease or disorder targeted, but can be measured by an ordinarily skilled clinician or technician.

Similarly, prophylaxis performed using a composition as described herein is "effective" if the onset or severity of one or more symptoms is delayed, reduced or abolished relative to such symptoms in a similar individual (human or animal model) not treated with the composition.

The fusions and conjugates of the present invention may be used as separately administered compositions or they may be administered in conjunction with other therapeutic or active agents e.g. other polypeptides or peptides or small molecules. These further agents can include various drugs, such as for example metformin, insulin, glitazones (e.g. rosaglitazone), immunosuppresives, immunostimulants.

The fusions and conjugates of the invention can be administered and/or formulated together with one or more additional therapeutic or active agents. When a fusion or conjugate of the invention is administered with an additional therapeutic agent, the fusion or conjugate can be administered before, simultaneously, with, or subsequent to administration of the additional agent. Generally, the fusion or conjugate of the invention and the additional agent are administered in a manner that provides an overlap of therapeutic effect.

Half Life:

Increased half-life of the insulinotropic agent or incretin drug e.g. the GLP-1 or exendin ligand is useful in in vivo applications. The invention solves this problem by providing increased half-life of the insulinotropic agent or incretin drug e.g. GLP and exendin, in vivo and consequently longer persistence times in the body of the functional activity of these molecules.

As described herein, compositions of the invention (i.e. comprising the fusions or conjugates described herein) can have dramatically prolonged in vivo serum or plasma half-life and/or increased AUC and/or increased mean residence time (MRT), as compared to insulinotropic agent or incretin drug alone. In addition, the activity of the insulinotropic agent or incretin drug is generally not substantially altered in the composition of the invention (e.g., the conjugate, or the fusion). However, some change in the activity of compositions of the invention compared to insulinotropic agent or incretin drug alone is acceptable and is generally compensated for by the improved pharmacokinetic properties of the conjugates or fusions of the invention. For example, drug conjugates or fusions of the invention may bind the drug target with lower affinity than drug alone, but have about equivalent or superior efficacy in comparison to drug alone due to the improved pharmacokinetic properties (e.g., prolonged in vivo serum half-life, larger AUC) of the drug composition. In addition, due to the increased half life the conjugates or fusions of the invention they can be administered less frequently than the insulinotropic agent or incretin drug alone e.g. they can be given to patients once a month or once a week, and they also attain a more constant level of insulinotropic agent or incretin drug in the blood than administration of insulinotropic agent or incretin drug alone, so achieving the desired therapeutic or prophylactic effect.

Methods for pharmacokinetic analysis and determination of ligand half-life will be familiar to those skilled in the art. Details may be found in Kenneth, A et al: Chemical Stability of Pharmaceuticals: A Handbook for Pharmacists and in Peters et al, Pharmacokinetic analysis: A Practical Approach (1996). Reference is also made to "Pharmacokinetics", M Gibaldi & D Perron, published by Marcel Dekker, $2^{nd}$ Rev. ex edition (1982), which describes pharmacokinetic parameters such as t alpha and t beta half lives and area under the curve (AUC).

Half lives (t½ alpha and t½ beta) and AUC and MRT can be determined from a curve of plasma or serum concentration of ligand against time. The WinNonlin analysis package (available from Pharsight Corp., Mountain View, Calif. 94040, USA) can be used, for example, to model the curve. In a first phase (the alpha phase) the ligand is undergoing mainly distribution in the patient, with some elimination. A second phase (beta phase) is the terminal phase when the ligand has been distributed and the serum concentration is decreasing as the ligand is cleared from the patient. The t alpha half life is the half life of the first phase and the t beta half life is the half life of the second phase. In addition a non-compartmental fitting model that is well known in the art can also be used to determine half life.

In one embodiment, the present invention provides a fusion or conjugate according to the invention that has an elimination half-life e.g. in human subjects, in the range of about 12 hours or more, e.g. about 12 hours to about 21 days, e.g. about 24 hours to about 21 days, e.g. about 2-10 days e.g. about 3-4 days.

The fusions or conjugates of the invention can also be further formatted to have a larger hydrodynamic size, for example, by attachment of a PEG group, serum albumin, transferrin, transferrin receptor or at least the transferrin-binding portion thereof, an antibody Fc region, or by conjugation to an antibody domain.

Hydrodynamic size may be determined using methods which are well known in the art. For example, gel filtration chromatography may be used to determine the hydrodynamic size of a ligand. Suitable gel filtration matrices for determining the hydrodynamic sizes of ligands, such as cross-linked agarose matrices, are well known and readily available.

Compositions of the invention, i.e. those comprising the fusions and conjugates described herein, provide several further advantages. The Domain antibody component is very stable, is small relative to antibodies and other antigen-binding fragments of antibodies, can be produced in high yields by expression in E. coli or yeast (e.g., Pichia pastoris), and antigen-binding fragments of antibodies that bind serum albumin can be easily selected from libraries of human origin or from any desired species. Accordingly, compositions of the invention that comprise the dAb that binds serum albumin can be produced more easily than therapeutics that are generally produced in mammalian cells (e.g., human, humanized or chimeric antibodies) and dAbs that are not immunogenic can be used (e.g., a human dAb can be used for treating or diagnosing disease in humans).

The immunogenicity of the insulinotropic agent or incretin drug can be reduced when the insulinotropic agent or incretin is part of a drug composition that contains a dAb binds serum albumin. Accordingly, the invention provides a fusion or conjugate compositions which can be less immunogenic (than e.g. the insulinotropic agent or incretin alone) or which can be substantially non-immunogenic in the context of a drug composition that contains a dAb that binds serum albumin. Thus, such compositions can be administered to a subject repeatedly over time with minimal loss of efficacy due to the elaboration of anti-drug antibodies by the subject's immune system.

Additionally, the conjugate or fusion compositions described herein can have an enhanced safety profile and fewer side effects than the insulinotropic agent or incretin alone. For example, as a result of the serum albumin-binding activity of the dAb, the fusions and conjugates of the invention have enhanced residence time in the vascular circulation. Additionally, the fusions and conjugates of the invention are substantially unable to cross the blood brain barrier and to accumulate in the central nervous system following systemic administration (e.g., intravascular administration). Accordingly, the fusions or conjugates of the invention can be administered with greater safety and reduced side effects in comparison to the insulinotropic agent or incretin drug alone. Similarly, the fusions or conjugates can have reduced toxicity toward particular organs (e.g., kidney or liver) than drug alone.

EXAMPLES

Example 1

Expression of Genetic Fusions of GLP-1 (A8G) or Exendin-4 and DOM7h-14 AlbudAb

Either exendin-4 or GLP-1 (7-37), with alanine at position 8 replaced by glycine ([Gly$^8$] GLP-1), was cloned as a fusion with DOM7h-14 (a domain antibody (dAb) which binds serum albumin (AlbudAb) with an amino acid sequence shown below) into the pTT-5 vector (obtainable from CNRC, Canada). In each case the GLP-1 or exendin-4 was at the 5' end of the construct and the dAb at the 3' end. In total, 7 constructs (DAT0114, DAT 0115, DAT0116, DAT 0117, DAT 0118, DAT 0119, DAT 0120) were made with the amino acid sequences shown in FIG. 1 (A-G). There was either no linker, a gly-ser linker (G4S), or a helical linker (Arai, R., H. Ueda, et al. (2001). "Design of the linkers which effectively separate domains of a bifunctional fusion protein." Protein Eng 14(8): 529-32.456) or a linker composed of a second GLP-1 moiety between the GLP-1 or exendin-4 and the dAb. The linkers were included as spacers to separate the GLP-1 or exendin-4 spatially from the dAb to prevent steric hindrance of the binding between the GLP-1 or exendin-4 and the GLP-1 receptor. The sequences of the constructs are shown in FIG. 1 (A-G).

Endotoxin free DNA was prepared in *E. coli* using alkaline lysis (using the endotoxin free plasmid Giga kit, obtainable from Qiagen CA) and used to transfect HEK293E cells (obtainable from CNRC, Canada). Transfection was into 250 ml/flask of HEK293E cells at $1.75 \times 10^6$ cells/ml using 333 ul of 293fectin (Invotrogen) and 250 ug of DNA per flask and expression was at 30° C. for 5 days. The supernatant was harvested by centrifugation and purification was by affinity purification on protein L. Protein was batch bound to the resin, packed on a column and washed with 10 column volumes of PBS. Protein was eluted with 50 ml of 0.1M glycine pH2 and neutralised with Tris pH8. Protein of the expected size was identified on an SDS-PAGE gel and sizes are shown in the table 1 below

TABLE 1

Molecular weights of DAT0114, DAT 0115, DAT0116, DAT 0117, DAT 0118, DAT 0119, DAT 0120

| Fusion protein | Expected MW |
| --- | --- |
| DAT0114 | 18256 |
| DAT0115 | 16896 |
| DAT0116 | 15950 |
| DAT0117 | 19798 |
| DAT0118 | 15936 |
| DAT0119 | 15318 |
| DAT0120 | 18895 |

Example 2

Showing that GLP-1 and Exendin-4 AlbudAb Fusions Bind Serum Albumin

GLP-1 and Exendin-4 AlbudAb fusions were analysed by surface plasmon resonance (Biacore AB obtainable from GE Healthcare) to obtain information on affinity. The analysis was performed using a CM5 Biacore chip (carboxymethylated dextran matrix) that was coated with serum albumin. About 1000 resonance units (RUs) of each serum albumin to be tested (human, rat and mouse serum albumin) was immobilised in acetate buffer pH 5.5. Flow cell 1 of the Biocore AB was an uncoated, blocked negative control, flow cell 2 was coated with Human serum albumin (HSA) (815 RUs) flow cell 3 was coated with Rat serum albumin (RSA)(826RUs) and flow cell 4 was coated with Mouse serum albumin (MSA) (938 RUs). Each fusion molecule tested was expressed in mammalian tissue culture as described in the example above.

A range of concentrations of the fusion molecule were prepared (in the range 16 nM to 2 µM) by dilution into BIACORE HBS-EP buffer (0.01M HEPES, pH7.4, 0.15M NaCl, 3 mM EDTA, 0.005% surfactant P20) and flowed across the BIACORE chip.

Affinity (KD) was calculated from the BIACORE traces by fitting on-rate and off-rate curves to traces generated by concentrations of dAb in the region of the KD. Affinities (KD) are summarised in the following table 2:

TABLE 2

Binding of GLP-1 and exendin-4 AlbudAb to human, rat and mouse serum albumins

|  | GLP-1 (7-37) A8G, helical linker, DOM7h-14 fusion | 2xGLP-1 (7-37) A8G DOM7h-14 fusion |
| --- | --- | --- |
| HSA | 110 nM | 150 nM |
| RSA | 800 nM | 700 nM |
| MSA | 110 nM | 130 nM |

The results above demonstrate that the fusion molecules retain the ability to bind to all types of serum albumin and this indicates that they are likely to have an extended half life in vivo.

Example 3

GLP-1 and Exendin-4 AlbudAb Fusions are Active in a GLP-1 Receptor Binding Assay (GLP-1R BA)

Fusions were buffer exchanged into 100 mM NaVl, 20 mM citrate pH 6.2. Meanwhile, CHO 6CRE GLP1R cells (CHO K1 cells (obtainable from the American Type Tissue Collection, ATCC) stably transfected with 6 cAMP response element driving a luciferase reporter gene and also with the human GLP-1 receptor) were seeded at $2 \times 10^5$ cells/mL in suspension media. Suspension culture was maintained for 24 hours. Cells were then diluted into 15 mM HEPES buffer (obtainable from Sigma), containing 2 mM L glutamine ($2.5 \times 10^5$ cells/ml) and dispensed into 384-well plates containing 10 ul/well of the compound to be assayed. After the addition of assay control, plates were returned to the incubator for 3 h at 37° C. and 5% CO2. After the incubation, steady glo luciferase substrate (obtainable from Promega) was added to the wells as described in the kit and the plates sealed with self-adhesive plate seals (Weber Marking Systems Inc. Cat. No. 607780). Plates were placed in the reader (Viewlux, Perkin Elmer) and pre-incubated for 5 minutes prior to reading the fluorescence and plotting of results. Compound was assayed at a range of concentrations in the presence and absence of 10 uM albumin, allowing a dose response curve to be fitted with and without the albumin. EC50s were calculated and are summarised in the following table 3:

TABLE 3

Activity of GLP-1 and exendin-4 AlbudAb fusions in a GLP-1 receptor binding assay (GLP-1R BA)

|  | GLP-1R BA $EC_{50}$ (pM) n = 3 | GLP-1R BA (10 uM albumin) $EC_{50}$ (pM) n = 2 |
| --- | --- | --- |
| Exendin 4 (G4S)3 DOM7h-14 fusion | 8.9 | 35 |
| Exendin 4 DOM7h-14 fusion | 12 | 72 |

TABLE 3-continued

Activity of GLP-1 and exendin-4 AlbudAb fusions in a GLP-1 receptor binding assay (GLP-1R BA)

| | GLP-1R BA $EC_{50}$ (pM) n = 3 | GLP-1R BA (10 uM albumin) $EC_{50}$ (pM) n = 2 |
|---|---|---|
| Exendin 4, helical linker, DOM7h-14 fusion | 4.3 | 15 |
| GLP-1 A8G, helical linker, DOM7h-14 fusion | 17 | 130 |
| GLP-1 7-36 | 21 | 19 |
| Exendin-4 | 1.0 | 0.82 |

The results above demonstrate that all of the fusion molecules tested retain potency for binding to the GLP-1 receptor. The results also demonstrate that this potency is retained in the presence of serum albumin. Hence, these fusion molecules are likely to retain the ability to bind the GLP-1 receptor in vivo.

Example 4

Expression of DAT0115, DAT0116, DAT0117 and DAT0120 in HEK 293 Mammalian Tissue Culture followed by Purification by Protein L Affinity Capture and Ion Exchange Chromatography The aim of this experiment was to produce protein for in vivo and in vitro characterisation. Protein was expressed in mammalian tissue culture in HEK 293E cells from the pTT-5 vector as described in the previously. Briefly, endotoxin free DNA was prepared and purified and used to transfect HEK293E cells. Protein expression was for 5 days at 30° C. in a shaking incubator and cultures were spun down and supernatant (containing the protein of interest) harvested. Protein was purified from the supernatant by affinity capture on protein L agarose streamline affinity resin (resin GE Healthcare, protein L coupled in house). Resin was then washed with 10 column volumes of PBS and then protein was eluted with 5 column volumes of 0.1 M glycine pH2.0. Neutralisation was with 1 column volume of 1M Tris glycine pH8.0. In this case (contrasting with the previous example), further purification was then undertaken. Protein (in tris-glycine) was buffer exchanged to 20 mM acetate pH 5.0 prior to loading using the Akta onto 1 (or 2 in parallel) 6 ml resource S columns (GE healthcare) pre-equilibrated in 20 mM acetate pH 5.0. After washing with the same buffer, protein was eluted via a 0-0.75M or 0-1M NaCl gradient in 20 mM acetate pH5.0. Fractions of the correct size were then identified by SDS-PAGE electrophoresis and by mass spectrometry and were then combined to make the final protein sample. Protein was then buffer exchanged into 20 mM citrate, pH6.2, 100 mM NaCl and concentrated to between 0.5 and 5 mg/ml. Protein was filtered through a 0.2 uM filter to ensure sterility. Protein was then used in examples described below.

Example 5

Comparison of the Stability of DAT0115, DAT0116, DAT0117 and DAT0120 to 1, 3 and 6 Freeze Thaw Cycles The aim of this study was to compare the stability of DAT0115, DAT0116, DAT0117 and DAT0120 to 1, 3 and 6 freeze thaw cycles. Each protein was expressed in mammalian tissue culture in HEK 293E cells from the pTT-5 vector and purified on protein L affinity resin followed by ion exchange chromatography as described above. Protein was buffer exchanged into 20 mM citrate, 100 mM NaCl and diluted to 0.5 mg/ml using the same buffer. 0.5 ml aliquots of each protein (in eppendorf tubes) were then subjected to 0, 1, 3 or 6 freeze thaw cycles, with each cycle comprising 3 minutes on dry ice followed by 2 minutes in a 37° C. water bath. (It was observed during the experiment that 2 minutes at 37° C. was sufficient for the protein solution to completely thaw.) After completion of the requisite number of freeze-thaw cycles, protein samples were stored at 2-8° C. until further analysis. Proteins were then subjected to analysis by SDS PAGE electrophoresis, GLP-1R binding assay, size exclusion chromatography on a Superdex 75 column and mass spectrometry. It was observed that SDS-PAGE profile, potency by GLP-1R BA and mass spec profile of all four protein was not significantly changed from baseline by 1, 3 or 6 freeze-thaw cycles. Maximum peak height in the SEC analysis was affected with 78%, 86%, 104% and 57% of maximum height maintained after 6 freeze thaw cycles for DAT0115, DAT-116, DAT0117 and DAT0120 respectively. It was concluded that DAT0120 was less stable to freeze thaw cycles than the other three proteins.

TABLE 4

Results of comparison of the stability of DAT0115, DAT0116, DAT0117 and DAT0120 to 1, 3 and 6 freeze thaw cycles

| Sample | Number of freeze thaw cycles | Peak height (mAU) | % max peak height |
|---|---|---|---|
| DAT0115 | 0 | 49 | 100% |
| DAT0115 | 1 | 43 | 89% |
| DAT0115 | 3 | 40 | 82% |
| DAT0115 | 6 | 38 | 78% |
| DAT0116 | 0 | 29 | 100% |
| DAT0116 | 1 | 28 | 95% |
| DAT0116 | 3 | 26 | 91% |
| DAT0116 | 6 | 25 | 86% |
| DAT0117 | 0 | 34 | 100% |
| DAT0117 | 1 | 34 | 99% |
| DAT0117 | 3 | 35 | 103% |
| DAT0117 | 6 | 35 | 104% |
| DAT0120 0 | 0 | 35 | 100% |
| DAT0120 1 | 1 | 24 | 70% |
| DAT0120 3 | 3 | 21 | 59% |
| DAT0120 6 | 6 | 20 | 57% |

Example 6

Demonstration of the Duration of Action of DAT0115 in the db/db Mouse Model of Tune II Diabetes The aim of this study was to determine the duration of action of DAT0115 on oral glucose tolerance in db/db mice. Animals were sorted by decreasing glucose levels three days prior to the start of the experiment and then blocked. One animal within each block was then assigned to each of the 26 study groups. This ensured similar mean starting glucose level in each of the study groups.

DAT0115 (produced in HEK293 cells and purified as described above) was administered subcutaneously at 1 mg/Kg, 0.3 mg/Kg or 0.1 mg/Kg either 5 h, 24 h, 48 h, 72 h, 96 h or 120 h hours prior to the oral glucose load. (Not all doses were administered at every timepoint, see table below for details.) DAT0115 significantly decreased the glucose AUC over the 2 hour time period of the oral-glucose tolerance test (OGTT) compared to vehicle treated db/db mice at timepoints out to and including 24 h for the 0.1 mg/Kg and 0.3 mg/Kg doses and out to and including the 72 h timepoint for the 1 mg/Kg dose. Exendin-4, administered as a positive control at 42 µg/Kg, also significantly reduced the glucose AUC following OGTT when administered 5 h prior to the oral glucose bolus. The table 5 below shows the percentage reduction in AUC for each of the DAT0115 study groups compared to vehicle. An asterisk indicates P<0.05 for DAT0115 comparison to vehicle using the false discovery rate correction.

TABLE 5 showing the percentage reduction in AUC for each of the DAT0115 study groups compared to vehicle. (An asterisk indicates P < 0.05 for DAT0115 comparison to vehicle using the false discovery rate correction)

| OGTT Time (hrs relative to dosing) | 0.1 mg/kg DAT0115 | 0.3 mg/kg DAT0115 | 1 mg/kg DAT0115 |
|---|---|---|---|
| +5 | 60%* | Not done | 76%* |
| +24 | 36%* | 59%* | 50%* |
| +48 | 28% | 26% | 37%* |
| +72 | 16% | 26% | 41%* |
| +96 | −12% | Not done | 12% |

Example 7

Demonstration of Efficacy of DAT0115 in the Diet Induced Obese (DIO) Mouse Model of Obesity The aim of this study was to use an established mouse feeding model (diet induced obese mice) to determine whether food consumption and, as a result, body weight is affected by treatment with DAT0115. This may be predictive for humans. Male C57Bl/6 mice (purchased from Taconic) were fattened on 60% kcal high fat irradiated diet for 12 wks and then transferred to the in-house facility. Upon arrival, the mice were individually housed on alpha-dri bedding in a temperature and humidity controlled room (70-72° F., Humidity=48-50%, 5 AM/5 PM light cycle). The diet was changed to 45% high fat diet and the animals acclimated for 18 days. Prior to administration of test compound, mice were injected subcutaneously with saline once daily for three days and food consumption monitored. Mice were blocked and grouped such that body weight and food consumption were not different between or within groups. On the day of the study, groups of 8 mice were dosed subcutaneously as follows using a 5 ml/kg injection volume: Three groups were dosed with DAT0115 (low, medium and high dose), one group with a negative control molecule (DOM7h-14 AlbudAb, but with no exendin-4 conjugate) and one with exendin-4 positive control.

TABLE 6

Protocol for Establishing Efficacy of DAT0115 in the diet induced obese (DIO) mouse model of obesity

| Group | Compound administered | Dose level |
|---|---|---|
| 1 | Negative control: DOM7h-14 in 100 mM NaCl, 20 mM citrate/sodium citrate pH 6.2 | 1 mg/Kg |
| 2 | Exendin-4 | 0.01 mg/Kg |
| 3 | DAT0115 in 100 mM NaCl, 20 mM citrate/sodium citrate pH 6.2 | 0.01 mg/Kg |
| 4 | DAT0115 in 100 mM NaCl, 20 mM citrate/sodium citrate pH 6.2 | 0.1 mg/Kg |
| 5 | DAT0115 in 100 mM NaCl, 20 mM citrate/sodium citrate pH 6.2 | 1 mg/Kg |

Daily food consumption and body weight were measured daily for 10 days. DAT0115 showed dose dependent reduction in body weight and food consumption compared to the DOM7h-14 control (see FIGS. 3a and 3b). It was therefore concluded that the data from this mouse study supports the hypothesis that DAT0115 would be a good clinical candidate.

Example 8

Determination of the plasma half life of DAT0115, DAT0116 and DAT0117 in a mouse model of tune II diabetes The aim of this study was to determine a plasma elimination profile for DAT0115, DAT0116 and DAT0117 in a mouse model of type II diabetes (db/db mice) and to calculate PK parameters from the results. DAT0115, DAT0116 and DAT0117 protein was prepared as described earlier: Briefly, protein was expressed in mammalian tissue culture using HEK293E cells and purified using batch absorption to protein L-agarose affinity resin followed by elution with glycine at pH 2.0 and neutralisation with Tris PH 8.0. This was followed by ion exchange chromatography on a Resource S column using a 0-1M salt gradient in 20 mM acetate pH5.0. Fractions containing the desired protein were then combined and buffer exchanged into 100 mM NaCl, 20 mM citrate pH6.2. Protein was filter sterilised, buffer exchanged and endotoxin removed ant tested prior to use in vivo.

Groups of non-fasted male db/db mice (LEPr db homozygous mice deficient for the leptin receptor with mutations in the leptin receptor gene (lepr)) were dosed either subcutaneously or intravenously with 1 mg/Kg DAT0115, DAT0116 or DAT0117. At predose, 0.25, 0.5, 1, 4, 7, 12, 24, 36, 48 and 60 hours after dosing for the iv doses and predose, 0.5, 1, 4, 7, 12, 24, 36, 48 and 60 hours after dosing for the sc doses blood samples were collected by terminal bleed and plasma prepared. Plasma samples were frozen and later defrosted for analysis of DAT0115, DAT0116 or DAT0117 levels as appropriate by solid phase extraction and LC/MS/MS to detect the presence of a fragment of the protein (from the exendin-4 section of the protein). Calculated plasma levels were then used to fit pharmacokinetic parameters using WinNonLin software. Half life after subcutaneous and intravenous administration and bioavailability is outlined in the table below. It was concluded from the results (see table 7 below) that all three compounds show desirable pharmacokinetic parameters in a mouse model of type II diabetes. Therefore, these molecules show the potential for good PK parameters in diabetic humans, with this study favoring the choice of DAT0115 or DAT0116 over DAT0117.

TABLE 7

Plasma half life of DAT0115, DAT0116 and DAT0117 in a mouse model of type II diabetes

| Compound | Half-life after intravenous administration | Half-life after subcutaneous administration | Bioavailability |
|---|---|---|---|
| DAT0115 | 13.8 | 18.6 | 65% |
| DAT0116 | 14.3 | 20.1 | 61% |
| DAT0117 | 11.4 | 11.2 | 25% |

Example 9

Determination of the Plasma Half Life of DAT0115, DAT0116, DAT0117 in Rat

The aim of this study was to determine a plasma elimination profile for DAT0115, DAT0116 and DAT0117 in rat and to calculate PK parameters from the results. DAT0115, DAT0116 and DAT0117 protein was prepared as described earlier: Briefly, protein expressed in mammalian tissue culture using HEK293E cells and purified using batch absorption to protein L-agarose affinity resin followed by elution with glycine at pH 2.0 and neutralisation with Tris pH 8.0. This was followed by ion exchange chromatography on a Resource S column using a 0-1M salt gradient in 20 mM acetate pH5.0. Fractions containing the desired protein were then combined and buffer exchanged into 100 mM NaCl, 20 mM citrate pH6.2. Protein was filter sterilised, buffer exchanged and Qced prior to use in vivo.

In order to determine plasma half life, groups of 3 rats were given a single i.v or s.c. injection at 0.3 mg/Kg (iv) or 1.0 mg/Kg (sc) of DAT0115, DAT0116 or DAT0117. Plasma samples were obtained by serial bleeds from a tail vein over a 72 h period and analyzed by LC/MS/MS to detect the presence of a fragment of the fusion (from the exendin-4 section of the fusion). Calculated plasma levels were then used to fit pharmacokinetic parameters using WinNonLin software. Half life after subcutaneous and intravenous administration and bioavailability is outlined in the table 8 below. It was concluded from the results that all three compounds show desirable pharmacokinetic parameters in rat. Therefore, all these molecules show the potential for good PK parameters in humans, with this study favoring the choice of DAT0115 over DAT0116 or DAT0117.

TABLE 8

Half life after subcutaneous and intravenous administration and bioavailability

| Compound | Half-life after intravenous administration | half life after subcutaneous administration | Bioavailability |
|---|---|---|---|
| DAT0115 | 4.9 h | 11.1 h | 81% |
| DAT0116 | 4.1 h | 8.7 h | 32% |
| DAT0117 | 4.9 h | 10.2 h | 15% |

Example 10

Determination of the Plasma Half Life of DAT0115 in Cynomolgus Monkey

The aim of this study was to determine the pharmacokinetic parameters for DAT0115 in a non human primate (cynomolgus monkey) to enable allometric scaling of parameters and give the best possible indication of whether DAT0115 was likely to have a good PK profile in humans. DAT0115 Exendin-4 AlbudAb fusion was expressed in HEK293E cells in mammalian tissue culture and purified as described earlier. Briefly, protein was purified using batch absorption to protein L-agarose affinity resin followed by elution with glycine at pH 2.0 and neutralisation with Tris PH 8.0. This was followed by ion exchange chromatography on a Resource S column using a 0-1M salt gradient in 20 mM acetate pH5.0. Fractions containing the desired protein were then combined and buffer exchanged into 100 mM NaCl, 20 mM citrate pH6.2.

Protein was extensively QCed (including SDS-PAGE, mass spec, activity assay:GLP-1R-BA, pH check, osmolarity check), filter sterilised and endotoxin removed. Protein with confirmed low endotoxin (<0.05 EU/mg protein) was then used for the in vivo study.

Six female cynomolgus monkeys (Macaca fascicularis; Charles River Laboratories BRF, Houston, Tex., Primate Products, Miami, Fla. and/or Covance Research Products, Inc., Alice, Tex.) were used in this study. The monkeys were approximately 2 to 9 years old (with a body weight range of approximately 2 to 5 kilograms) at initiation of dosing. The monkeys were housed individually in stainless steel cages in an environmentally controlled room(s) (64F to 84F; 30 to 70% relative humidity) with a 12-hour light/dark cycle. The female monkeys were offered approximately 6 biscuits twice daily of Monkey Diet #5038 (PMI Nutrition International, Richmond, Ind.) and a daily allotment of fresh fruit. Each animal was administered the test compound (DAT0115) either subcutaneously or intravenously according to dose group (3 sc and 3 iv). Dose was at 0.1 mg/Kg. On the days of dosing, the first feeding occurred within approximately 1 hour post dose for each monkey (extended up to 2.5 hours post dose if study-related procedures required animals to be out of their local housing for an extended period of time). The second feeding was no sooner than two hours following the first feeding. For the purpose of environmental enrichment, additional fruit, legume and/or vegetable (e.g., grapes, baby carrots, peanuts) was provided to each monkey at or around the time of viability check or as a method of reward after acclimation or study related procedures. Filtered tap water (supplied by Aqua Pennsylvania, Inc. and periodically analyzed) was available ad libitum.

Plasma samples (approx 2 ml) were collected from the femoral vessel at predose (0 hour) and nominally at 5 minutes (iv group only), 0.5, 4, 8, 24, 48, 96, 144, 192, 288, 336, 504 and 672 hours after dosing. (PK samples from one of the animals in the iv dose group were only collected to 24 h so this animal has been excluded from the PK fitting). Analysis of samples was by mass spectrometry, and fitting of the data was using WinNonLin fitting software. PK parameters were as follows for iv administration (n=2): $T_{1/2}$ 67 h, MRT 46 h, Vz 327 ml/Kg and Cl 3.3 ml/hr/Kg; and for sc administration (n=3): $T_{1/2}$ 68 h, MRT 98 h, Vz 306 ml/Kg and Cl 3.1 ml/hr/Kg. Bioavailability was calculated as 99%.

It was concluded from this study (and from biacore binding data to cyno and human serum albumin) that the 68 h sc half life of DAT0115 in cyno (as described above) gives confidence that the half life of the same molecule in humans is likely to be sufficiently long to correlate with a requirement for weekly (or less frequent) dosing.

Example 11

Determination of PD of DAT0115 in Cynomolgus Monkey

A PK study was conducted in cynomolgus monkey as described above. The principal aim of this study was to determine the pharmacokinetic parameters for DAT0115 in cynomolgus monkey (as described in the previous example), but a secondary aim was to obtain an indication of the efficacy of the DAT0115 compound in the monkeys (without sufficient power in the study for statistical significance). To achieve this secondary aim, biscuit consumption by the monkeys was monitored during the course of the study. It was noted in the days following dosing that there was a trend towards reduction in food consumption in all of the monkeys. It was concluded that this was probably due to the well documented effect of the exendin-4 part of the molecule as an appetite suppressant. Hence, DAT0115 is shown to be active in vivo. To ensure welfare of the animals fruit and treats were consumed on most days despite biscuit consumption.

TABLE 9

Measurement of Biscuits consumed daily by cynomolgus monkey (with DAT0115 dosing on day 1)

| Dose | Day-2 | Day-1 | Day 1 | Day 2 | Day 3 | Day 4 | Day 5 | Day 6 | Day 7 |
|---|---|---|---|---|---|---|---|---|---|
| 0.1 mg/Kg (iv) | 12 | 12 | 6 | 3 | 9 | 12 | 12 | 12 | 12 |
| 0.1 mg/Kg (iv) | 12 | 12 | 0 | 1 | 0 | 4 | 6 | 10 | 11 |
| 0.1 mg/Kg (iv) | 12 | 12 | 0 | 0 | 0 | 0 | 1 | 6 | 6 |
| 0.1 mg/Kg (sc) | 12 | 12 | 5 | 0 | 4 | 11 | 7 | 11 | 12 |
| 0.1 mg/Kg (sc) | 12 | 12 | 12 | 0 | 2 | 12 | 12 | 12 | 12 |
| 0.1 mg/Kg (sc) | 12 | 12 | 11 | 12 | 11 | 12 | 8 | 12 | 12 |

Example 12

DAT0115 exendin-4 AlbudAb Fusion Binds Rat, Cynomologus Monkey and Human Serum Albumin using Surface Plasmon Resonance DAT0115 was expressed and purified and then analysed by surface plasmon resonance (Biacore, GE Healthcare) to obtain information on affinity. The analysis was performed using a streptavidin chip (SA) coated with biotinylated serum albumin. 200-1000 resonance units (RUs) of each serum albumin was immobilised on the chip. Flow cell 1 was uncoated, flow cell 2 was coated with HSA, flow cell 3 was coated with RSA and flow cell 4 was coated with CSA. A range of concentrations of fusion was prepared (in the range 15.6 nM to 2 µM by dilution into BIACORE HBS-EP buffer (0.01M HEPES, pH7.4, 0.15M NaCl, 3 mM EDTA, 0.005% surfactant P20) and flowed across the BIACORE chip.

Affinity (KD) was calculated from the BIACORE traces by fitting on-rate and off-rate curves to traces generated by concentrations of dAb in the region of the KD. Affinities (KD) are summarised in the following table:

TABLE 10

| Affinity (KD) of DAT0115 | |
|---|---|
| Serum albumin types | DAT0115 |
| HSA | 600 nM |
| RSA | 2 uM |
| CSA | 2 uM |

Example 13

Characterisation of DAT0115 Thermal Denaturation by Differential Scanning Calorimetry (DSC)

The aim of this experiment was to monitor the thermal denaturation of DAT0115 by DSC (Differential Scanning calorimetry) using a capillary cell microcalorimeter VP-DSC (Microcal) equipped with an autosampler. Protein was dialysed overnight into 20 mM citrate pH6.2, 100 mM NaCl, filtered and then prepared at concentration of 1 mg/ml as determined by absorbance at 280 nm. Filtered dialysis buffer was used as a reference for all samples. DSC was performed at a heating rate of 180° C./hour. Before each sample a solution of 1% decon, and then buffer were injected to clean the cells and to provide instrumental baseline. Obtained traces were analysed using Origin 7 Microcal software. The DSC trace obtained from the reference buffer was subtracted from the sample trace. Precise molar concentration of the sample was used for calculations (performed automatically by Origin). Baseline setting for both upper and lower baselines linear regions before/after transition were selected and connected using cubic connect function. The resulting graph is fitted to non-2-state model, generating apparent Tm, and ΔHΔHv values.

The trace from DAT0115 was fitted to a non-two state transition model, with appTm of 56.3° C. Goodness of fit was satisfactory (see FIG. 4). The control trace, lysozyme, run using the same equipment produced good quality data as expected with perfect fit. (AppTm obtained for lysozyme was 76.2° C. which is in agreement with that reported in the literature (see FIG. 5).) Therefore, it was concluded that this experiment had provided reliable data indicating that DAT0115 is a molecule with a melting temperature of 56.3° C. which is acceptable for a clinical candidate.

Example 14

Characterisation of DAT0115, DAT0117 and DAT0120 in Solution State by SEC MALLS

The aim of this experiment was to determine the in solution state of DAT0115, DAT0117 and DAT0120 by SEC MALLS. Samples were purified and dialysed into appropriate buffer (PBS) and filtered after dialysis, concentration was determined and adjusted to 1 mg/ml. BSA and HSA were purchased from Sigma and used without further purification.

Details of Instrumentation:

Shimadzu LC-20AD Prominence HPLC system with an autosampler (SIL-20A) and SPD-20A Prominence UV/Vis detector was connected to Wyatt Mini Dawn Treos (MALLS, multi-angle laser light scattering detector) and Wyatt Optilab rEX DRI (differential refractive index) detector. The detectors were connected in the following order—LS-UV-RI. Both RI and LS instruments operated at a wavelength of 488 nm. TSK2000 (Tosoh corporation) or BioSep2000 (Phenomenex) columns were used (both are silica-based HPLC columns with similar separation range, 1-300 kDa) with mobile phase of 50 or 200 mM phosphate buffer (with or without salt), pH7.4 or 1×PBS. The flow rate used is 0.5 or 1 ml/min, the time of the run was adjusted to reflect different flow rates (45 or 23 mM) and is not expected to have significant impact onto separation of the molecules. Proteins were prepared in PBS to a concentration of 1 mg/ml and injection volume was 100u1. The light-scattering detector was calibrated with toluene according to manufacturer's instructions. The UV detector output and RI detector output were connected to the light scattering instrument so that the signals from all three detectors could be simultaneously collected with the Wyatt ASTRA software. Several injections of BSA in a mobile phase of PBS (0.5 or 1 ml/min) are run over a Tosoh TSK2000 column with UV, LS and RI signals collected by the Wyatt software. The traces are then analysed using ASTRA software, and the signals are normalised aligned and corrected for band broadening following manufacturer's instructions. Calibration constants are then averaged and input into the template which is used for future sample runs.

Absolute Molar Mass Calculations:

100 ul of 1 mg/ml sample was injected onto appropriate pre-equilibrated column After SEC column the sample passes through 3 on-line detectors—UV, MALLS (multi-angle laser light scattering) and DRI (differential refractive index) allowing absolute molar mass determination. The dilution that takes place on the column is about 10 fold, so the concentration at which in-solution state is determined is 100 ug/ml, or about 8 uM dAb.

The basis of the calculations in ASTRA as well as of the Zimm plot technique, which is often implemented in a batch sample mode is the equation from Zimm [*J. Chem. Phys.* 16, 1093-1099 (1948)]:

$$\frac{R_q}{K^*c} = MP(\theta) - 2A_2cM^2P^2(\theta) \qquad \text{(Eq. 1)}$$

where c is the mass concentration of the solute molecules in the solvent (g/mL)

M is the weight average molar mass (g/mol)

$A_2$ is the second virial coefficient (mol mL/g$^2$)

$K^* = 4p^2 n_0^2 (dn/dc)^2 l_0^{-4} N_A^{-1}$ is an optical constant where $n_0$ is the refractive index of the solvent at the incident radiation (vacuum) wavelength, $l_0$ is the incident radiation (vacuum) wavelength, expressed in nanometers, $N_A$ is Avogadro's number, equal to $6.022 \times 10^{23}$ mol$^{-1}$, and do/dc is the differential refractive index increment of the solvent-solute solution with respect to a change in solute concentration, expressed in mL/g (this factor must be measured independently using a dRI detector).

P(q) is the theoretically-derived form factor, approximately equal to $1 - 2\mu^2 \langle\ ^2\rangle /! + \ldots$, where $\mu = (4\pi/\lambda)\sin(\theta/2)$, and $\langle r^2 \rangle$ is the mean square radius. P(q) is a function of the molecules' z-average size, shape, and structure.

$R_q$ is the excess Rayleigh ratio (cm$^{-1}$)

This equation assumes vertically polarized incident light and is valid to order $c^2$.

To perform calculations with the Zimm fit method, which is a fit to $R_q/K^*c$ vs. $\sin^2(q/2)$, we need to expand the reciprocal of Eq. 1 first order in c:

To perform calculations with the Zimm fit method, which is a fit to

Rq/K*c vs. sin 2(q/2), we need to expand the reciprocal of Eq. 1 to first order in c:

$$\frac{K^*c}{R_q} = \frac{1}{MP(\theta)} + 2A_2c \qquad \text{Eq. 2}$$

The appropriate results in this case are $$M = \left(\frac{K^*c}{R_0} - 2A_2c\right)^{-1} \qquad \text{Eq. 3}$$

and $$\langle r^2 \rangle = \frac{3m_0\lambda^2 M}{16\pi^2} \qquad \text{Eq. 4}$$

where $m_0 \equiv d[K^*c/R_q]/d[\sin^2(\theta/2)]_{q\to 0}$ Eq. 5

The calculations were performed automatically by ASTRA software, resulting in a plot with molar mass determined for each of the slices [Astra manual].

Molar mass obtained from the plot for each of the peaks observed on chromatogram is compared with expected molecular mass of a single unit of the protein. This allows us to draw conclusions about in-solution state of the protein.

Experimental Data:

DAT0115

100 μl of 1 mg/ml DAT0115 was injected onto Superdex 200 column, equilibrated into 20 mM citrate, 0.1M NaCl, pH6.2. Flow speed was set at 0.5 ml/min. The protein eluted in a single peak, with Mw determined across the whole width of the peak as 17.4 kDa (expected Mw for a monomer is 16.9 kDa). Elution efficiency is 100%. See FIG. 6. (HSA control behaved as expected validating the experimental results for DAT0115. It elutes in two peaks with Mw 64 kDa (monomer) and 110 kDa (dimer). MW of the HSA dimer may not be very precise due to very small amount of protein within this peak.)

DAT0117

100 μl of 1 mg/ml DAT0117 was injected onto TSK2000 column, equilibrated into 50 mM phosphate buffer, pH7.4. Flow speed was set at 1 ml/min. About 50% of the injected amount of DAT0117 eluted off the column in two overlapping peaks with Mw around 35-45 kDa (dimer and above), which indicates strong self-association at the conditions tested here. (BSA control behaved as expected validating the DAT0117 experimental results, giving two peaks with molar mass of 61 kDa and 146 kDa (monomer and dimer). See FIG. 7 for SEC Mal results.

DAT0120

100 μl of 1 mg/ml DAT0117 was injected onto TSK2000 column, equilibrated into 50 mM phosphate buffer, pH7.4. Flow speed was set at 1 ml/min. About 50% of the injected amount of DAT0120 eluted off the GF column in slightly asymmetric peak with Mw determined at around 25 kDa. This indicates self-association of DAT0120 at the conditions tested here, the protein appears to be in a rapid monomer-dimer equilibrium. (BSA control behaved as expected validating the DAT0120 experimental results, giving two peaks with molar mass of 61 kDa and 146 kDa (monomer and dimer)). See FIG. 8 for SEC Mal results.

It was concluded from these experiments above that DAT0115 demonstrates significantly less (and possibly no) self association under the conditions used here compared to the other two molecules which show significant elf association. In-solution monomeric state may be preferable with regards to in vivo action and upstream and downstream process during manufacturing so DAT0115 may be the most ideal molecule for clinical progression with regards in-solution state.

Example 15

Purification from Mammalian Expression without using the Affinity Matrix Protein L Both DAT0120 and DAT0115 were purified from HEK 293 supernatants. Each protein was expressed in mammalian tissue culture in HEK 293E cells from the pTT-5 vector. A 1 ml column of MEP Hypercel resin was equilibrated with PBS, washed with 0.1M Sodium Hydroxide and then re-equilibrated with PBS. 200 ml of supernatant was applied to the column at 2.5 ml/min and then the column was washed with PBS and eluted with 0.1M Glycine, pH2.

Post elution the sample was neutralised by addition of ⅕$^{th}$ volume of 1M Tris, pH 8 and stored at room temperature. The sample showed light precipitation after storage and was filtered using a steriflip device prior to desalting.

Two 26/10 HiPrep desalting columns were equilibrated with 20 mM Sodium Acetate, pH5 (measured pH 5.3) at 10 ml/min, cleaned by addition of 0.1M NaOH and re-equilibrated into 20 mM Sodium Acetate, pH5.

DAT0115 was desalted into 20 mM Sodium Acetate, pH5 prior to loading on 1 ml HiTrap SPFF equilibrated in 20 mM Sodium Acetate, pH5 (actual 5.2). Post washing of the column it was subjected to a 0-100% gradient with 20 mM Sodium Acetate, pH5, 1M NaCl and elution fractions with absorbance over 5 mAus were collected and analysed by SDS-PAGE.

Post storage of the SP FF fractions overnight the sample was 0.2 um filtered and applied to 2×26/10 HiPrep desalting columns equilibrated into 20 mM Sodium Citrate, pH6.2, 100 mM NaCl. The elution was concentrated in a 20 ml centrifugal concentrator, filter sterilised and endotoxin tested at dilutions 1/10 and 1/200.

Endotoxin was tested at two dilutions, the 1/10 dilution gave a value of 30Eu/ml with a spike recovery of 250. The 1/200 test gave a value of <10.8Eu/ml with a spike recovery of 126%. The sample was submitted for MS analysis using the ID 27823. There are low level contaminants visible below the 80 kDa marker and between the 110-160 kDa markers in the high loading. The sample looks to be greater than 95% pure.

Example 16

Expression and Purification of Genetic Fusions of Exendin-4 and DOM7h-14-10/DOM7h-11-15 AlbudAb The aim of this experiment was to efficiently express DMS7139 and DMS7143.

DMS7139 is a fusion of exendin-4 with DOM7h-14-10 (a domain antibody (dAb) that binds serum albumin, also known as AlbudAb TM) and DMS7143 is a fusion of exendin-4 with DOM 7h-11-15 (a domain antibody (dAb) that binds serum albumin, also known as an AlbudAb) in E. coli with correctly processed N-termini. The fusion could then be tested for activity of the exendin-4 portion and of the AlbudAb portion in subsequent experiments.

Exendin-4 was cloned as a fusion with DOM7h-14-10 or DOM7h-11-15, where exendin-4 peptide was at the 5' end of the construct and AlbudAb at the 3' end. In total two constructs were made each including (Gly4Ser)3 linker between the exendin-4 peptide and the AlbudAb. The linker was included as a spacer to separate the exendin 4 spatially from the dAb to prevent steric hindrance of the binding between the exendin-4 and the GLP-1 receptor. The sequences of the constructs are shown in FIGS. 1(m) and 1(n). To enable cloning into expression vector, fusions were produced as assembly PCRs with NdeI restriction site on 5' followed by modified OmpT (OmpT AWA the amino acid sequence is shown in FIG. 1(q), SEQ ID NO 28) signal peptide and with BamHI site on 3' terminus OmpT AWA signal peptide has the last three codons changed from the wildtype to "GCTTGGGCC" (shown in FIG. 2 (p): SEQ ID NO 33) which codes AWA instead of SFA. That change improves processing at the correct site by the signal peptidase of E. coli.

Additionally the sequence of the fusion starts straight after the peptidase cleavage site. An NcoI digestion site has been introduced, which overlaps with the last codon of the signal peptide and two first amino acids of exendin-4 sequence. This change facilitates future subcloning as well as leading to production of the fusion with free N-terminal end of exendin-4. The modified pET12a expression vector (pET vectors obtained from EMD Biosciences) comprising the changes listed above was given the name pDOM35. Vector and assembly PCRs were digested with NdeI and BamHI restriction endonucleases followed by ligation of the insert into the vector using a Quick Ligation Kit (NEB). 2 microliters of this ligation was used for transformation of MachI cells. After the recovery growth period, cells were plated on agar plates containing carbenicilin and incubated at 37° C. overnight. Colonies were sequenced and those containing the correct sequence were used for plasmid propagation and isolation (Plasmid Mini Prep kit, Qiagen). BL21(DE3) cells were transformed with plasmid DNA and resulting colonies were used for inoculation of expression culture. Expression was performed by inoculation of a 4×0.5 liter culture of TB Onex media (supplemented with Overnight Express™ autoinduction solutions), 1 droplet of antifoam and 100 microgram per milliliter of carbenicillin. Culture was incubated for 3 nights at 30° C. with agitation 250 rpm, and then the culture supernatant was clarified by centrifugation at 3700×g for 1 hour. The expressed protein was then purified from the clarified supernatant using protein L streamline (GE Healthcare, Cat. No. 28-4058-03, protein L coupled), and eluted from the Protein L using 0.1M glycine pH2.0, then neutralized using 0.1 volume of 1M Tris pH8.0. Next protein was concentrated and dialysed to Buffer A (20 mM sodium acetate-acetic acid pH 5.0) and purified by Ion Exchange Chromatography on the AktaXpress (GE healthcare). Protein was loaded on Resource S 6 ml column in Buffer A (no salt buffer) and then eluted with Buffer B gradient (20 mM sodium acetate-acetic acid pH 5.0 1M NaCl) from 0-68% B in 65 minutes in fractions (for DMS7139). Fractions were analyzed on SDS-PAGE and by Mass Spectrometry and those of the correct mass were pooled. The final protein was dialyzed into 20 mM citrate 0.1M NaCl buffer, and identity was reconfirmed by SDS-PAGE and Mass Spectrometry.

Example 17

Exendin-4 AlbudAb Fusions DMS7139 and DMS7143 Bind Serum Albumin using Surface Plasmon Resonance DMS7139 and DMS7143 were expressed and purified as described above and analysed by surface plasmon resonance (Biacore, GE Healthcare) to obtain information on affinity. The analysis was performed using two CM5 chips (carboxymethylated dextran matrix) that were coated with serum albumin. ~500 resonance units (RUs) of each serum albumin was immobilised in acetate buffer pH 4.5. The first chip had flow cell 1 uncoated and blocked and flow cell 2 was coated with MSA (560Rus). The second chip had flow cell 1 uncoated and blocked, flow cell 2 was coated with HSA, flow cell 3 was coated with CSA and flow cell 4 was coated with RSA. For all serum albumins, the aim was to coat in the region of 350 RUs of protein onto the chip.

A range of concentrations of fusion was prepared (in the range 55 nM to 1 µM for DMS7139 and 24 nM to 4.4M for DMS7143) by dilution into BIACORE HBS-EP buffer (0.01M HEPES, pH7.4, 0.15M NaCl, 3 mM EDTA, 0.005% surfactant P20) and flowed across the BIACORE chip. Affinity (KD) was calculated from the BIACORE traces by fitting on-rate and off-rate curves to traces generated by concentrations of dAb in the region of the KD. Affinities (KD) are summarised in the following table 11:

TABLE 11

|     | DMS7139 (M) | DMS7143 (M) |
| --- | --- | --- |
| HSA | 2.69E−08 | 1.48E−08 |
| RSA | 3.15E−08 | 2.19E−07 |
| CSA | 4.23E−08 | 3.89E−08 |
| MSA | 7.37E−08 | 8.93E−08 |

It was concluded that DMS7139 and DMS7143 have affinity for serum albumin that (with the exception of DMS7143 affinity for RSA) is in the range 10-90 nM. This is significantly higher than the affinity for SA of previous fusions (for example DAT0115 which is the exendin-4 linked to the DOM7h-14 AlbudAb with a glycine serine linker which has affinities to these serum albumins in the 100s of nM range). The higher affinity of the new fusions (to serum albumin) is likely to translate to longer plasma half lives in vivo which will mean that the fusions will be able to be administered less often for the same efficacy and/or maintain a more constant level of drug in the plasma over time potentially reducing unwanted cMax related toxicity or side effects.

Example 18

DMS7139 and DMS7143 Fusions are Active in GLP-1 Receptor Binding Assay

GLP-1R is a 7TM G-protein coupled receptor which for the purposes of this assay is expressed on CHO cells. Activation of the receptor by GLP-1 or analogues leads to the conversion of ATP to cAMP by adenylate cyclase which is coupled to the receptor. The CHO cells are stably transfected with the 6CRE/luc reporter gene. Therefore, on production of cAMP following GLP-1 activation of the receptor, the promoter gene (containing 6 copies of cAMP response element—6CRE) drives the expression of the luciferase reporter gene. This then catalyses a reaction with luciferin to produce light which can be measured on a luminometer.

Method

CHO 6CRE GLP1R cells were rapidly defrosted by half immersing the vial(s) in a 37° C. water bath, and the contents of the vial(s) transferred to a 50 ml falcon tube and 10 ml RPMI (phenol red free) assay media (Sigma, cat #R7509)+2 mM L-glutamine (Gibco, cat #25030)+15 mM HEPES (Sigma, cat #H0887) added per vial. After counting and centrifugation at 1200 rpm for 5 minutes cells were resuspended in the appropriate volume of RPMI assay media to give $1\times10^6$ cells per ml and 50 µl dispensed into each well of a white 96 well flat bottom tissue culture plate (Costar 96 well tissue culture plate, white sterile, cat #3917). Cells were incubated overnight at 37C/5% CO2. Next day cell were removed from incubator and 5 µl of previously prepared control/sample was added to wells and plate was returned to incubator for 3 hours 37° C. and 5% CO2.

Preparing Exendin-4 Control (Sigma, cat #E7144)

In a V-bottom 96 well plate add 2 µl of 1 mg/ml) Exendin-4 to 198 µl RPMI assay media to give a 2.39 µM solution. Add 41 of the 2.39 µM solution to 237 µl RPMI assay media to give a 20 nM solution (for a final concentration in the assay of 10 nM). Serial dilute the control 1:10 down the plate (15 µl control+135 µl RPMI assay media) to generate an 8 point curve.

Preparing Unknown Samples

Use the same guidelines for preparation of the control for the preparation of the unknown samples. Make the top concentration at twice the final assay concentration required and dilute 1:10 down the plate.

Preparing the Luciferase (Promega, cat #E2620)

Remove the required number of Bright-Glo luciferase aliquots from the freezer and allow defrosting at RT in the dark. One 5 ml vial is sufficient for one assay plate After the incubation time 5 µl of Bright-Glo Luciferase reagent was added to all wells and the plate was incubated at room temperature for 3 mins to allow cell lysis to occur. The luminescence (counts per second) was read using the M5e microplate reader, reading each well for 0.1 sec. CPS of the background wells containing cells only, was subtracted from all other wells. The control wells (GLP-1(7-36) or Exendin-4) should exhibit maximum stimulation at the highest concentrations. Concentration effect curves of the unknown samples are fitted from which the EC50 is calculated with use of GraphPad Prism or ExcelFit software.

The two exendin-4 AlbudAb fusions (DMS7139 and DMS7143) were tested in the assay for activity in the GLP-1R BA side-by-side with exendin-4. The results are in the table 12 below:

TABLE 12

|     | GLP-1R BA $EC_{50}$ (pM) | GLP-1R BA (10 uM albumin) $EC_{50}$ (pM) |
| --- | --- | --- |
| DMS7139 | 265.1 | 1488 |
| DMS7143 | 186.8 | 871.1 |
| Exendin 4 | 72.18 | Not done |
| DAT0115 control | 211.8 | 607.6 |

It was concluded from the above results that DMS7139 and DMS7143 display the expected activity in the GLP-1R BA and therefore it is likely that they will be active against the GLP-1 receptor in vivo. Therefore DMS7139 and DMS7143 are good candidates for further preclinical investigation with a view to moving into the clinic if this is successful.

Example 19

The vector expressing DAT0115 or DAT0117 was transformed into the *E. coli* strain B121-(DE3) (Novagen). A 250 ml flask containing 50 ml of modified terrific broth media (Sigma cat-no. T0918) was inoculated at an OD=0.1 and was then grown at 30° C. supplemented with 50 mg/l kanamycin. At $A_{600}$=0.5-1 cells were induced with IPTG to 50 µM final concentration, and growth was continued at the same temperature over night. The culture was spun down and DAT0115 or DAT0117 was captured out of the culture supernatant using the ProteinL resin (made in house). Batch binding occurred over night at 8° C., the resin was washed with 10 column volumes of PBS and DAT0115 or DAT0117 was eluted from the resin with three column volumes of 0.1 M glycine pH=2. The protein was neutralized by adding ⅕ of the volume of 1M Tris pH8.0. The protein was then analyzed by SDS-gel and mass spectrometry (MS) or by Edman degradation (Edman).

The vectors expressing DAT0117 that are marked with an asterisk (*) were transformed, cultured and analysed, using the conditions as set out in Example 16.

TABLE 13

| Leader name | Construct | % full length MS (Edman) | % minus two amino acids MS (Edman) |
|---|---|---|---|
| OmpA | DAT0115 | 77% | 23% |
| OmpA-AMA | DAT0115 | 100% | 0% |
| OmpA-AWA | DAT0115 | 84% | 16% |
| OmpT | DAT0117 * | 46% (42%) | 54% (58%) |
|  | DAT0117 | 41% | 59% |
| OmpT-AMA | DAT0117* | 86% (83%) | 14% (17%) |
| OmpT-AWA | DAT0117* | 100% (100%) | 0% (0%) |
| GAS | DAT0117 | 13% | 87% |
| GAS-AMA | DAT0115 | 72% | 28% |

Example 20

Expression and Purification of DMS7139 (a Genetic Fusions of Exendin-4 and DOM7h14-10) AlbudAb using the MalE/pET30 Vector The DMS7139 gene was amplified by PCR from a plasmid containing DMS7139 using the oligonucleotide no. 1 (FIG. 2 s: SEQ ID NO 47) (GGAATTCCATATGAAAAT-CAAAACCGGTGCTCGCATCCTGGCTCTGTCCGC TCTGACCACTATGATGTTCTCCGCTTC-CGCGCTGGCTCATGGTGAAGGAACA TTTACCAGT-GAC) and oligonucleotide no. 2 GTTCAGAATTCTTAT-TACCGTTTGATTTCCACCTTGGTCCCTTG (FIG. 2 t: SEQ ID NO 48). The amplification product contains the DMS7139 construct with an N-terminal MalE signal sequence MKIKTGARILALSALTTMMFSASALA (FIG. 9 j: SEQ ID NO 49) and leaves at its 5' and 3' ends the recognition sequence for NdeI and EcoRI, respectively. The resulting gene fragments were digested with NdeI/EcoRI, and were ligated into the NdeI/EcoRI digested pET30 vector (Invitrogen). To verify the insert the clones were sequenced using the T7-forward and T7-reverse primers.

The vector expressing the DMS7139 was transformed into the E. coli strain BL21-(DE3) (Novagen) containing the pECO-pg1 vector (see Aon et al. applied and environmental microbiology feb. 2008 vol. 74, No. 2, pg 950-958 and cultures were grown at 30° C. in minimal media (see Korz D. J. et al J. Biotechnol. 1995 39 pg 59-65.) supplemented with 50 mg/l of kanamycin and 37.5 mg/L chloramphenicol. At $A_{600}$ between 0.25 and 0.5, cells (actual value obtained 0.347) were induced with IPTG to 70 µM final concentration, and growth was continued at 28° C. over night. The culture was spun down and DMS7139 was captured out of the culture supernatant using the ProteinL resin (made in house). Batch binding occurred over night at 4° C., the resin was washed with 10 column volumes of PBS and DMS7139 was eluted from the resin with three column volumes of 0.1 M glycine pH=2. The protein was then analyzed by SDS-gel and mass spectrometry. As shown in the FIG. 10 mass spectrometry shows that there is very pure DMS7139.

The sequence of the DNA encoding the protein DMS7139 can also be codon optimized for E. coli expression and this sequence is shown in FIG. 2(u) SEQ ID NO 50.

Example 21

DMS7139 Binds to the Mouse, Rat, Cynomolgus Monkey and Human GLP-1R with Similar Potency In order to determine the relative potency of DMS7139 at the human, mouse, rat, and cynomolgus monkey GLP-1R, a melanophore functional GLP-1R bioassay was used (similar to Jayawickreme et. al., Curr Protocols in Pharmacol. 2005). Melanosome translocation via 7™ activation has been well documented, and G proteins resident within the melanophore cells have been shown to couple to GPCRs in a manner similar to mammalian cell systems (Gross et al., J Cell Biol 2002; 156:855-865). This bioassay uses a melanophore cell line, derived from skin cells of the frog Xenopus laevis, which possess dark pigment (melanin) containing organelles known as melanosomes (Lerner, Trends Neurosci. 1994; 17:142-146). Changes in intracellular cAMP level control the extent to which melanosomes are aggregated or dispersed throughout the cell, and thus the melanophore cell colour density is directly related to cAMP levels. Further details are given in below.

Full length open reading frame cDNAs encoding rat, mouse and human GLP-1 receptors were cloned into the expression vector pJG3.6 or pcDNA3 using standard molecular biology techniques. Genebank accession numbers are shown below in Table 14.

TABLE 14

| Genebank accession numbers | |
|---|---|
| GLP1R | Genebank |
| rat | NM_012728 |
| mouse | NM_021332 |
| human | NM_002062 |

The clone encoding the cynomolgus monkey GLP-1R was amplified from cDNA reverse transcribed from total RNA isolated from cynomolgus monkey lung, liver and brain and subcloned into pcDNA3.2DGW. Full length cDNA sequence was confirmed. Melanophores were maintained in T225 flasks (Costar Cat. No. 3000) in L-15 media at 27° C. and 0% $CO_2$ and split once a week (1:10) from a confluent flask with 0.7× trypsin followed by twice weekly feeding. The cDNA for cynomolgus monkey is shown in FIG. 2 (r) (SEQ ID NO 45).

For assaying purposes cells were washed, trypsinized and resuspended in 0.7×EPG PBS at a concentration of 15×10⁶ cells per ml. 800 µl of cells were gently mixed with 20-40 µg of cDNA and incubated on ice for 20 minutes. Following incubation, 800 µl of cells/cDNA mix were pipetted into a cuvette and electroporated at 500V, 725 uF and 950 ohms Cells were then transferred from the cuvette directly into a T75 flask containing RFM (regular frog media) and incubated at room temperature for at least 3 hours and then overnight in an incubator (25° C., 0% CO2). The next day, cells were trypsinized, counted and added to Costar 96 half well plates (Cat. #3697) at a density of 300,000 cells per ml. After 2 hours they were placed in a sealed container in the incubator overnight (25° C., 0% CO2). The following day media was aspirated and 25 μl MAB (Melanophore Assay Buffer) containing 1% DMSO and 10 nM melatonin was added to each well. Cells were incubated for one hour and basal transmittance was measured on a SLT Spectra plate reader at 620 nm. Next, a dilution series (12 point series using 3 fold dilution intervals in MAB) containing 25 μl of a 2× concentration peptides and standards were added directly to each well. Standards included melatonin 10 nM, MSH 200 nM and MAB and were used to establish assay system Minimum, Maximum, and basal response levels, respectively. Following addition of peptides and standards, plates were incubated for 1 hour and transmittance measured as before. Data was analyzed using Robosage (version 7.3.2) by calculating (1−Tf/Ti) where Ti is initial baseline read, and Tf is the response read.

$G_s$-coupled 7TM receptor activation (i.e. GLP-1R) leads to an increase in intracellular cAMP, causing melanosomes which have previously been aggregated using melatonin to become more dispersed, a response that is measured as a decrease in light transmittance through the cell. Alternatively, under conditions of decreasing cAMP, the melanosomes aggregate leading to an increase in light transmittance through the cell. Therefore, following transfection and transient expression of a GLP-1R cDNA containing plasmid construct into melanophores, the relative potency of DMS7139 for GLP-1R activation can be calculated from a dose-response curve. Results are shown below in Table 15.

TABLE 15

DMS7139 potency in the melanophore assay

| Clone Name | Cynomolgus GLP-1R pEC50 | Rat GLP-1R pEC50 | Mouse GLP-1R pEC50 | Human GLP-1R pEC50 |
|---|---|---|---|---|
| DMS7139 | 10.62 | 10.78 | 9.97 | 10.63 |
| DMS7139 | 10.63 | 11.11 | 10.50 | 11.39 |
| DMS7139 | | 10.79 | | |
| DMS7139 | | 11.07 | | |
| GLP-1 (7-36) | 11.03 | 11.16 | 11.17 | 11.43 |
| GLP-1 (7-36) | | 11.09 | 11.47 | 11.40 |
| GLP-1 (7-36) | | 10.97 | | |

DMS7139 was tested for potency in the assay using melanophores transfected with human, mouse, rat and cynomolgus monkey GLP-1R in at least duplicate for each of the species. The pEC50s for the duplicate assays are listed in Table 15. The potencies at the cynomolgus monkey, human and rat receptors are very similar with possibly slightly lower potency at the mouse receptor. Overall this data shown in Table 15 gives good confidence that the efficacy seen in mouse models with this drug is likely to be replicated in possible toxicology species (rat and cynomolgus monkey) and also in human.

Example 22

Efficacy and Duration of Action of DAT0115 and DMS7139 in the db/db Mouse Model of Type II Diabetes The aim of this study was to determine and compare the duration of action of DAT0115 and DMS7139 on oral glucose tolerance in 10-11 week old db/db mice (obtained from Jackson Labs). Animals were randomized across treatment groups by blood glucose levels assessed three days prior to the start of the experiment. This ensured similar mean starting glucose level in each of the study groups. DAT0115 and DMS7139 were administered subcutaneously at 1 mg/kg at 120 h, 96 h, 72 h, or 48 h prior to the oral glucose bolus (shown in FIG. 11A).

The glucose AUC was significantly lowered over the 2 hour time period of the oral-glucose tolerance test (OGTT) compared to vehicle treated db/db mice at all time points up to 120 h for DMS7139 and at all time points up to 96 h for DAT0115 (FIG. 11B). W*hilst* there was no statistical difference between DAT0115 and DMS7139 dosed at 72 h, 96 h or 120 h, DAT0115 lowered glucose AUC significantly more than DMS7139 at 48 h.

It was concluded that the more consistent lowering of glucose AUC exhibited by DMS7139 was representative of a more desirable profile for a drug in this class. Therefore, whilst this study did not identify clear superiority, DMS7139 was selected as the lead based on this and other data.

Example 23

Repeat dose of DMS7139 shows dose Dependent Lowering of HbA1c when Compared to the DOM7h-14 Control The aim of this study was to examine HbA1c lowering following repeat dosing of DMS7139 in 10-11 week old db/db mice (Jackson labs). HbA1c is a glycated form of haemoglobulin whose concentration is used as a surrogate measure of plasma glucose concentration over a prolonged time period. To ensure similar mean starting HbA1c level in each of the study groups, db/db mice were randomized based on HbA1c levels three days prior to the start of the experiment. Animals were dosed with either DMS7139 (0.01, 0.03, 0.1, 0.3 mg/kg), Byetta™ (0.0001, 0.001, 0.01, 0.1 mg/kg) or DOM7h-14 (0.3 mg/kg) subcutaneously QD for 2 weeks. Measurements of body weight, food intake and glucose were taken during the study with HbA1c measurements taken at the end of the 14 days.

Fed glucose and HbA1c were significantly lowered in the DMS7139 treatment group at 0.03, 0.1 and 0.3 mg/kg versus control (DOM7h-14) although they were not significant against saline control (see results in FIG. 12). The data obtained for the saline control was lower than expected based on data obtained with the lowest dose of exendin-4 or DMS7139. There were no changes observed with exendin-4 compared to saline control. There were also significant decreases in body weight and food intake with DMS7139. Exendin-4 did show significant effects on food intake at the highest dose.

It was concluded that repeat dosing with DMS7139 leads to HbA1c lowering in db/db mice as well as effects on food intake and body weight. These changes are consistent with those expected for a GLP-1R agonist.

Example 24

DAT0115 and DMS7139 Showed Dose Dependant Reduction in Food Consumption and Body Weight Compared to DOM7h-14 control in the Diet Induced Obese (DIO) Mouse Model of Obesity The aim of the study described here was to determine whether food consumption and, as a result, body weight over a 10 day period is affected by treatment with DAT0115 and DMS7139 and to determine whether one of these compounds had a longer duration of action than the other. This may be predictive for humans. An experiment was conducted in the diet induced obese (DIO) mouse feeding model with DAT0115, Byetta and DMS7139 dose groups.

Male C57B1/6 mice (Taconic) were fattened on 60% kcal high fat irradiated diet (Research Diets D12492) for 12 weeks and then transferred to the in-house facility. Upon arrival, the mice were individually housed on alpha-dri bedding in a temperature and humidity controlled room (70-72° F., Humidity=48-50%, 5 AM/5 PM light cycle). The diet was changed to 45% high fat diet (Research Diets D12451) and the animals acclimated for 18 days. Prior to administration of compound, mice were injected subcutaneously with saline for three days and food consumption monitored. Mice were grouped such that body weight and food consumption were not different between groups. Three groups each were dosed with either DAT0115 or DMS7139 at 0.01 mg/kg, 0.1 mg/kg and 1 mg/kg, one group with a negative control molecule (DOM7h-14 AlbudAb™ at 1 mg/kg) and one with exendin-4 positive control (0.01 mg/kg). Daily food consumption and body weight was determined for 10 days. DAT0115 and DMS7139 showed dose dependent reduction in food consumption and body weight compared to the DOM7h-14 control (see results in FIG. 13). Note the exendin referred to in FIG. 13 was Byetta™. The data from this mouse study indicates that there is no statistical difference between the efficacy of these.

Example 25

PK Analysis of DMS7139 in Mouse, Rat and Cynomolgus Monkey

A suite of studies was conducted s.c. and i.v in three model species (db/db mouse, rat and cynomolgus monkey) with DSM7139. Doses were selected with the aim of achieving plasma concentrations predicted to be detectable by the assays at relevant time points: 1 mg/kg i.v. and s.c. in mouse, 1 mg/kg s.c. and 0.3 mg/kg i.v. in rat, 0.1 mg/kg i.v. and s.c. in cynomolgus monkey.

Time points for PK sampling were: db/db mouse (0.17, 1, 4, 8, 24, 48, 72, 96, 120 and 168 hours), rat (0.17, 1, 4, 8, 12, 24, 48, 72, 96 and 120 hours) and cynomolgus monkey (0.083 (i.v. group only), 0.5, 4, 8, 24, 48, 96, 144, 192, 288, 336, 504 and 672 hours (4 weeks)). Serial sampling of blood was performed, except in mouse, where one animal was sacrificed per data point. Plasma samples were prepared and stored frozen for later analysis of DMS7139 levels.

Two quantification assays were used for analysing PK samples in various studies: an ELISA method that detects the exendin-4 and AlbudAb parts of the molecules and an HPLC-MS/MS method that detects an N-terminal peptide from exendin-4. Data from the ELISA based method is shown here.

ELISA

Levels of DAT0115 and DMS7139 in cynomolgus monkey plasma were determined using an ELISA assay. Briefly, 96-well fluoronunc plates (Nunc #437796) were coated overnight in the fridge with anti-exendin-4 antibody (Abcam cat #ab26263) at 5 µg/mL in 50 mM sodium carbonate buffer pH 9.4 (100 µL per well). The following day, plates were washed 5 times with 10 mM Tris, 150 mM NaCl pH7.5 plus 0.1% tween-20 (300 µL per well) then blocked with 200 µl. of blocking buffer (superblock, thermoscientific #37535, in TBS) shaking for approximately 1 hour at nominally 37° C. Wells were washed as before then incubated whilst shaking with 100 µl per well of QCs, standards or samples for approximately 2 h at nominally 37° C. Again, wells were washed and then incubated with a 1:2000 final dilution of rabbit anti-human kappa light chain antibody in assay buffer (10 mM Tris, 150 mM NaCl, 0.1% BSA, 0.1% Tween 20 pH 7.5) with shaking for 1 h at nominally 37° C. followed by washing as before. Wells were then incubated with shaking with 100 µl per well of reporter tag solution (Goat anti-Rabbit IgG conjugate at 1/500,000 in assay buffer at nominally 37° C. and washed as before. Bound DAT0115 or GSK2374697A was detected by adding 100 µL per well of development substrate (upersignal ELISA femto (thermoscientific #37075) with constant shaking for approximately 1 minute and then read using a chemiluminescence plate reader (Wallac 1420 Victor Mulyilabel Counter (Perkin Elmer Life Sciences).

Compartmental and non-compartmental pharmacokinetic analyses were performed on the measured plasma levels using WinNonLin software version X TBC (see Table 16 below). For the non-compartmental results all pK data for DAT0115 and DMS7139 was compiled and fitted on the same day for consistency between studies. The data shown is therefore the compiled data, NCA results and figures for DAT0115 and DMS7139

In cynomolgus monkey, half life was calculated to be 106.4 h or 112.8 h (iv) and 113.8 h or 113.1 h (sc) calculated by compartmental and non-compartmental methods respectively. It was concluded that in all three species, DMS7139 has a plasma half-life approaching that of serum albumin itself and therefore given the similar affinity that DMS7139 has for human serum albumin (compared to cynomolgus serum albumin for example) this give good confidence that DMS7139 will have a half life in man that will be compatible with weekly (or less frequent) dosing.

TABLE 16

| Molecule | ROA | Dose (mg/kg) | Non-Compartmental Methods | | | | Compartmental Methods | |
|---|---|---|---|---|---|---|---|---|
| | | | AUC 0-inf (hr * ng/mL) | CL/CL_F (mL/hr/kg) | F (s.c.) (%) | T½ (hr) | CL/CL_F (mL/hr/kg) | T½ (hr) |
| A) db/db mouse data (ELISA data) | | | | | | | | |
| DMS7139 | IV | 1 | 815813 | 1.2 | n/a | 32.8 | 1.24 | 33.7 |
| | SC | 1 | 270107 | 3.7 | 33.1 | 24.9 | 3.66 | 26.2 |
| B) Rat data (ELISA data) | | | | | | | | |
| DMS7139 | IV | 0.1 | 225925 | 0.4 | n/a | 106 | 0.5 | 112.8 |
| | SC | 0.1 | 139657 | 0.7 | 61.8 | 114 | 0.7 | 113.1 |

TABLE 16-continued

| Molecule | ROA | Dose (mg/kg) | Non-Compartmental Methods | | | | Compartmental Methods | |
|---|---|---|---|---|---|---|---|---|
| | | | AUC 0-inf (hr * ng/mL) | CL/CL_F (mL/hr/kg) | F (s.c.) (%) | T½ (hr) | CL/CL_F (mL/hr/kg) | T½ (hr) |
| C) Cynomolgus monkey data (ELISA data) | | | | | | | | |
| DMS7139 | IV | 0.3 | 223069 | 1.3 | n/a | 25.4 | 1.4 | 47.2 |
| | SC | 1 | 151423 | 7.3 | 20.4 | 49.7 | 7 | 39.2 |

Example 26

Comparison of PK Analysis of DMS7139 and DAT0115 in Cynomolgus Monkey

In order to choose the most desirable molecule to develop for use in humans, the pharmacokinetic parameters in cynomolgus monkey were compared for DAT0115 and DMS7139 (see Table 17). We concluded that the data in the table showed that DMS7139 has more desirable PK parameters than DAT0115, demonstrating longer half-life in cynomolgus monkey when administered sub-cutaneously or intravenously. The longer half-life has the effect that at later time points, DMS7139 was consistently higher in concentration in plasma than DAT0115 (data not shown).

TABLE 17

Comparison of half-life of DAT0115 and DMS7139 in cynomologus monkey

| Molecule | ROA (method of analysis) | Dose (mg/kg) | Non-Compartmental Methods | | | | Compartmental Methods | |
|---|---|---|---|---|---|---|---|---|
| | | | AUC 0-inf (hr * ng/mL) | CL/ CL_F (mL/hr/kg) | F (s.c.) (%) | T½ (hr) | CL/ CL_F (mL/hr/kg) | Terminal T½ (hr) |
| DAT0115 | IV (LC/MS/MS) | 0.1 | 34507.5 | 3.3 | n/a | 67.3 | 4 | 80.7 |
| | SC (LC/MS/MS) | 0.1 | 34203.8 | 3.1 | 99.1 | 67.9 | 2.9 | 91.1 |
| DMS7139 | IV (LC/MS/MS) | 0.1 | 238360 | 0.4 | n/a | 110 | 0.4 | 117.6 |
| | IV (ELISA) | 0.1 | 225925 | 0.4 | n/a | 106 | 0.5 | 112.8 |
| | SC (LC/MS/MS) | 0.1 | 128093 | 0.8 | 53.7 | 97.7 | 0.8 | 82.1 |
| | SC (ELISA) | 0.1 | 139657 | 0.7 | 61.8 | 114 | 0.7 | 113.1 |

Example 27

Production of the PYY (3-36) DOM7h-14-10 (R108C) AlbudAb™ Peptide Conjugate DMS7605 (which has the Structure shown in FIG. 14) and which is: a DOM 7h-14-10 (R108C) AlbudAb Conjugated to the PYY3-36 via a Lysine and a 4 Repeat PEG Linker)

The DOM7h-14-10 (R108C) albudab was expressed and purified as described as follows in *E. coli*: The gene encoding the DOM7h-14-10 (R108C) was cloned into vector pET30. To enable cloning into expression vector, fusions were produced as assembly PCRs with NdeI restriction site on 5' followed by the PEL B leader sequence (amino acid sequence shown in FIG. 9 (*i*) SEQ ID NO 46). Vector and assembly PCRs were digested with NdeI and BamHI restriction endonucleases followed by ligation of the insert into the vector using a Quick Ligation Kit (NEB). 2 microliters of this ligation was used for transformation of MachI cells. After the recovery growth period, cells were plated on agar plates containing carbenicilin and incubated at 37° C. overnight. Colonies were sequenced and those containing the correct sequence were used for plasmid propagation and isolation (Plasmid Mini Prep kit, Qiagen). BL21(DE3) cells were transformed with plasmid DNA and resulting colonies were used for inoculation of expression culture. Expression was performed by inoculation of a 250 ml flask containing 50 ml of modified terrific broth media (Sigma) and this was inoculated at an OD=0.1 and was then grown at 30 degC supplemented with 50 mg/ml Kanamycin. At A600=0.5-1 cells were induced with IPTG to 50 uM final concentration, and growth was continued at 23 degC overnight. Then the culture supernatant was clarified by centrifugation at 3700×g for 1 hour. The expressed protein was then purified from the clarified supernatant using Protein L streamline (GE Healthcare, Cat. No. 28-4058-03, protein L coupled), and eluted from the Protein L using 0.1M glycine pH2.0, then neutralized by addition of ⅕$^{th}$ elution volume of 1M Tris, pH8.0. The protein was then pH adjusted using 0.1M Citric Acid to pH5 and applied to a 30 ml Source S column (GE Healthcare) equilibrated with 50 mM Sodium Citrate, pH5. A gradient from 0-100 of 50 mM Sodium Citrate, pH5, 1M NaCl was applied using the AktaXpress FPLC (GE healthcare) over 150 ml. Fractions were analyzed on SDS-PAGE and those containing the purest product were pooled. The final protein was desalted into 50 mM Sodium Phosphate, pH6.5, 5 mM EDTA.

The Dom7h-14-10 (R108C) AlbudAb was then linked to a PYY 3-36 amino acid molecule (but with a lysine at position 10 which can be derivatised with PEG linker) using the PEG linker shown in FIG. 14. The PYY and the PEG were prepared by standard chemical synthesis. The maleimide at the end of the PEG linker was then used to conjugate the PYY peptide to the free cysteine of the DOM7h-14-10 (R108C) AlbudAb prepared as described above.

DOM7h-14-10 (R108C) was desalted into 50 mM Sodium Phosphate, pH6.5, 5 mM EDTA. Maleimide activated peptide was then mixed with the protein at a 1:1 ratio and incubated to allow the conjugation to occur.

Conjugate was purified from un-reacted DOM7h-14-10 (R108C) by Ion Exchange chromatography in a similar manner to described above. Fractions enriched in conjugate were finally purified from free peptide using Protein L affinity purification in a similar manner to described above. The final DMS7605 conjugate was buffer exchanged and analysed by SDS-PAGE and Mass Spectroscopy.

Example 28

Pharmacologic profile of the Exendin-4 AlbudAb (DAT0115 made as Described above) and PYY (3-36) AlbudAb Fusion Peptide (DMS7605 made as Described in Example 27 and with the Structure shown in FIG. 14) in the Melanophore Functional Bioassay The pharmacologic profile of the Exendin-4 AlbudAb (DAT 0115) and the PYY(3-36) AlbudAb (DMS7605 made as described in example 27 and with the structure shown in FIG. 14 was determined in a melanophore functional bioassay using cells transfected with receptors of interest. The bioassay was performed essentially as described in example 21 with the following differences: 80 ug of cDNA was used for the human NPY1R, 40 ug was used for mouse NPY1R and 40 ug for other mouse and human NPY receptors (NPY2R, NPY4R and NPY5R).

The pharmacologic profiles of the Exendin-4 and PYY (3-36) AlbudAb fusion peptides (data not shown) reveal that the fusions bind and activate both mouse and human NPY receptors. DMS7605 binds NPY1R, NPY2R, NPY4R and NPY5R with NPY2R being most strongly activated (data not shown). The NPYR accession numbers are as follows: NPY1R: NM 00909 (human) and NM 010934 (mouse); NPY2R: NM 00910 (human) and NM 008731 (mouse); NPY4R: NM 005972 (human) and NM 008919 (mouse); NPY5R: NM 006174 (human) and NM 016708 (mouse).

Example 29

DMS7605 showed Dose Dependent Reduction in Body Weight Compared to Vehicle Control in the Diet Induced Obese (DIO) Mouse Model of Obesity The experiment was conducted in the diet induced obese (DIO) mouse obesity model to assess the efficacy of DMS7605 (aka DMS7167:PYY3-36). The aim of the study described here was to determine whether food intake and body weight over a 6 day period is affected by treatment with DMS7605. These results may be predictive for humans.

Male C57B1/6J mice (Taconic) were fattened on 60% kcal high fat diet (Research Diets D12492) for 12 weeks and then transferred to the in-house facility. Upon arrival, the mice were individually housed on alpha-dri bedding in a temperature and humidity controlled room (70-72° F., Humidity=48-50%, 5 AM/5 PM light cycle). The diet was changed to 45% high fat diet (Research Diets D12451) and the animals acclimated for 5 weeks. Animals were given ad libitum access to food and water. Prior to administration of compound, mice were injected subcutaneously with vehicle for one day and food consumption was monitored. Mice were grouped such that body weight and food consumption were not different between groups. Groups were dosed every other day with either vehicle or DMS7605 at doses of 3 mg/kg, 1 mg/kg, 0.3 mg/kg, or 0.1 mg/kg. Statistically significant changes ($p<0.05$ by T-test) in six day cumulative food intake were observed at 3 mg/kg (37.3% decrease), 1 mg/kg (31.3% decrease), and 0.3 mg/kg (21.8% decrease), while significant changes were not observed at 0.1 mg/kg (8.7% decrease, p=0.07 by T-test). Body weight was measured on days 0, 3, and 6 after start of dosing.

DMS7605 showed a dose dependent reduction in body weight compared to the vehicle control (FIG. 15). A significant reduction in body weight was observed at all doses ($p<0.01$ by two-way ANOVA followed by Bonferroni post-hoc analysis).

The invention claimed is:

1. A drug fusion or conjugate comprising (a) an insulinotropic agent or an incretin drug selected from: (i) GLP-1, (ii) exendin-4, and (iii) PYY (Peptide YY), present as a fusion or a conjugate with (b) a dAb which binds serum albumin selected from: (i) the DOM 7h-14-10 domain antibody (dAb) (SEQ ID NO 26); (ii) the DOM 7h-11-15 dAb (SEQ ID NO 27); or (iii) the DOM 7h-14-10 R108C domain antibody (dAb) (SEQ ID NO 42).

2. The fusion or conjugate according to claim 1, wherein the drug is selected from (a) the GLP-1 (7-37) A8G mutant which has the amino acid sequence shown in FIG. 1(*i*) (SEQ ID NO 9), or (b) the exendin-4 molecule which has the amino acid sequence shown in FIG. 1 (*j*) (SEQ ID NO 10) or (c) PYY3-36 or PYY 3-36 which has lysine at position 10 and has the amino acid sequence shown in FIG. 1(*s*) (SEQ ID NO 43).

3. The fusion or conjugate according to claim 1, which comprises an amino acid or chemical linker joining the drug and the dAb.

4. The fusion or conjugate according to claim 3, wherein the amino acid linker is a helical linker with the amino acid sequence shown in FIG. 1(*k*) (SEQ ID NO 11), or the gly-ser linker with the amino acid sequence shown in FIG. 1(*l*) (SEQ ID NO 12).

5. The fusion or conjugate according to claim 1, wherein the insulinotropic agent or the incretin drug is present as part of a fusion at either the N-terminal or C-terminal of the dAb.

6. The fusion or conjugate according to claim 1, which comprises an amino acid sequence selected from the following:

(a) Exendin 4, (G4S)3, linker DOM7h-14-10 fusion (DMS7139)

(SEQ ID NO 24)
HGEGTFTSDLSKQMEEEAVRLFIEWLKNGGPSSGAPPPSGGGGSGGGGS

GGGGSDIQMTQSPSSLSASVGDRVTITCRASQWIGSQLSWYQQKPGKAPK

LLIMWRSSLQSGVPSRFSGSGSGTDFTLTISSLQPEDFATYYCAQGLRHP

KTFGQGTKVEIKR, (b) Exendin 4, (G4S)3, linker DOM7h-11-15 fusion (DMS7143)

(SEQ ID NO 25)
HGEGTFTSDLSKQMEEEAVRLFIEWLKNGGPSSGAPPPSGGGGSGGGGS

GGGGSDIQMTQSPSSLSASVGDRVTITCRASRPIGTMLSWYQQKPGKAPK

LLILAFSRLQSGVPSRFSGSGSGTDFTLTISSLQPEDFATYYCAQAGTHP

TTFGQGTKVEIKR, or (c) A peptide conjugate which is:
  a DOM 7h-14-10 (R108C) AlbudAb conjugated to a C-terminally amidated PYY3-36 via a lysine (introduced at position 10 of PYY) and a 4 repeat PEG linker as shown in FIG. 14.

7. The fusion or conjugate according to claim 1, wherein the dAb is further formatted to increase its hydrodynamic size by attaching molecule(s) to the dAb selected from the following: a PEG group, serum albumin, transferrin, transferrin receptor or at least the transferrin-binding portion thereof, an antibody Fc region, or by conjugation to an antibody domain.

8. The fusion or conjugate according to claim 1, which comprises additional dAb moieties which have the same or different binding specificities to the DOM 7h-14-10 or DOM 7h-11-15 dAbs.

9. The fusion or conjugate according to claim 1, which binds to human serum albumin with KD in the range of about 5 micromolar to about 1 picomolar.

10. A pharmaceutical composition comprising the fusion or conjugate according to claim 1, in combination with a pharmaceutically or physiologically acceptable carrier, excipient or diluent.

11. The fusion or conjugate according to claim 6 which is Exendin 4, (G4S)3, linker DOM7h-14-10 fusion (DMS7139) HGEGTFTSDLSKQMEEEAVR-LFIEWLKNGGPSSGAPPPSGGGGGSGGGGSG GGGS-DIQMTQSPSSLSASVGDRVTIT-CRASQWIGSQLSWYQQKPGKAPKLLIM WRSSLQSGVPSRFSGSGSGTDFTLTISS-LQPEDFATYYCAQGLRHPKTFGQGT KVEIKR (SEQ ID NO 24).

* * * * *